US012303615B2

(12) United States Patent
Lee et al.

(10) Patent No.: US 12,303,615 B2
(45) Date of Patent: May 20, 2025

(54) DEMINERALIZED BONE PAPER

(71) Applicant: UNIVERSITY OF MASSACHUSETTS, Boston, MA (US)

(72) Inventors: Jungwoo Lee, Boston, MA (US);
Jaehyuck Shim, Boston, MA (US);
Ryan Carpenter, Boston, MA (US);
Yongkuk Park, Boston, MA (US);
Jun-Goo Kwak, Boston, MA (US)

(73) Assignee: University of Massachusetts, Boston, MA (US)

( * ) Notice: Subject to any disclaimer, the term of this patent is extended or adjusted under 35 U.S.C. 154(b) by 117 days.

(21) Appl. No.: 17/531,328

(22) Filed: Nov. 19, 2021

(65) Prior Publication Data

US 2022/0152274 A1    May 19, 2022

Related U.S. Application Data

(60) Provisional application No. 63/115,735, filed on Nov. 19, 2020.

(51) Int. Cl.
A61L 27/00        (2006.01)
A61L 27/36        (2006.01)
(Continued)

(52) U.S. Cl.
CPC ....... A61L 27/3608 (2013.01); A61L 27/3683 (2013.01); C12M 23/12 (2013.01);
(Continued)

(58) Field of Classification Search
CPC ........ A61K 35/28; A61K 35/32; A61K 31/47; C12Q 2563/00; A61L 27/3608;
(Continued)

(56) References Cited

U.S. PATENT DOCUMENTS 4,172,128 A  * 10/1979 Thiele ................... A61K 35/32
                                                    424/549
7,959,941 B2    6/2011 Knaack et al.
(Continued)

FOREIGN PATENT DOCUMENTS

WO    WO-9639203 A1 * 12/1996 ............... A61F 2/28
WO    2004/022120 A1    3/2004

OTHER PUBLICATIONS

Han, Bo, et al., "Quantitative and Sensitive In Vitro Assay for Osteoinductive Activity of Demineralized Bone Matrix, Journal of Orthopaedic Research", Journal of Orthopaedic Research, vol. 21, (2003), 648-654 (Year: 2003).*
(Continued)

Primary Examiner — Sarah W Aleman
Assistant Examiner — Rachel S Highland
(74) Attorney, Agent, or Firm — Thomas | Horstemeyer, LLP

(57) ABSTRACT

Disclosed herein are three-dimensional bone tissue grafts produced from stacked demineralized bone paper. Also disclosed are methods for treating a subject using tissue grafts produced from the disclosed demineralized bone paper. Also disclosed are assay systems that involves culturing bone-promoting cells on the disclosed demineralized bone paper.

6 Claims, 60 Drawing Sheets

(51) Int. Cl.

| | |
|---|---|
| C12M 1/00 | (2006.01) |
| C12M 1/32 | (2006.01) |
| C12N 5/077 | (2010.01) |
| G01N 1/28 | (2006.01) |
| G01N 33/483 | (2006.01) |

(52) U.S. Cl.
CPC ............ *C12M 23/22* (2013.01); *C12N 5/0669* (2013.01); *G01N 1/2813* (2013.01); *G01N 33/4833* (2013.01); *A61L 2300/414* (2013.01); *A61L 2430/02* (2013.01); *C12N 2527/00* (2013.01)

(58) Field of Classification Search
CPC ............ A61L 27/3683; A61L 2300/414; A61L 2430/02; A61L 27/365; A61L 27/3821; A61L 27/3847; G01N 33/4833; G01N 1/2813; C12M 23/12; C12M 23/22; C12M 21/08; C12N 5/0069; C12N 2527/00; C12N 2501/22; C12N 2501/60; C12N 2513/00; C12N 5/0654; A61P 19/00

See application file for complete search history.

(56) References Cited

U.S. PATENT DOCUMENTS

| | | | |
|---|---|---|---|
| 8,202,539 B2 | 6/2012 | Behnam et al. | |
| 8,753,689 B2 | 6/2014 | Morris et al. | |
| 9,849,214 B2* | 12/2017 | Woodell-May | A61L 27/3608 |
| 2004/0024184 A1* | 2/2004 | Kossida | C07K 14/723 435/325 |
| 2004/0086869 A1* | 5/2004 | Schembri | B01J 19/0046 506/9 |
| 2006/0293724 A1* | 12/2006 | Kronberg | C12M 35/02 607/51 |
| 2007/0231788 A1* | 10/2007 | Behnam | A61L 27/3847 435/4 |
| 2012/0122150 A1* | 5/2012 | Boren | G01N 1/44 435/351 |
| 2014/0228401 A1* | 8/2014 | Aftab | A61P 43/00 514/312 |
| 2016/0262915 A1* | 9/2016 | Mangiardi | A61F 2/90 |
| 2021/0261901 A1* | 8/2021 | Maguire | C12N 15/87 |
| 2022/0249533 A1* | 8/2022 | Varghese | A61K 47/36 |

OTHER PUBLICATIONS

Raggatt, Liza J., et al., "Cellular and Molecular Mechanisms of Bone Remodeling," The Journal of Biological Chemistry, vol. 285, No. 33 (2010) pp. 25103-25108.

Boyce, Brendan F., et al., "Functions of RANKL/RANK/OPG in bone modeling and remodeling," Arch. Biochem. Biophys., vol. 473, No. 2 (2008), pp. 139-146.

Parfitt, A. M., "The Cellular Basis of Bone Remodeling: The Quantum Concept Reexamined in Light of Recent Advances in the Cell Biology of Bone," Calcif. Tissue Int., vol. 36 (1984), pp. S37-S45.

Langdahl, Bente, et al., "Bone modeling and remodeling: potential as therapeutic targets for the treatment of osteoporosis," Ther. Adv. Musculoskel Dis., vol. 8, No. 6 (2016), pp. 225-235.

Manolagas, Stavros C., et al., "Bone Marrow, Cytokines, and Bone Remodeling - Emerging Insights into the Pathophysiology of Osteoporosis," New England Journal of Medicine, vol. 332, No. 5 (1995), pp. 305-311.

Morrison, Sean J., et al., "The bone marrow niche for haematopoietic stem cells," Nature, vol. 505 (2014), pp. 327-334.

Eriksen, E. F., "Normal and Pathological Remodeling of Human Trabecular Bone: Three Dimensional Reconstruction of the Remodeling Sequence in Normals and in Metabolic Bone Disease," Endocrine Reviews, vol. 7, No. 4 (2014), pp. 379-408.

Rogers, Katherine W., et al., "Morphogen Gradients: From Generation to Interpretation," Annu. Rev. Cell Div. Biol., vol. 27 (2011), pp. 377-407.

Vortkamp, A., "Skeleton morphogenesis: Defining the skeletal elements," Curr. Biol. 7 (1997), pp. R104-R107.

Wartlick, Orturd, et al., "Morphogen Gardient Formation," Cold Spring Harb Perspect Biol. vol. 1 (2009) (22 pages).

Kunz, Leo, et al., "A 3D Tissue-wide Digital Imaging Pipeline for Quantitation of Secreted Molecules Shows Absence of CXCL12 Gradients in Bone Marrow," Cell Stem Cell, vol. 25 (2019), pp. 846-854.

Bellido, Teresita, et al., "Ex Vivo Organ Cultures as Models to Study Bone Biology," JBMR Plus (WOA), vol. 4, No. 3 (2020) (20 pages).

Koons, Gerry L., et al., "Materials design for bone-tissue engineering," Nature, vol. 5 (2020), pp. 584-603.

Kohli, Nupur, et al., "Bone remodelling in vitro: Where are we headed?—A review on the current understanding of physiological bone remodelling and inflammation and the strategies for testing biomaterials in vitro," Bone, vol. 110 (2018), pp. 38-46.

Rumpler, M., et al., "Osteoclasts on Bone and Dentin in Vitro: Mechanism of Trail Formation and Comparison of Resorption Behavior," Calcif. Tissue Int., vol. 93 (2013), pp. 526-539.

Gruskin, Elliott, et al., "Deminerralized bone matrix in bone repair: History and use," Advanced Drug Delivery Reviews, vol. 64 (2012), pp. 1063-1077.

Reznikov, Natalie, et al., "Fractal-like hierarchical organization of bone begins at the nonscale," Science, vol. 360 (2018) (11 pages).

Lee, Jungwoo, et al., "Three-Dimensional Cell Culture Matrices: State of the Art," Tissue Engineering, Part B, vol. 14, No. 1 (2008), pp. 61-86.

Borciani, Giorgia, et al., "Co-culture systems of osteoblasts and osteoclasts: Simulating in vitro bone remodeling in regenerative approaches," Acta Biomaterialia, vol. 108 (2020), pp. 22-45.

Ren, Xiaoyan, et al., "Osteoprotegerin reduces osteoclast resorption activity without affecting osteogenesis on nanoparticlulate mineralized collagen scaffolds," Science Advance, vol. 5 (2019) (12 pages).

Bennink, Lucas L., et al., "Visualizing collagen proteolysis of peptide hybridization: From 3D cell culture to in vivo imaging," Biomaterials, vol. 183 (2018), pp. 67-76.

Chen, Xiyi, et al., "Second harmonic generation microscopy for quantitative analysis of collagen fibrillar structure," Nature, vol. 7, No. 4 (2012), pp. 654-669.

Boonrungsiman, Suwimon, et al., "The role of intracellular calcium phosphate in osteoblast-mediated bone apatite formation," PNAS, vol. 109, No. 35 (2012), pp. 14170-14175.

Miller, Scott C., et al., "Bone Lining Cells: Structure and Function," Scanning Microscopy, vol. 3, No. 3 (1989), pp. 953-961.

Plotkin, Lilian I., et al., "Beyond gap junctions: Connexin43 and bone cell signaling," Bone, vol. 52 (2013), pp. 157-166.

Matic, Igor, et al., "Quiescent Bone Lining Cells Are A Major Source of Osteoblasts During Adulthood," Stem Cells, vol. 34, No. 12 (2016), pp. 2930-2942.

Jansen, Ineke D. C., et al., Osteoclast Fusion and Fission, Calcif. Tissue Int., vol. 90 (2012), pp. 515-522.

Jacome-Galarza, Christian E., et al., "Developmental origin, functional maintenance and genetic rescue of osteoclasts," Nature, vol. 568 (2019), pp. 541-562.

Sims, Natalie A., et al., "Osteoclasts Provide Coupling Signals to Osteoblast Lineage Cells Through Multiple Mechanisms," Annual Review Physiol., vol. 82 (2020), pp. 507-529.

Furuya, Masayuki, et al., "Direct cell-cell contact between mature osteoblasts and osteoclasts dynamically controls their functions in vivo," Nature Communications, vol. 9 (2018) (12 pages).

Choi, Ji Sun, et al., "Marrow-inspired matrix cues rapidly affect early fate decisions of hematopoietic stem and progenitor cells," Science Advances, vol. 3 (2017) (10 pages).

Igwe, John, et al., "Nanostructured Scaffolds for Bone Tissue Engineering," Stud. Mechanobiol. Tussue Eng. Biomater. vol. 8 (2011), pp. 169-192.

(56) References Cited

OTHER PUBLICATIONS

Chen, Xiao, et al., "Osteoblast-Osteoclast Interactions," Connect Tissue Res., vol. 59, No. 2 (2018), pp. 99-107.
Bonewald, Lynda F., "The Amazing Osteocyte," Journal of Bone and Mineral Research, vol. 26, No. 2 (2011), pp. 229-238.
Xiong, Jinhu, et al., "Matrix-embedded cells control osteoclast formation," Nat. Med., vol. 17, No. 10 (2012), pp. 1235-1241.
Nakashima, Tomoki, et al., "Evidence of osteocyte regulation of bone homeostasis through RANKL expression," Nature Medicine, vol. 17, No. 10 (2011), pp. 1231-1234.
Li, Yan, et al., "B cells and T cells are critical for the preservation of bone homeostasis and attainment of peak bone mass in vivo," Blood, vol. 109, No. 9 (2007), pp. 3839-3848.
McClune, Brian L., et al., "Osteoporosis after Stem Cell Transplantation," Curr. Osteoporos. Rep., vol. 11 (2013), pp. 305-310.
Seeman, Ego, "Modeling and Remodeling, The Cellular Machinery Responsible for the Gain and Loss of Bone's Material and Structural Strength," Principles of Bone Biology, 3rd Edition (2008) Chapter 1.
Raina, Vinita, "Normal Osteoid Tissue," J. Clin. Path., vol. 25 (1972), pp. 229-232.

\* cited by examiner

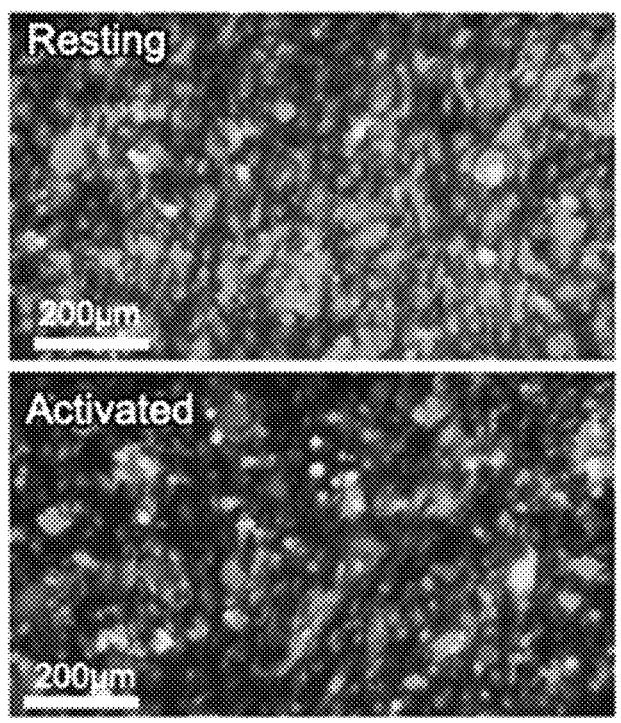
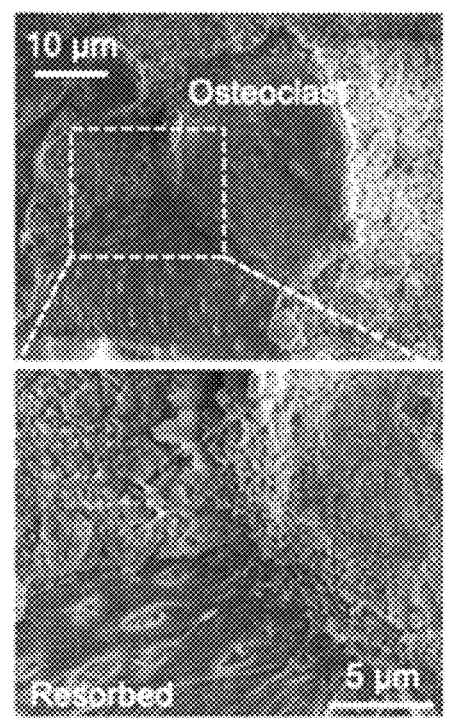
FIG. 4C
FIG. 4D
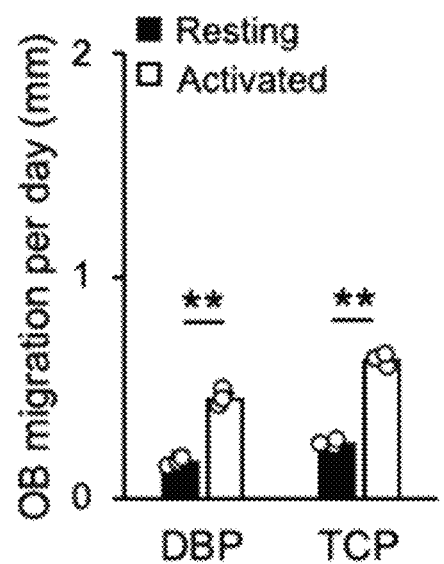
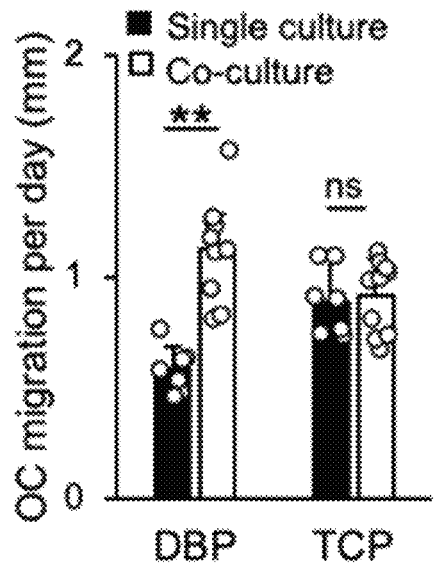
FIG. 4E
FIG. 4F

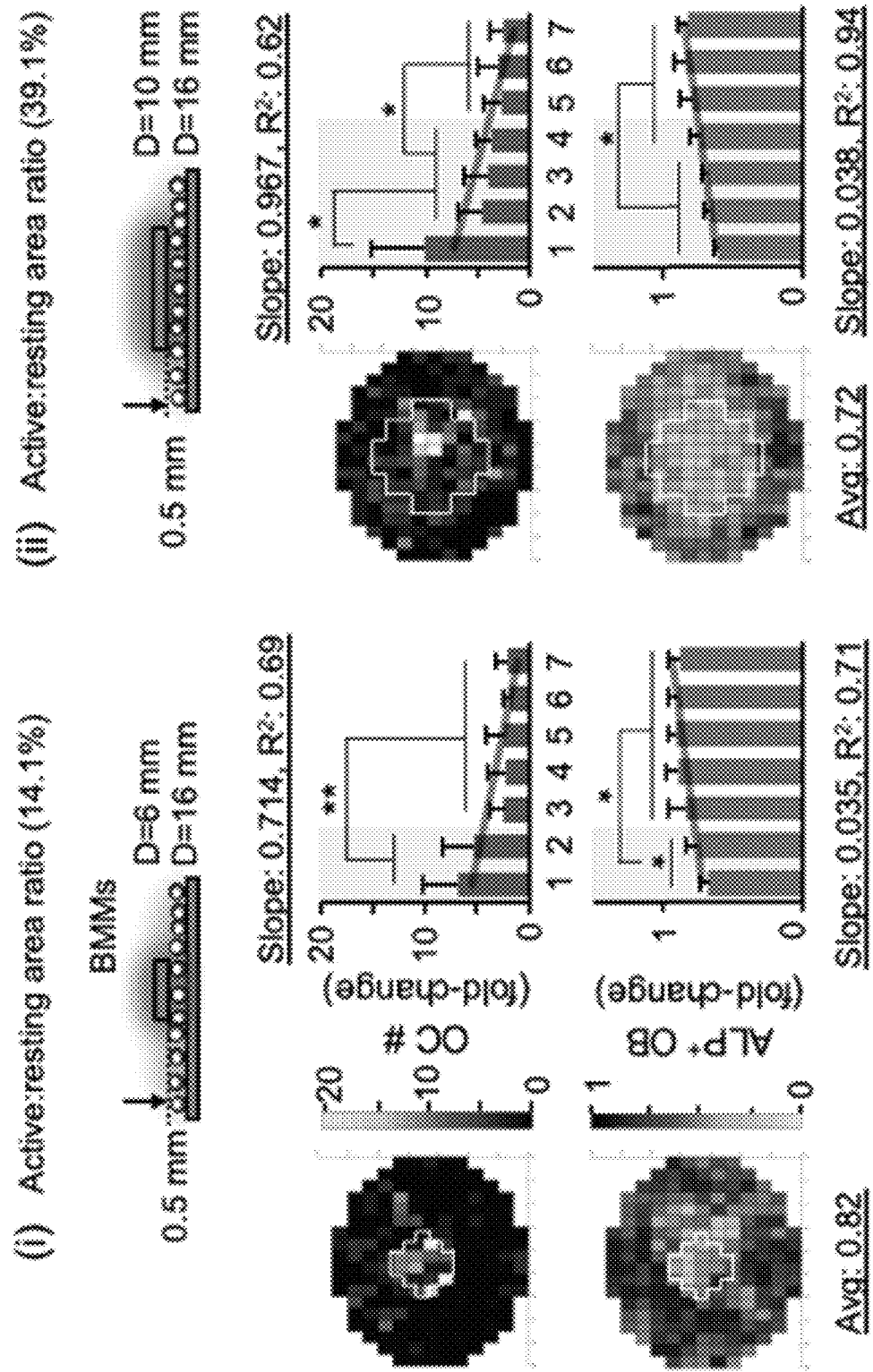
FIG. 6D (i-ii)

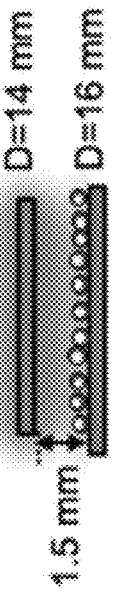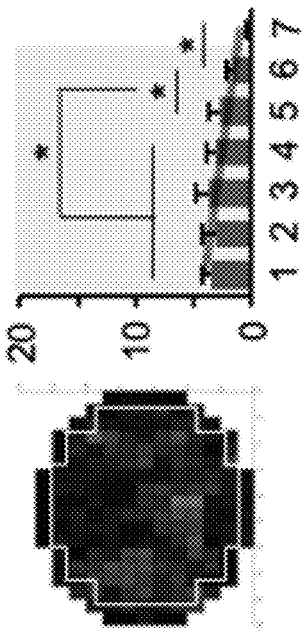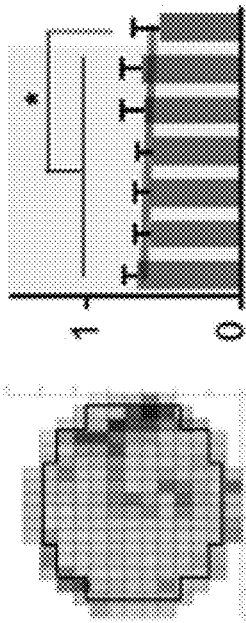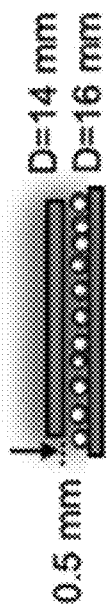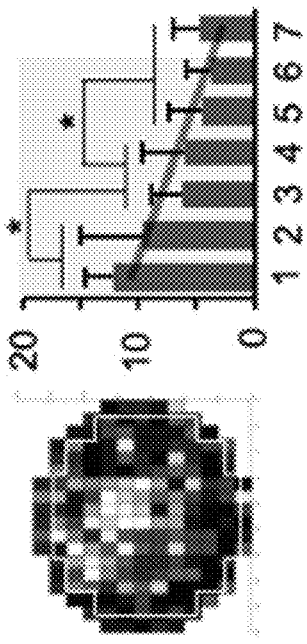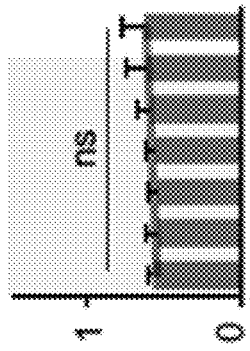
FIG. 6D (iii-iv)

FIG. 21A
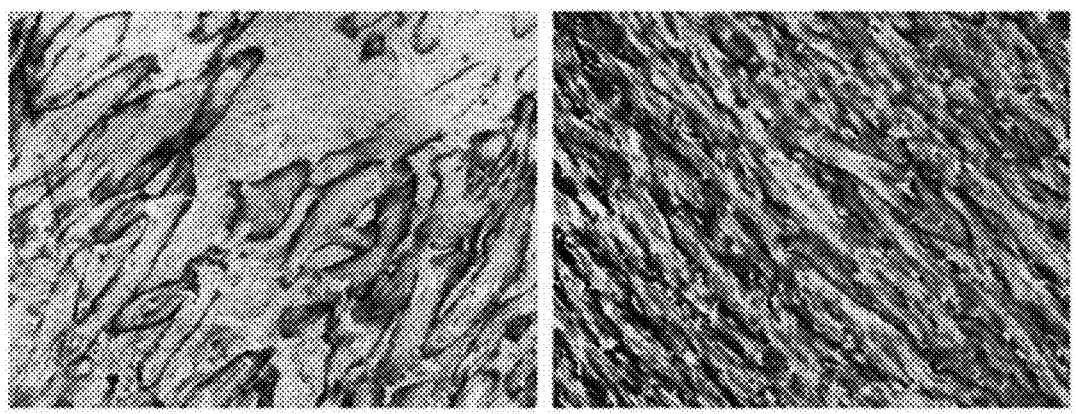
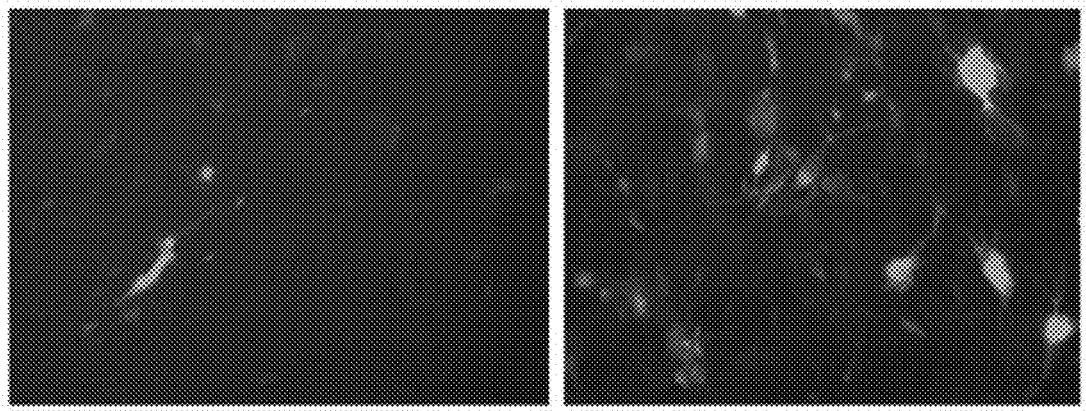
FIG. 21B

DEMINERALIZED BONE PAPER

CROSS-REFERENCE TO RELATED APPLICATIONS

This application claims benefit of U.S. Provisional Application No. 63/115,735, filed Nov. 19, 2020, which is hereby incorporated herein by reference in its entirety.

STATEMENT REGARDING FEDERALLY SPONSORED RESEARCH OR DEVELOPMENT

This invention was made with Government Support under Grant No. CA163671 and CA237171 awarded by the National Institutes of Health, and Grant No. 1944188 awarded by the National Science Foundation. The Government has certain rights in the invention.

BACKGROUND

Bone is a dynamic, multifunctional tissue that regulates mineral homeostasis, blood-forming, and mechanical structure in response to changing physical stresses and physiological needs. Bone surface undergoes repeated remodeling by the paired action of osteoclasts, which break down bone, and osteoblasts, which form new bone (Raggatt, L J, et al. J Biol Chem 2010 285:25103-25108). During active bone remodeling, osteoblasts build osteoids, collagen-based structures of extracellular matrix (ECM) that they then mineralize to form new lamellar bone (Raggatt, L J, et al. J Biol Chem 2010 285:25103-25108). After an osteoid has been mineralized, osteoblasts on the bone surface differentiate into their resting state: bone lining cells (Raggatt, L J, et al. J Biol Chem 2010 285:25103-25108). The cellular processes of the bone remodeling cycle occur at localized spots under tight regulation by stimulatory and suppressive molecules such as receptor activator of NF-κB ligand (RANKL) and its soluble decoy receptor, osteoprotegerin (OPG) (Boyce, B F, et al. Arch Biochem Biophys 2008 473:139-146). RANKL stimulates bone marrow mononuclear cells (BMMs) to differentiate into osteoclasts by binding to its receptor, RANK, whereas OPG blocks RANK-RANKL signaling by competitively binding to RANKL and thus suppressing osteoclast differentiation (Boyce, B F, et al. Arch Biochem Biophys 2008 473:139-146).

Active- and resting-state bone tissue surfaces coexist within every bone. There are 1 million active remodeling sites in a normal adult skeleton at any one time, which account for 5 to 20% of the total bone surface (Parfitt, A M. Calcif Tissue Int 1984 36 Suppl 1:S37-45; Langdahl, B, et al. Ther Adv Musculoskel 2016 8:225-235). Molecular regulation is essential to localize bone remodeling activity and prevent unnecessary remodeling and over-resorption. Imbalanced bone remodeling can lead to osteoporosis (Manolagas, S C, et al. NEJM 1995 332:305-311), decreased bone marrow hematopoietic activity (8), or increased risk of bone metastasis (Croucher, P I, et al. Nature Rev Cancer 2016 16:373). To develop effective treatments for these conditions, it is imperative that one understand how localized bone remodeling is regulated in the trabecular bone cavities.

Spatiotemporal profiles of regulatory molecules may play a critical role in directing localized bone remodeling activity. In normal bone remodeling, trabecular bone undergoes continuous structural change but maintains consistent morphology and mass (Eriksen, E F. Endocr Rev 1986 7:379-408). This implies that localized bone remodeling is in part regulated by bone turnover rate and morphology. Countergradients of stimulative and inhibitory molecules are key regulatory mechanisms in localized morphogenic activity that direct the size and shape of tissue development and regeneration (Rogers, K W, et al. Annu Rev Cell Dev Biol 2011 27:377-407; Vortkamp, A. Curr Biol 1997 7:R104-R107). The same principle may apply to the regulation of trabecular bone remodeling. Osteoblasts secrete both stimulative and suppressive molecules, and their secretory profiles change depending on whether they are in an active or a resting state (Wartlick, O, et al. Cold Spring Harb Perspect Biol 2009 1:a001255). Secreted regulatory molecules form diffusion gradients as a function of the diameters of the trabecular bone cavities (Kunz, L, et al. Cell Stem Cell 2019 25:846-854). Therefore, key determinants of the spatiotemporal profile of regulatory molecules in trabecular bone cavities are the extent of remodeling activity and the cavity diameter. To investigate this concept in more detail, a new experimental model is needed.

Available experimental models have limited ability to reproduce the spatiotemporal complexity of trabecular bone. Mouse models have limited utility to investigate cellular and molecular processes of trabecular bone remodeling because the inner bone surface is anatomically inaccessible and researchers have limited ability to manipulate the structure and dimensions of the trabecular bone. Explanted bone chips are more accessible, but local manipulation of cellular metabolic activity and dimensional control of bone are limited, and reproducibility is low because tissue dimensions are variable and vascular occlusion decreases cell viability over time (Bellido, T. et al. JBMR Plus 2020 4:e10345).

In vitro bone tissue models allow greater experimental control and access, and many biomaterials and material-processing techniques have been introduced to reproduce the material and structural properties of bone ECM in in vitro bone tissue models (Koons, G L, et al. Nat Rev Mater, 2020 5:584-603). However, existing in vitro models do not reproduce the bone tissue complexity and molecular and cellular processes of bone remodeling (Kohli, N, et al. Bone 2018 110:38-46). For example, compact bone disks have been used to assess osteoclasts function (Rumpler, M, et al. Calcif Tissue Int 2013 93:526-539) and demineralized trabecular bones have been used to culture osteoblasts (Gruskin, E, et al. Adv Drug Deliv Rev 2012 64:1063-1077). However, grinding compact bone is burdensome and low throughput, and the opacity of bone restricts in situ optical microscopy. Demineralized trabecular bone supports high osteogenic activity (Gruskin, E, et al. Adv Drug Deliv Rev 2012 64:1063-1077), but its 3D architecture is determined by the individual bone matrix and is difficult to standardize or manipulate for mechanistic investigation. Collagen gels provide a biochemical milieu comparable to that of bone ECM but fail to reproduce the density and structural organization of collagen fibers (Reznikov, N, et al. Science 2018 360:eaao2189). Hydroxyapatites mimic inorganic aspects of bone ECM but lack the organic materials that are known to provide biochemical signals (Koons, G L, et al. Nat Rev Mater, 2020 5:584-603). Blends of organic and inorganic materials better represent bone ECM but do not provide multiscale structural complexity (Koons, G L, et al. Nat Rev Mater, 2020 5:584-603). Techniques have been developed to produce nanoscale surface roughness, microscale pore geometry, and macroscale trabecular architecture in biomaterials—including porogen-based porous architecture, electrospun fibrous meshwork, and 3D printed trabecular bone structure—but these processes do not recapitulate the hierarchical composite structures of trabecular bone in the critical dimensions of lamellae (5-25 µm), collagen fibers (1-2 µm), and collagen fibrils (10-300 nm). In addition, most in vitro biomaterial studies have focused on either osteoblasts or osteoclasts, but few studies have involved osteoblasts and osteoclasts in coculture. In the body, active osteoblasts and osteoclasts are only present transiently at local spots, while most of the bone surface is in a quiescent state characterized by bone lining cells. The role of bone lining cells in the initiation and termination of the bone remodeling cycle has not been investigated, and failures in initiation or termination of the bone remodeling cycle could be a critical factor in bone remodeling imbalance.

SUMMARY

The demineralized bone matrix has been used for clinical bone tissue regeneration and in vitro bone tissue engineering with the high osteoinductive property. The potential of the demineralized bone matrix for in vitro bone tissue modeling has not been fully exploited. Demineralized compact bone was processed into thin sections having a standardized thickness and surface area, named demineralized bone paper (DBP). DBP preserves intrinsic bone matrix complexities such as the hierarchical assembly of collagen fibers and closely resembles the unmineralized state of the bone matrix known as osteoid. DBP also exhibits semi-transparency for optical imaging and sufficient mechanical stability for handling. These properties allowed to create standardized, functional, and analytical bone tissue models for preclinical testings. In addition, DBP allowed an additive manufacturing of lamellar structural 3D bone tissues via layering, rolling, and folding osteoblasts and bone marrow stromal cell pre-seeded multiple DBPs. Collagen fibers in DBP also respond sensitively to applied mechanical forces and promote bone formation by osteogenic cells. Finally, DBP are functionalized prior, during, or post usage to achieve desired properties to direct biological processes both in vitro and in vivo.

Disclosed herein is a three-dimensional bone tissue graft produced from demineralized bone paper. In particular, the disclosed tissue graft can involve a plurality of demineralized compact bone slices stacked in layers to form the three-dimensional configuration. In some embodiments, the layers are first cultured in two-dimensional culture with bone-promoting cells. This results in attachment of the cells to the layers prior to stacking. Once stacked, the bone-promoting cells can promote remineralization of the slices into a solid three-dimensional graft. Therefore, the disclosed graft can contain bone-promoting cells between some or all of the layers.

In some embodiments, the demineralized compact bone slices are 10-1,000 µm in thickness, including about 10-100, 100-500, 500-1000, 10-500, or 100-1000 µm in thickness. Therefore, the slices can be 10, 11, 12, 13, 14, 15, 16, 17, 18, 19, 20, 25, 30, 35, 40, 45, 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950, or 1000 µm in thickness.

The size and shape of the slices can be selected by the use based on a combination of donor material size and desired size and shape of the tissue graft. It is understood that the maximum surface area of the slices is in part dictated by the size of donor compact bone. Likewise, the minimum surface area is dictated by practicality. For example, in some embodiments, the demineralized compact bone slices have a surface area of at least 0.1, 0.2, 0.3, 0.4, 0.5, 0.6, 0.7, 0.8, 0.9, or 1 cm$^2$, including a surface area of from 0.1-10, 1-5, 0.1-5, or 1-10 cm$^2$. In some embodiments, the cutting direction is selected to optimize collagen structure.

In some embodiments, the compact bone slices have tailored shapes configured to produce a predetermined geometry when the slices are stacked. For example, the predetermined geometry can be patient-specific. The geometry can be determined by 3D scan or other such means, which can then be virtually "sliced" using software to identify shapes for each slice. Slicer software is currently available for 3D printing applications and could be adapted for this purpose. Once the shape is determined, compact bone slices can be cut into the desired shapes using a plotter cutter.

Suitable bone-promoting cells for use in the disclosed grafts include osteoblasts, bone marrow stromal cells, mesenchymal cells, or any combination thereof. Cells can be autologous, allogeneic, or xenogeneic, depending on the intended use. In some embodiments, the cells are derived from the subject that will receive the tissue graft. Therefore, in some embodiments, cells are obtained from the subject and then cultured in vitro to expand and optionally differentiate the cells into bone-promoting cells before adding them to the bone slices.

The tissue graft can also contain exogenous bone-promoting agents to promote osteogenesis in the graft. In some embodiments, the bone slices and bone-promoting cells are cultured in the presence of the bone-promoting agents prior to stacking. In some embodiments, the bone-promoting agents are added to the graft after the slices have been stacked. For example, the stacked slices can be cultured in a medium containing the bone-promoting agents. Non-limiting examples of bone-promoting agents include drugs, growth factors, viral particles, or any combination thereof.

In some embodiments, the disclosed graft is produced by a method that involves first providing a plurality of individual demineralized compact bone slices. The demineralized compact bone slices are preferably cut into tailored shapes. Therefore, the method can also involve soaking the demineralized compact bone slices in a water-soluble polymer, such as polyvinylalcohol, to increase mechanical stability of the slices.

Bone-promoting cells are next cultured on the individual demineralized compact bone slices in a medium comprising bone-promoting agents so as to produce seeded bone slices. The seeded bone slices are then stacked to produce a three-dimensional bone tissue graft. Bone-producing cells can attach on adjacent sides of the demineralized bone slices, which can function as biological glue to form a free-standing 3D bone tissue graft. Remineralization by bone-promoting cells can proceed after forming 3D bone tissue stacks. Therefore, the stacked slices can then be cultured in a medium configured to produce a three-dimensional bone tissue graft comprising a multi-layered lamellar bone structure. When stacked bone layers become too thick, e.g. thicker than 500 µm, conduit structure (250-500 µm diameter) can be included during additive manufacturing. The surface of conduit can be coated with endothelial cells. A bioreactor can be used to improve medium perfusion through 3D conduit structure to support cell proliferation and remineralization.

In some embodiments, demineralized bone paper seeded with bone forming cells is exposed to mechanical stimulations as a form of mechanical agitation, sonic vibration, fluidic shear forces, magnetic attraction/repulsion (frequency 1-100,000 Hz, displacement 0.1-1,000 µm). In some embodiments, these mechanical stimulations are applied to demineralized bone paper with osteogenic cells for 1 to 1,440 minutes continuously and/or intermittently (1, 3, 5, 10, 20, 30, 60, 120, 240, 480, 960, 1440 minutes in multiple cycles for 1-4 weeks).

Also disclosed herein is an assay system that involves a multi-well culture plate; one or more layers of semi-transparent, compact bone slices in one or more wells of the multi-well culture plate, further comprising bone-promoting cells on the one or more layers; and a culture medium configured to promote or maintain bone development.

Also disclosed herein is an assay system that involves a multi-well culture plate; one or more (e.g. 1, 2, 3, 4, 5, 6, 7, 8, 9, 10, or more) layers of semi-transparent, compact bone slices in one or more wells of the multi-well culture plate, further comprising bone-promoting cells on the one or more layers; remineralized and decellularized compact bone slices that retain semi-transparency while representing complete organic and inorganic bone extracellular matrix material and structural complexity, and a culture medium configured to promote or maintain bone development.

In some embodiments, the disclosed assay system further involves agents to detect and/or measure one or more parameters of bone development. For example, the one or more parameters can include mineralization or resorption of pre-existing mineral.

In some embodiments, the compact bone slices are demineralized and the culture medium is configured to promote bone development. In some embodiments, the compact bone slices are mineralized or remineralized and the culture medium is configured to maintain bone development.

Also disclosed are functional assays involving a single layer of demineralized bone paper. For example, disclosed herein is a bone-forming (mineral resorption) assay by osteoblasts. In this embodiment, bone-promoting cells can be cultured on demineralized bone matrix with a candidate drug being loaded in the culture medium. At the end of the culture period, mineral deposition in the bone paper can be quantitatively assessed.

Likewise, disclosed is a bone-resorbing assay by osteoclasts. In this embodiment, demineralized bone slices can be remineralized by culturing bone-promoting cells. During the culture, fluorescent molecules can be added in the culture medium, which will be integrated in mineral during remineralization process. When cells are removed, a fluorescent mineral layer will remain. Preferably, the bone slices are thin enough to allow microscopic imaging. Florescent mineral can therefore allow easy monitoring of the osteoclast mineral resorption process.

Finally, a bone remodeling assay is disclosed that involves co-culture of osteoblasts and osteoclasts. In these embodiments, osteoblasts can be cultured on demineralized bone slices long enough to cause remineralization, e.g. for 1 week. After remineralization, bone marrow mononuclear cells can be introduced. Stimulation agents or drugs can be loaded, which stimulate osteoblasts and subsequently induce osteoclast formation and mineral resorption process.

Also disclosed are functional assays involving a multiple layers of demineralized bone paper. For example, different thickness of demineralized bone slices can be used to mimic osteoporosis related bone thickness reduction. Likewise, slices with the same thickness but alternating high and low cellularized demineralized bone slices can be used to mimic drug induced reduction of osteoclast connectivity.

In addition, disclosed are functional assays that go beyond bone tissue. For example, disclosed is a co-culture with hematopoietic stem cells to assess hematopoietic bone marrow toxicity testing. Likewise, disclosed is a co-culture with cancer cells to assess chemotherapeutic toxicity and efficacy for bone metastasized tumor cells.

Also disclosed are method for assaying the effect of an agent on bone development or health that involves adding a candidate agent to the culture medium of a disclosed assay system; and measuring at least one parameter of bone development in the assay system to determine if the candidate agent affected bone development or health.

Also disclosed are methods for treating a subject that involves obtaining bone-promoting cells from the subject; culturing the bone-promoting cells on a plurality of demineralized compact bone slices so as to produce functionalized bone slices; stacking the functionalized compact bone slices into a predetermined geometry; culturing the functionalized compact bone slices to produce a tissue graft comprising a multi-layered lamellar bone structure; and implanting the tissue graft into the subject.

Also disclosed is a demineralized bone paper produced by a method that involves cutting a cortical bone into chunks; removing bone marrow and muscle tissues; treating the chunks to dissolve residual lipids and cell debris; demineralizing the chunks with hydrochloric acid (HCl) in a cyclic pressure chamber; and freezing and sectioning the demineralized chunks into 10 to 150 μm thin sections so as to produce a demineralized bone paper.

Also disclosed is a microfluidic bone marrow chip that involves the disclosed DBP and a semi-permeable membrane that compartmentalize a microfluidic chip into sinusoid and interstitial chambers, wherein the interstial chamber is in contact with the DBP. For example, the membrane can be a polydimethylsiloxane (PDMS) or polycarbonate track-etched (PCTE) membrane. In some embodiments, the sinusoid chamber is endothelized. For example, the sinusoid chamber can contain human umbilical cord blood cells, primary human endothelial cells, primary mouse endothelial cells, human and mouse endothelial cell lines, etc. In some embodiments, the interstitial chamber can be filled with hematopoietic cytokine containing media, methylcellulose media, or primary human and mouse bone marrow harvest, etc. The interstitial chamber can in some embodiments be periodically perfused with first medium. In some embodiments, the first medium contains hematopoietic growth factors, drugs (e.g., chemotherapeutics, osteogenic stimulants, vitamin D3, parathyroid hormones, prostaglandin E2). The sinusoid chamber can also be continually perfused with a second medium. In some embodiments, the second medium can contain blood plasma, whole blood, whole blood spiked with human or mouse cancer cells, chemotherapeutics, bone marrow targeting drug compounds, etc.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A shows a bovine femur that was (i) cut into blocks, and the muscular tissues were removed and the marrow fat was dissolved in chloroform and methanol. (ii) Cleaned bone blocks were demineralized in 1.2 N HCl solution, a process that generates $CO_2$ bubbles. (iii) The demineralization process was restricted by the significant diffusion limit through dense bone matrix. Even extended HCl treatment (4 weeks) resulted in minimal demineralization. FIG. 1B shows a programmable cyclic pressure chamber was devised to expedite the demineralization process. The optimal operating procedure was 4 bar with a 10-second on-off interval. FIG. 1C shows characterization of demineralized bone blocks processed for 5 days under three pressure conditions. (i) Cross-sectional images of demineralized bone blocks soaked in rhodamine dye. Dye penetration indicates the depth of demineralization. (ii) Quantitative analysis confirmed significantly greater demineralization depth with cyclic pressure than with static pressure or no pressure (n=5). FIG. 1D shows (i) Radiographic images of unprocessed and processed bovine compact bone. (ii) Quantitative comparison of contrast (a.u.: arbitrary unit, n=3). FIG. 1E shows (i) Demineralized bone was sectioned into 20- to 100-µm-thick slices with a cryostat to form DBP. (ii) The DBP was cut into disks to fit 96-, 48-, 24-, or 12-well plates. FIG. 1F shows (i) Cross-sections of DBP with three thicknesses and corresponding (ii) optical transparency as a percentage of that of TCP and (iii) stiffness (n=6). FIG. 1G shows bone structure is preserved in DBP. (i) Concentric lamellae are apparent in transverse sections. (ii) Parallel lamellae are apparent in vertical sections. (iii) Scanning electron micrographs shows densely aligned collagen fibril bundles. FIG. 1H shows biochemical integrity of collagen is preserved in DBP. (i) Fluorescent images of intact DBP (top) and heat-treated DBP (bottom) stained with fluorescent-dye conjugated collagen hybridizing peptides that specifically bind to denatured collagen fibrils. (ii) Multiphoton second harmonic image shows aligned collagen fibrillar structure on DBP (top) whereas heat-treated DBP (bottom) showed greatly decreased second harmonic signal. FIG. 1I shows cellular materials are removed from DBP by sodium dodecyl sulfate. (i) Nuclear DAPI staining of DBP before and after the treatment. (ii) Quantitative analysis of fluorescent intensity (a.u.: arbitrary unit, n=30). (*P<0.05, **P<0.01).

FIG. 2A shows (i) osteoblasts harvested from DsRed reporter mice. (ii) Fluorescent micrograph of osteoblasts migrating out from mouse bone chips. FIG. 2B shows osteoblasts grown on vertically sectioned DBP for 1 week developed elongated morphology aligned with the lamellar structure, whereas those grown on TCP showed irregular shape and alignment. (i) Immunofluorescent staining of actin filaments in osteoblasts. (ii) Circular histogram of cell alignment angles with respect to the collagen alignment of DBP (n=100). FIG. 2C shows (i) multiphoton second harmonic imaging microscopy shows that osteoblasts on DBP deposit collagen fibers directionally aligned with the lamellar structure, whereas those on TCP had irregular collagen fiber alignment. (ii) Circular histogram of collagen fiber alignment angles with respect to the collagen alignment of DBP (n=100). FIG. 2D shows osteoblasts on DBP rapidly covered the entire surface with minerals, whereas those on TCP only mineralized a few localized regions. (i) Alizarin red mineral stain on Day 0 and Day 4. (ii) Osteoblasts on DBP continued to deposit significantly more minerals than those on TCP did for 16 days (n=3). FIG. 2E shows confocal z-stack images of osteoblasts cultured on DBP and TCP for 1 week after fluorescent calcein staining show notably different mineral deposition patterns. A cross-sectional image shows that mineral deposition on DBP occurred beneath osteoblasts. FIG. 2F shows cross-section of 100-µm-thick DBP stained with alizarin red after 3 weeks of culture with osteoblasts shows remineralization depth (n=3). FIGS. 2G-2H show comparison of mineral layer deposited by 3-week culture of osteoblasts on DBP and mineral layer deposited by chemical reaction in simulated body fluid without osteoblasts. Both were subjected to thermal decomposition to remove the organic components. FIG. 2G shows brightfield micrographs show notably different light reflection. FIG. 2H shows SEM show different surface morphology of mineral layers. Surface roughness was characterized by an optical profiler (n=6). (*P<0.05, **P<0.01).

FIG. 3A shows osteoblasts cultured for 2 weeks on DBP migrated significantly less than those cultured for 2 weeks on TCP (n=25). FIG. 3B shows osteoblasts cultured for 1 week on DBP decreased proliferation, whereas those on TCP increased proliferation (n=3). FIG. 3C shows osteoblasts cultured on DBP for 1 week developed gap junction-mediated intercellular communication. (i) Immunofluorescent staining of connexin 43, a key molecule in gap junction communication. (ii) Quantitative time-lapse monitoring of fluorescent $Ca^{2+}$ flux of three adjacent cells under potassium stimulation. FIG. 3D shows a bone surface healing assay. (i) A scratch was made on a 1-week culture of osteoblasts on DBP and repair of the damaged mineral surface was monitored over 5 days. (ii) Osteoblasts migration increased transiently during the healing process (n=3-5). FIG. 3E shows osteoblasts cultured on DBP for 1 week regained proliferative activity when they were cultured on TCP. (i) Fluorescent images of mature osteoblasts migrating out of DBP treated with collagenase (left) and proliferating on TCP (right). (ii) Within 1 week, mature osteoblasts released from DBP and grown on TCP regained mitogenic activity similar to that of osteoblasts that had been grown on TCP continuously (n=10). FIG. 3F shows an osteoblast phenotypic switching assay. (i) Schematic of experimental procedure and metabolic state changes in osteoblasts. (ii) The cycle of switching from a resting state on DBP to a proliferative state on TCP was successfully repeated three times (n=4). (*P<0.05, **P<0.01).

FIGS. 4A to 4K show coculture of bone lining cells and bone marrow mononuclear cells (BMMs) on DBP under chemical stimulation recapitulates the bone remodeling cycle. FIG. 4A shows experimental procedure to recapitulate the bone remodeling cycle. After osteoblasts (OBs) mineralize DBP, they enter a resting state characterized by high OPG and low RANKL secretion. Activation by vitamin D3 (VD3) and PGE2 causes the OBs to secrete less OPG and more RANKL, which creates a permissive environment for bone remodeling and induces BMMs to differentiate into osteoclasts (OCs). After the stimulation, the system gradually returns to the resting secretory milieu. FIG. 4B shows stimulation of bone lining cells on DBP with VD3 and PGE2 caused a temporary increase in RANKL/OPG secretion ratio (n=3-5). FIG. 4C shows fluorescence micrographs show that activated OBs on DBP induce BMMs to differentiate into OCs. FIG. 4D shows SEM confirmed functional mineral resorption by osteoclasts. FIG. 4E shows stimulated OBs migrated 2 times faster than their unstimulated counterparts on both DBP and TCP (n=4). FIG. 4F shows on DBP, OCs cocultured with stimulated OBs migrated twice as fast as OCs stimulated in the absence of OBs. On TCP, OCs cocultured with stimulated OBs migrated at the same rate as OCs stimulated in the absence of OBs (n=10). FIG. 4G shows on DBP, OCs underwent both cell fission and cell fusion. FIG. 4H shows on TCP, OBs were readily pushed by large multinucleated OCs, whereas on DBP the OBs stayed in place. FIG. 4I show on TCP, OCs underwent cell fusion repeatedly until cells became giant and underwent apoptosis.

After apoptosis, the large actin-ring structure of the OC remained and prevented migration of neighboring OBs for 10 hours. On DBP, this phenomenon was less pronounced because the OCs were smaller, and apoptosis was infrequent. FIG. 4J shows brightfield images of ALP show that OBs on DBP and TCP secreted less functional enzyme after they were activated (n=3-6). This indicates that activation interrupts mineral deposition by OBs. FIG. 4K shows brightfield images of TRAP, a mineral resorption enzyme, showed that coculture on DBP increased OC TRAP expression. On TCP, the presence of OBs did not affect OC TRAP expression (n=10). This indicates that, on DBP, the presence of OBs stimulated mineral resorption by OCs. (*P<0.05, **P<0.01).

FIG. 5A shows in homeostasis, 5-20% of the trabecular bone surface is actively remodeling and the rest is quiescent. An increase in actively remodeling bone surface alters metabolic regulation, and the resultant bone loss changes the trabecular bone morphology. This morphological change could compromise anatomical regulation of localized bone remodeling (Th: thickness; Sp: cavity space). FIG. 5B shows (i) DBP inserts were prepared by securing a 100-μm-thick DBP between two acrylic O-rings. Upper right: demonstration of the mechanical stability of DBP. (ii) A DBP insert is suspended above a resting-state DBP disk with bone lining cells in a well of a 24-well plate by means of a ring-shaped spacer. DBP inserts directed the osteoblasts to form an elongated morphology aligned with the underlying lamellar structure of the bone (right). FIG. 4C shows the trabecular bone organoid model consists of a DBP insert that has been activated by VD3 and PGE2 suspended over a DBP disk containing bone lining cells in a well of a 24-well plate. This juxtaposition of active and resting surfaces with a shared microenvironment allows for the development of in vivo-relevant gradients of stimulatory and suppressive molecules. FIG. 5D shows (i) osteoblasts cultured on DBP inserts acquired the bone lining cell secretory profile. (ii) Inserts stimulated with VD3 and PGE2 increased RANKL secretion in proportion to the surface area of the insert (n=5). FIG. 5E shows experimental design and schedule. FIG. 5F shows, to explore the impact of the ratio of active and resting surfaces, DBP with bone lining cells cocultured with BMMs and three sizes of DBP inserts containing activated osteoblasts. After 6 days of coculture, TRAP+ multinucleated osteoclasts and total area of ALP+ osteoblasts were measured (n=3). FIG. 4G shows, to explore the impact of the distance between the active and resting surfaces, the height of the spacer was varied. After 6 days of coculture, TRAP+ multinucleated osteoclasts and total area of ALP+ osteoblasts were measured (n=3). (*P<0.05, **P<0.01)

FIG. 6A shows DBP disks in a well plate scanned with fluorescent channels for TRAP, ALP, GFP, and DAPI. The resulting 218 multiplex images were stitched together to represent the entire surface of the DBP disk. FIG. 6B shows illustration of quantitative spatial imaging analysis for creating heat maps of counts of TRAP+ and multinucleated (>3) osteoclasts (OCs) (top) and areas of ALP+ and GFP+ osteoblasts (OBs) (bottom). FIG. 6C shows (i) to simplify statistical comparison, the DBP surface was discretized into seven concentric zones. The diameter of the activated insert is marked in shaded green. (ii) Activity levels in each region were plotted. The presented analysis is for the control. FIG. 6D shows representative heat maps of ALP+ OB activity and regional OB and OC activities with linear analysis to correlate localized bone remodeling cellular activity and paracrine signaling from five coculture experiments (n=3-5). The line drawn over the heat maps indicates the diameter of the stimulated DBP insert. FIG. 6E shows representative images of TRAP and ALP in central zone 1 and peripheral zone 6. FIG. 6F shows (i) representative multiplex images showing delineation of OCs and OBs, and (ii) quantitative comparison of ALP+ OBs that are and are not in direct contact with OCs in zones 1 and 6 (n=30). FIG. 6G shows proposed mechanism of localized trabecular bone remodeling regulation: Under normal homeostasis, bone lining cells secrete excess suppressive molecules and network with each other to localize the impact of stimulants and thus maintain overall bone mass and morphology (left). A decrease in resting-state cell mass and connectivity would impair feedback regulation and lead to excessive bone remodeling. Extended duration and expanded area of bone remodeling would change trabecular bone mass and morphology, which in turn would negatively influence localized bone remodeling activity (right). (*P<0.05, **P<0.01).

FIG. 9A shows acellular DBP with densely aligned collagen fiber bundles. FIG. 9B shows DBP after 1-week culture of osteoblasts with osteoblasts and osteoblast-secreted collagen fibers.

FIG. 11A contains optical profiler images. FIG. 11B shows quantitative measurement of surface roughness. (n=6) (*P<0.05)

FIG. 13A shows osteoclasts grown on TCP were larger and had greater cell-size distribution than those grown on DBP (n=20). FIG. 13B shows osteoclasts cultured on DBP and TCP had a similar ratio of number of nuclei to area (n=30). (*P<0.05, **P<0.01)

FIG. 16A shows summarized comparison of osteoblasts and bone lining cell phenotypes in four different conditions. FIG. 16B shows representative images in each condition.

FIG. 20A shows relative viability of osteoblasts cultured on static and vibrational culture for one week. FIG. 20B shows fluorescent calcein staining images after 3 and 9 days of static and vibrational mechanoculture (upper) and quantitative comparison of fluorescent signal (bottom) (*P<0.05).

FIGS. 21A to 21C show vibrational mechanoculture improves recapitulating mature phenotypes of OCY454 pre-osteocyte cell line. FIG. 21A shows that after one week, phase images of DBP cultured with OCY454 pre-osteocyte cell line in static and vibrational culture conditions. FIG. 21B is a fluorescent microscope image of OCY454 pre-osteocyte cell line on DBP for one week, exhibiting more mature osteocytes significantly on DBP under vibration. FIG. 21C shows increased sclerostin by OCT454 cells under vibration culture. (*P<0.01)

DETAILED DESCRIPTION

Figure 1A:
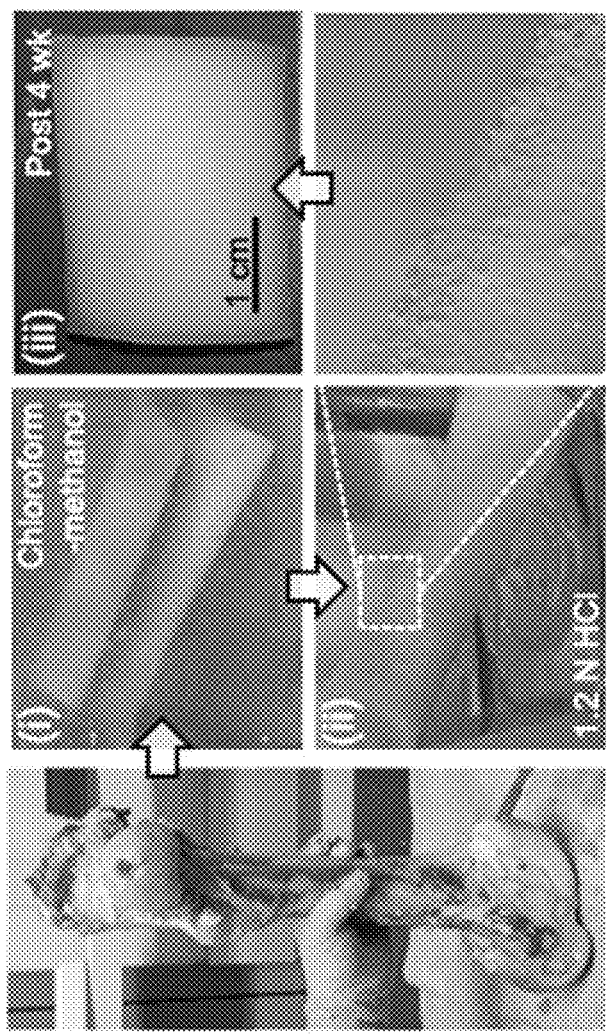
FIGS. 1A to 1I show development and characterization of demineralized bone paper (DBP), a novel biomaterial that emulates osteoid ECM.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

Demineralized Bone Paper

Disclosed herein is a demineralized bone paper (DBP) for use in producing 3D bone tissue grafts and assay systems when stacked together with bone-producing cells and/or factors.

The DBP can be produced from any mammalian bone, including a bovine or human bone. The bone can in some embodiments, be compact (cortical) bone. Therefore, in some embodiments, the DBP is derived from a long bone such as a femur or tibia of a mammal.

In some embodiments, the bones are first cut into chunks. Bone marrow can then be removed by centrifugation and muscle tissues removed mechanically. The chunks can then be cut into smaller pieces, centrifuged to remove marrow content, and treated in organic solvent to dissolve residual lipids and cell debris, e.g. a 1:1 chloroform-methanol or pure chloroform solution.

The cleaned bone pieces can then be submerged in a hydrochloric acid (HCl) solution to remove minerals from the bone matrix. To accelerate demineralization, a programmable cyclic pressure chamber can be used. For example, the chamber can be pressurized in a cyclic manner at 1-10 bar, preferably above 4 bar so long as the applied pressure does not break bone blocks, for about 6-48 hours, preferably about 24 hours. Cyclic pressures can, for example, involve an on/off interval of from 5 second to 10 minutes The demineralized outer layer of bone and a periosteal fibrous film can then be removed mechanically to ensure full exposure of the bone matrix. Incomplete removal of a periosteal fibrous film causes inefficient and inconsistent demineralization.

Subsequent rounds of cyclic hydrostatic pressure can then be applied until full demineralization is achieved, e.g. 24-72 hours, preferably about 48 hours. Finally, the demineralized bone pieces can be stabilized in deionized (DI) water. To determine the depth of demineralization, the processed bone pieces can be assayed with a rhodamine dye solution and/or radiographic imaging.

Once demineralized, the bone pieces can be embedded in a frozen section medium including optimum cutting temperature compound by centrifugation and frozen at −20° C. The frozen bone pieces can then be sliced into thin sections with a cryostat. Thickness of slices are preferably in the range of 10 to 1,000 μm. The sectioned demineralized bone matrix can then be soaked in sodium dodecyl sulfate solution or triton x-100 overnight to remove remaining cell debris. Decellularization can be confirmed, for example, by nuclear DAPI staining. Decellularized bone slices can then be washed with DI water and stored in about 70% ethanol at 4° C. At this stage, the biomaterial is referred to as DBP.

Culture

The DBP slices can be functionalized with bone-promoting cells and/or agents. In some embodiments, the DBP slices are used as a solid surface for culturing bone-promoting cells. For example, medium containing bone-promoting agents can be used to promote attachment and development of bone-promoting cells, such as osteoblasts, bone marrow stromal cells, mesenchymal cells, or any combination thereof. Once the DPB slices are adequately functionalized with cells and agents necessary to promote bone growth, the DPB slices can be stacked into a desired geometry and cultured again to promote development of a 3D bone tissue.

Kits

Also disclosed herein are systems and its containing the disclosed DBP. For example, in some embodiments, a system or kit is provided containing DBP slices and reagents for culturing bone-producing cells including osteoblasts, bone marrow stromal cells, mesenchymal stem cells, or skeletal stem cells on the DBP slices. In some embodiments, a user obtains bone-producing cells from a subject, cultures them on the DPB slices, stacks the slices to produce a 3D tissue graft, and then implants the graft into the subject. For bone tissue grafts, multi DBP with bone-producing cells can be layered in a customized 3D structure to create a patient specific size and shape of bone grafts. If 3D bone tissue grafts are thicker than 500 μm, conduit structure can be included in stacked DBP and of which surface can be coated with endothelial cells including human umbilical cord blood derived endothelial cells. This endothelial coated conduit networks can function as blood vessel in bone tissue to create thicker bone tissue grafts. In addition, different therapeutic molecules can be loaded in each layer of DBP to release target drugs in a sequential manner. For example, anti-inflammatory molecules at outer layers, vascular promoting agents in the middle, and cell proliferating agents in inner layers.

Microfluidic Bone Marrow Chip

Figure 19:
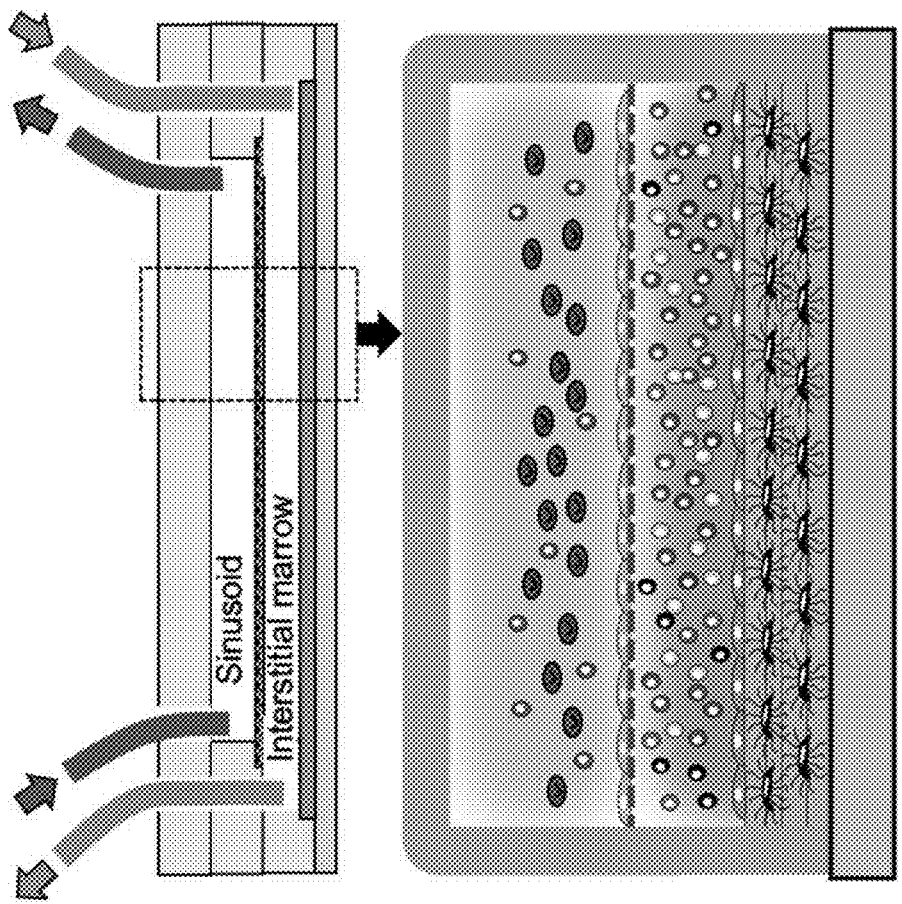
FIG. 19 shows an embodiment of a disclosed bone marrow chip design in exploded view (left), longitudinal cross-section (right-top), and vertical cross-section (right-bottom).
Figure 19:
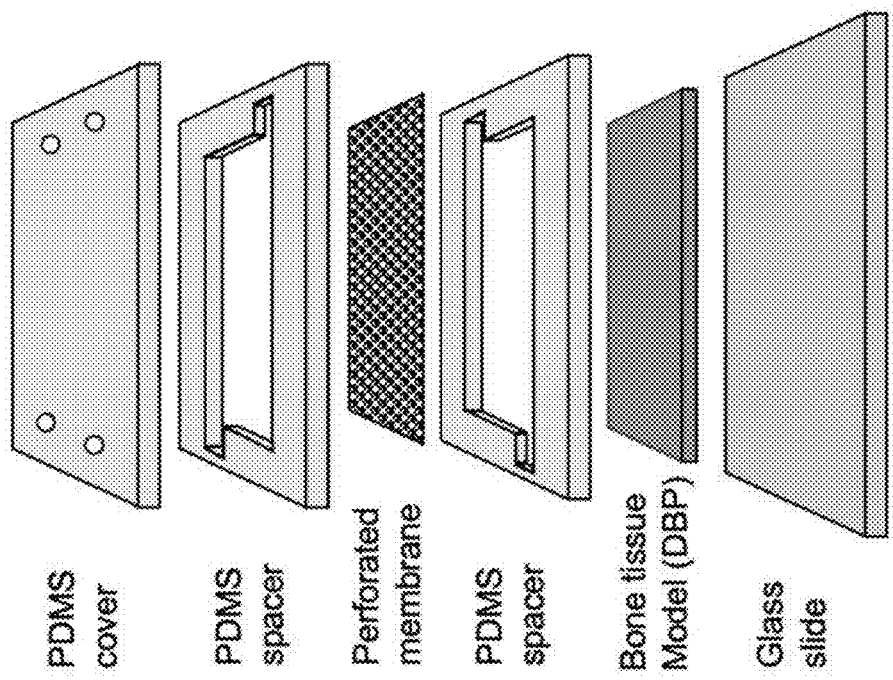

As shown in FIG. 19, also disclosed is a microfluidic bone marrow chip that involves the disclosed DBP and a semipermeable membrane that compartmentalize a microfluidic chip into sinusoid and interstitial chambers, wherein the interstitial chamber is in contact with the DBP. For example, the membrane can be a polydimethylsiloxane (PDMS) or polycarbonate track-etched (PCTE) membrane. In some embodiments, the sinusoid chamber is endothelized. For example, the sinusoid chamber can contain human umbilical cord blood cells, primary human endothelial cells, primary mouse endothelial cells, human and mouse endothelial cell lines, etc. In some embodiments, the interstitial chamber can be filled with hematopoietic cytokine containing media, methylcellulose media, or primary human and mouse bone marrow harvest, etc. The interstitial chamber can in some embodiments be periodically perfused with first medium. In some embodiments, the first medium contains hematopoietic growth factors, drugs (e.g., chemotherapeutics, osteogenic stimulants, vitamin D3, parathyroid hormones, prostaglandin E2). The sinusoid chamber can also be continually perfused with a second medium. In some embodiments, the second medium can contain blood plasma, whole blood, whole blood spiked with human or mouse cancer cells, chemotherapeutics, bone marrow targeting drug compounds, etc.

Methods

In some embodiments, the disclosed graft is produced by a method that involves first providing a plurality of individual demineralized compact bone slices. In some cases, the custom shape of bone graft can be manufactured by assembling standard size pre-made blocks to accelerate the manufacturing process.

In some embodiments, the compact bone slices have tailored shapes configured to produce a predetermined geometry when the slices are stacked. For example, the predetermined geometry can be patient-specific. The geometry can be determined by 3D scan or other such means, which can then be virtually "sliced" using software to identify shapes for each slice. Slicer software is currently available for 3D printing applications and could be adapted for this purpose. Once the shape is determined, compact bone slices can be cut into the desired shapes using a plotter cutter.

In some cases, a 3D negative mold can be 3D printed based on CT-scanned images of defected bone. Additive manufacturing can be applied to build custom size and shape of bone grafts by stacking, rolling, or folding demineralized compact bone slices seeded with bone-promoting cells in the 3D negative mold. To increase the thickness of cellularized 3D layered structure, conduit network can be included during additive manufacturing process. The surface of conduit can be coated with endothelial cells to function bone vascular networks.

Bone-promoting cells are next cultured on the individual demineralized compact bone slices in a medium comprising bone-promoting agents so as to produce seeded bone slices. The seeded bone slices are then stacked to produce a three-dimensional bone tissue graft. Bone-producing cells can attach on adjacent sides of the demineralized bone slices, which can function as biological glue to form a free-standing 3D bone tissue graft. Remineralization by bone-promoting cells can proceed after forming 3D bone tissue stacks. Therefore, the stacked slices can then be cultured in a medium configured to produce a three-dimensional bone tissue graft comprising a multi-layered lamellar bone structure. When stacked bone layers become too thick, e.g. thicker than 500 µm, conduit structure (250-500 µm diameter) can be included during additive manufacturing. The surface of conduit can be coated with endothelial cells. A bioreactor can be used to improve medium perfusion through 3D conduit structure to support cell proliferation and remineralization.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Trabecular Bone Organoid Model for Studying the Regulation of Localized Bone Remodeling Materials and Methods All chemicals and materials were purchased from Sigma-Aldrich or thermo fisher scientific unless specified. All animal procedures were approved by the institutional animal care and use committee of the university of Massachusetts Amherst. Experiments with and handling of mice were conducted in accordance with federal, state, and local guidelines.

Preparation of demineralized compact bovine bone blocks. Bovine femurs were obtained from a local slaughterhouse and cut into chunks. Bone marrow was removed by centrifugation and muscle tissues were removed with a scalpel. The chunks were then cut into smaller pieces and treated with a 1:1 chloroform-methanol solution to dissolve residual lipids and cell debris. The cleaned bone pieces were submerged in 400 ml 1.2 n hydrochloric acid (HCl) solution to remove minerals from the bone matrix. Under atmospheric pressure, the demineralization process of bovine compact bone (~1 cm thick) took more than 3 months with multiple rounds of HCL solution changes. To accelerate demineralization, a programmable cyclic pressure chamber was manufactured that consisted of an air-tight stainless-steel chamber (1 L) and a solenoid valve programmed for various on/off intervals by an Arduino controller. Two to three cleaned bone pieces were submerged in HCl solution (200 ml) in a glass beaker that was then placed in the pressure chamber. The chamber was pressurized (≤4 bar) with in-house compressed air, which was then released after a programmed delay. After a first round of 24 hours of on-off pressure cycle operation, the demineralized outer layer of bone and a periosteal fibrous film were removed with a razor blade to ensure full exposure of the bone matrix. Incomplete removal of a periosteal fibrous film causes inefficient and inconsistent demineralization. A second round of cyclic hydrostatic pressure was applied for 48 hours, the HCl solution was replaced, and the bone pieces were treated with another 48 hours of cyclic hydrostatic pressure. Finally, the demineralized bone pieces were stabilized in deionized (DI) water overnight. To determine the depth of demineralization, the processed bone pieces were soaked in rhodamine dye solution for 10 minutes and then cut into two pieces. The cross-sectional images were analyzed with ImageJ to determine the depth of dye penetration. Optimal pressure and on/off cycles were determined by orthogonally changing the pressure (1, 2, 3, and 4 bar) and on/off interval (10 seconds and 1, 5, and 10 minutes). The established protocol of 4 bar and 10-second on/off interval demineralized 1 cm thickness of compact bone piece within 1 week.

Radiographic imaging of demineralized bone blocks. Complete removal of mineral after the demineralization process was confirmed by radiographic imaging (Faxitron MX-20 X-ray cabinet) at 1 mA, 34 KV. Brightness of radiographs was quantitatively measured by ImageJ.

Preparation of DBP. Demineralized bone pieces were embedded in optimal cutting temperature medium, frozen at −20° C., and sliced into thin sections with a cryostat (Cryostar NX70). Thickness of slices was adjustable within the range of 10 to 150 µm; the 20 µm thickness was used in this study. The sectioned demineralized bone matrix was soaked in 8% sodium dodecyl sulfate solution overnight to remove remaining cell debris. Decellularization was confirmed by significantly reduced nuclear DAPI staining. Decellularized bone slices were then washed with DI water three times and stored in 70% ethanol at 4° C. At this stage, the biomaterial is referred to as DBP. More than 5,000 quality DBPs were produced from one bovine femur. DBPs were cut with biopsy punches into circular shapes to be placed in multiwell plates; 6-, 10-, 14-, and 16-mm-diameter DBPs were prepared for 96-, 48-, 24-, and 12-well plates, respectively. Prior to use, DBPs were sterilized with 70% ethanol for 15 minutes and then washed with phosphate-buffered saline (pbs) three times with 10-minute intervals.

Characterization of DBP

Mechanical properties. Different thicknesses of DBP (20, 50, and 100 µm) were cut into dog-bone shapes and gripped in a mechanical testing machine (ElectroForce 5500, TA instrument). The DBP was stretched at a rate of 0.4 mm/s at room temperature while applied tensile force and displacement of grips were continuously measured with XEI software (TA instruments) until failure. A stress-strain curve was plotted in excel from which young's moduli were determined.

Optical Transparency: To quantify absorbance, a circular hole (20 mm diameter) was made at the center of the plastic bottom of a 6-well plate with a laser cutting machine (Epilog laser). DBPs of various thicknesses (20, 50, and 100 µm) were placed over the hole, and a cover-glass slide was used as a control. The absorbance of DBPs and the glass slide was measured at a wavelength of 600 nm by a microplate reader (synergy 2, BioTek). Relative optical transparency was determined by setting the cover-glass slide absorbance as 100%.

Surface Morphology. Surface morphology of DBPs was observed optically under a tissue culture microscope. DBPs were dried and coated with gold by a sputter coating machine (CR108, Cressington) and imaged with SEM (Fei Magellan) for detailed characterization of surface morphology.

Biochemical intactness of collagen fibers. Collagen-hybridizing peptide (CHP) conjugated with fluorescein isothiocyanate was provided. For a positive control, damaged collagen matrix was prepared by submerging DBP in an 80° C. water bath. Before use, a CHP stock solution was incubated in the water bath at 80° C. for 5 minutes to dissociate coiled trimeric strands into monomeric strands. The heated solution was cooled on ice for 30 seconds. Intact and damaged DBPs were incubated overnight in 10 µm CHP solution at 4° C. The CHP bound on damaged collagen fibers was imaged under a fluorescence microscope (EVOS).

Retrieval and expansion of murine osteogenic cells. DsRed mice were obtained and GFP mice were obtained from Jackson Laboratory (003291). Mice aged 6 to 12 weeks were used for the study. Femurs and tibias were harvested intact and the surrounding connective tissues were removed. After the epiphyses were removed, the open-ended long bones were placed in 0.5-ml microcentrifuge tubes with holes punched in the bottom with a 26-gauge needle, and those tubes were inserted in 1.5-ml microcentrifuge tubes with the cap closed. During centrifugation at 10,000×g for 30 seconds, the entire bone marrow was released into the 1.5 ml tubes. The marrow-emptied long bones were gently cut into 1 mm to 2 mm lengths with a scalpel. These bone chips were placed in a T25 flask with 3 ml of digesting medium composed of α-minimum essential medium (α-MEM), 1% penicillin/streptomycin (PS), and 800 units of collagenase. After 1 hour of incubation at 37° C., the digesting medium was replaced with expansion medium composed of α-MEM supplemented with 1% PS and 10% fetal bovine serum (FBS). Osteogenic cells migrated out from bone chips and proliferated on TCP. Once 80% confluency was achieved, the cells were detached with 1% trypsin/ethylenediaminetetraacetic acid (EDTA) and subcultured in T175 flasks for further expansion. Cells were cultured at 37° C. in a humidified atmosphere containing 5% $CO_2$. Cells used for experiments were subcultured less than five times.

Osteoblast differentiation. Expanded osteogenic cells were cultured in osteoblast differentiation medium composed of α-MEM supplemented with 1% PS, 10% FBS, 10 mm β-glycerophosphate, and 200 μm L-ascorbic acid.

Osteoblast Functional Assays:

Osteogenic cell morphology and alignment. The osteoblasts were cultured for 1 week in osteogenic differentiation medium and fixed with 4% paraformaldehyde. Cytoskeletal actin filaments and nuclei were stained with phalloidin conjugated with Alexa Fluor 488 and 2-(4-amidinophenyl)-6-indolecarbamidine dihydrochloride (DAPI), respectively. Confocal microscopy (Zeiss cell observer SD) was used for imaging. Cell alignment angles were measured with the angle tool function of ImageJ. Cell alignment angles on TCP and DBP were measured with respect to the horizontal line and the average of collagen alignment of DBP, respectively. The 0° angle was set based on collagen alignment angle of DBP. A total of 100 measurements from 10 different samples were used to generate a circular diagram that was produced in MATLAB.

Osteogenic migration under long-term fluorescent time-lapse imaging. Endogenous GFP and DsRed fluorescence of osteogenic cells was detected with an inverted fluorescent microscope with a 10× objective lens (Lumascope 720, Etaluma) that operates inside of a $co_2$ incubator. Quantitative cell migration analysis was conducted by processing obtained images using TrackMate in ImageJ. Time-lapse movies were prepared with ImageJ.

Collagen deposition and alignment. A resonant scanning multiphoton microscope (Nikon A1MP) was used to image collagen fibers deposited by osteoblasts via second harmonic generation with a 25× objective lens. Collagen fibers were excited at 810 nm. Alignment angles of individual collagen fibers were measured with the angle tool function of ImageJ. Collagen alignment angle on TCP and DBP were measured with respect to the horizontal line on TCP and the average of collagen alignment on DBP. A total of 100 measurements from 10 different samples were used to generate a circular diagram.

Mineral deposition. Mature osteoblasts were cultured on TCP and DBP for up to 3 weeks with osteogenic differentiation medium. At the end of the experiment, cells were fixed with 4% formaldehyde for 5 minutes, washed three times with DI water, and stained.

Alizarin red mineral staining. Fixed samples were stained with alizarin red (American MasterTech) for 30 minutes and washed with di water until the washing solution appeared clear. Mineral stained with alizarin red was imaged with an optical microscope (EVOS) with a 10× objective lens. Deposited mineral was quantified by solubilizing alizarin red in 10% acetic acid for 1 hour and measuring the absorbance of the solution at 405 nm with a microplate reader (BioTek).

Fluorochrome calcein mineral staining. Because calcein emits green fluorescence, osteogenic cells were derived from DsRed mice. Fixed samples were stained with 50 μm calcein solution. The fluorescence of calcein and DsRed osteogenic cells was imaged under confocal microscopy with 10× and 20× objective lenses.

Chemical remineralization of DBP in simulated body fluid. To prepare 1 L of 10× simulated body fluid (SBF) solution, 58.43 g (1 M) of NaCl, 0.373 g (5 mm) of KCl, 3.675 g (25 mm) of $CaCl_2 \cdot 2H_2O$, and 1.016 g (5 mm) of $MgCl_2 \cdot 6H_2O$ were dissolved in 600 ml DI water (solution 1). In a separate glass beaker, 0.42 g (10 mm) of $Na_2HPO_4$ was dissolved in 30 ml of DI water (solution 2). Solution 2 and HCl were added to solution 1 dropwise to maintain pH below 4 to avoid calcium precipitation. DI water was also added to bring the final volume up to 1 L while maintaining a pH of 4. For calcium precipitation, a small amount of $NaHCO_3$ was added in the 10×SBF solution to increase ph. For remineralization, DBP was submerged in the 10×SBF solution immediately after adding $nahco_3$ and incubated at 37° C. for 5 hours.

Surface Characterization:

Imaging surface morphology. SEM was used to obtain high-resolution surface morphology of DBP, osteogenic cells, and deposited minerals. Osteogenic cells were fixed with 2.5% glutaraldehyde and rinsed with DI water. The fixed cells were dehydrated in sequential graded ethanol solution (50, 70, 80, 90, 95, and 100%) for 10 minutes each. The cells were dried at room temperature with hexamethyldisilazane. Before imaging, samples were coated with gold with a sputter coating machine.

Measuring surface roughness. Remineralized DBPs were heated at 500° C. for 5 hours to thermally decompose the organic components. The remaining mineral layers were analyzed by an optical profiler (Nexview, Zygo) that visualized 3D surface morphology and quantitatively presented surface roughness.

Characterization of bone lining cells. DBP was seeded with $1 \times 10^6$ osteoblasts per square millimeter. After 1 week of culture with differentiation medium, osteoblasts fully covered the surface and exhibited the bone lining cell phenotype as characterized by the following methods:

Immunofluorescent staining of Ki67. Osteoblasts were fixed with 4% paraformaldehyde for 5 minutes at room temperature and washed three times with PBS. The fixed cells were incubated in PBS containing 0.1% triton x-100 for 10 minutes and washed three times with PBS. For blocking, the cells were incubated with 10% goat serum and 1% bovine serum albumin (BSA) in pbs for 2 hours at room temperature. A primary rabbit anti-mouse Ki67 antibody (1:200 dilution in the blocking solution) was applied to the sample and incubated overnight at 4° C. After three washes with PBS, a secondary goat anti-rabbit antibody conjugated with Alexa Fluor 647 (1:200 dilution in the blocking solution) was applied and incubated for 1 hour at room temperature. After three washes with pbs, a DAPI solution (100 µl of 10 ng/µl) was added before imaging. Images were obtained with fluorescence and confocal microscopy.

Bone surface healing assay. The cell surface was scraped with a sterilized acrylic rod (0.5 mm diameter). Time-lapse fluorescent imaging of the scratched area was conducted for 72 hours at 30-minute intervals (LumaScope 720) in a $CO_2$ incubator. Recovery of the scratched area by awakened bone lining cells was quantified with ImageJ. Transiently increased osteogenic cell migration rates were measured with TrackMate in ImageJ.

Osteoblast phenotypic switching assay. Osteoblasts cultured on DBP with differentiation medium acquired a bone lining cell phenotype and reached full confluence after 2 weeks. The DBP with confluent bone lining cells was transferred to a T25 flask and 3 ml of α-MEM with 800 units of collagenase ii was added. After 1 hour of incubation at 37° C., the degraded DBP left behind mineralized fragments. The collagenase solution was carefully removed, and 5 ml of expansion medium was added. Osteogenic cells migrated out of the mineralized parts and culture-expanded on TCP. Expanded osteoblasts on TCP were detached with trypsin and EDTA and reintroduced on DBP to reinduce the bone lining cell phenotype, which is considered one cycle of this osteoblast phenotypic switching assay. In each cycle, the time to reach 80% confluency on TCP and the amount of mineral deposited in the 2-week culture on DBP were determined. We repeated three cycles of this phenotypic switching assay.

Characterization of GAP junction communication among osteogenic cells on DBP:

Immunofluorescent staining of connexin 43. Osteoblasts on DBP were fixed with 4% paraformaldehyde for 5 minutes at room temperature. The cells were then washed three times with PBS. Washed cells were incubated for 10 minutes with PBS containing 0.1% triton x-100 and then washed three times with PBS. For the blocking step, the cells were incubated with 10% goat serum and 1% BSA in PBS for 2 hours at room temperature. Primary and secondary antibodies were diluted 1:50 and 1:200 in blocking solution, respectively. The cells were incubated overnight with rabbit anti-mouse connexin 43 antibody at 4° C. After washing three times with pbs, goat anti-rabbit antibodies with Alexa Fluor 647 were added to samples and incubated for 1 hour at room temperature. After washing with pbs three times, phalloidin conjugated with Alexa Fluor 488 and DAPI (100 µl of 10 ng/µl) was added. Fluorescence imaging was conducted with a confocal microscope.

Time-lapse fluorescence imaging of $Ca^{2+}$ influx. For gap junction-mediated $Ca^{2+}$ imaging, osteoblasts on DBP were incubated in calcium-free PBS for 5 hours and then loaded with 5 µm fluo-4 am in calcium-free PBS. After 1-hour incubation, the osteoblasts were washed with calcium-free PBS three times. Time-lapse fluorescent imaging of $Ca^{2+}$ influx under potassium stimulation was performed with a confocal microscope with a 20× objective lens at 0.5 seconds per frame for 5 minutes (cell observer SD). The average pixel intensity of fluorescence in each individual cell was quantified with ImageJ.

Isolation of murine bone marrow mononuclear cells. Femoral and tibial bones were harvested and the bone marrow was isolated as mentioned above. On average, more than $2 \times 10^7$ bone marrow cells were harvested from each mouse. Isolated whole bone marrow cells were plated on TCP with expansion medium supplemented with macrophage colony stimulating factor (M-CSF; 20 ng/ml). After 3 days of culture, floating bone marrow mononuclear cells (BMMs) were separated from adherent stromal cells for osteoclast differentiation experiments.

Osteoclast differentiation. BMMs were seeded on TCP, remineralized decellularized DBP (RD-DBP), and DBP with osteoblasts with osteoclast differentiation medium composed of α-mem supplemented with 10% FBS, 1% PS, receptor activator of NF-κB ligand (RANKL; 40 ng/ml), and M-CSF (20 ng/ml). Osteoclast differentiation medium was replaced every 3 days.

Osteoclast Characterization and Functional Assays:

Osteoclast morphology and size. BMMs cultured in osteoclast differentiation medium were fixed with 4% paraformaldehyde. Actin filaments and nuclei were stained with phalloidin conjugated with Alexa Fluor 488 and DAPI, respectively. Confocal microscopy (cell observer SD) was used to visualize osteoclast-specific actin-ring structure with a nucleus. The number of nuclei in a single osteoclast was counted manually in ImageJ, and cells with more than three nuclei were considered to be mature osteoclasts. The size of an osteoclast cell body was calculated from the average vertical and horizontal diameters.

Osteoclast migration under long-term fluorescent time-lapse imaging. Endogenous GFP or DsRed fluorescence of BMMs was detected with a 10× objective lens (Lumascope 720). The resulting images were analyzed with TrackMate in ImageJ to quantify cell migration, and time-lapse movies were prepared in ImageJ.

Osteoclast mineral resorption confirmed by SEM. Scanning electron microscopy (FEI Magellan 400) was used to confirm mineral resorption by osteoclasts. Osteoclasts emerged after 7 to 10 days of culture in osteoclast differentiation medium and were fixed with 2.5% glutaraldehyde and rinsed with DI water. The cells were then dehydrated in ethanol and dried at room temperature with hexamethyldisilazane. Before SEM imaging, samples were coated with gold.

Osteoblast and osteoclast coculture experiments. Osteogenic cells retrieved from GFP mice were cultured on DBP in a 48-well plate with osteoblast differentiation medium for 1 week to induce a mature bone lining cell phenotype. Then $1 \times 10^6$ BMMs retrieved from DsRed mice were introduced into the wells in stimulation medium composed of α-MEM, 10% FBS, 1% PS, PGE2 (1 µm) and VD3 (10 nm).

Functional Characterization of Osteoblast and Osteoclast Coculture:

Determining OPG and RANKL secretion by enzyme-linked immunosorbent assay. OPG and RANKL proteins produced by osteoblasts were measured in conditioned media with an ELISA kit (R&D systems). Media samples were taken over the culture period and diluted 1:5 in reagent diluent to bring OPG and RANKL concentrations within the detection range of the assay. The assay was performed according to the manufacturer's instructions.

Time-lapse fluorescent imaging of the coculture and quantitative imaging analysis. GFP osteoblasts and DsRed-osteoclast precursor cells were cultured together in stimulation media. These cells were observed through a 10× objective lens with a fluorescence microscope (Lumascope 720) operated in a $CO_2$ incubator. Time-lapse movies were prepared in ImageJ.

Trap activity. cells were fixed in 4% formaldehyde and washed three times with DI water. Osteoclast differentiation was evaluated with a trap detection kit (387a, Sigma-Aldrich) according to the vendor's protocol. Stained cells were observed with an optical microscope.

Alkaline phosphatase activity. Cells were fixed with 4% paraformaldehyde for 5 minutes and then washed with di water three times. Alkaline phosphatase (ALP) detection kits (86c, Sigma-Aldrich) were used to analyze the ALP activity of osteoblasts. The staining was performed according to the vendor's protocol. Stained cells were observed with an optical microscope.

Preparation of DBP inserts. Inner and outer O-rings were fabricated to interlock around DBP disks. The rings were designed in adobe illustrator and cut with a laser cutting machine from 1-mm-thick acrylic plates. The outer O-rings were slightly larger than the DBP circles and had four side-bars to center the DBP insert in the well. The diameters of the inner O-rings were 6 mm, 10 mm, and 14 mm. Ring-shaped spacers were cut from acrylic plates with 0.5 mm, 1.5 mm, and 4.5 mm thicknesses. Fabricated O-ring inserts and spacers were sterilized with 70% ethanol before use in cell culture. Sterilized DBP-rings were washed with pbs three times and placed in a 24-well plate before cell seeding.

Experimental setup for trabecular bone organoid model with a DBP insert. For the resting state, $1.5 \times 10^5$ osteoblasts were seeded on DBP (16-mm diameter) in a 24-well plate and cultured with differentiation medium for more than 1 week. For the activated state, $1.5 \times 10^5$, $7 \times 10^4$, and $2 \times 10^4$ osteoprogenitor cells were first seeded on 15 mm, 12 mm, and 8-mm-diameter DBP circles, respectively. The osteoblast seeded DBPs were gripped by the two concentrically assembled O-rings and cultured more than 7 days with differentiation medium. Bone lining cells on DBP inserts were stimulated with VD3 and PGE2 for two rounds of 3 days each. Next, $1 \times 10^6$ BMMs were added to each well. Stimulated DBP inserts were transferred to the 24-well plates with the osteoblasts facing the bottom of the plate. The distance between the resting and activated DBP surfaces was controlled with 0.5 mm-, 1.5 mm-, and 4.5 mm-thick, ring-shaped spacers. During coculture, the activated DBP insert was replaced with a newly activated DBP insert every 3 days to maintain the profile of secretory molecules from activated osteoblasts. Multiplex immunofluorescent staining was performed after 6 days of coculture.

Multiplex immunofluorescent staining and imaging. Osteoblasts and BMMs retrieved from GFP mice were used to perform multiplex imaging. After osteoblasts and osteoclasts were cocultured in the trabecular bone organoid model, cells on DBPs in the 24-well plate bottom were fixed in 4% paraformaldehyde for 5 minutes at room temperature and washed three times with PBS. The fixed cells were incubated for 10 minutes with PBS containing 0.1% Triton x-100 and washed with pbs three times. The samples were blocked with 10% donkey serum and 1% BSA in pbs for 2 hours at room temperature. Primary goat anti-mouse alp and rabbit anti-mouse trap antibodies were diluted 1:200 in blocking solution and added on the samples. After overnight incubation at 4° C., the cells were washed three times with pbs. Secondary donkey anti-goat antibodies conjugated with Alexa Fluor 568 and donkey anti-rabbit secondary antibodies conjugated with Alexa Fluor 647 were diluted 1:200 in blocking solution and added to samples. After 1-hour incubation at room temperature, the cells were washed with pbs three times. Before imaging, DAPI solution was added (200 µl of 10 ng/µl). The entire surface of multiplex imaging samples was scanned with fluorescence and confocal microscopes with 10× objective lenses.

Quantitative image analysis algorithm of multiplex immunofluorescent images. TRAP$^+$ multinucleated osteoclast number and ALP$^+$ osteoblast areas on DBP placed in a 24-well plate were quantified from multiplex immunofluorescent images with CellProfiler. Automatic quantification was validated by comparing the results against manually obtained data. For total analysis, osteoclast number and ALP$^+$ osteoblast area were averaged from three independent experiments. Fold change of osteoclast number and percentage of ALP$^+$ osteoblast area were calculated based on the results from unstimulated control. For regional analysis, the bottom DBP was discretized into seven concentric regions in which TRAP$^+$ osteoclast number and ALP$^+$ osteoblast area were calculated. Fold change was determined by comparing the results of matching control experiment. For the characterization of alp reduction of osteoblasts in contact with osteoclasts, trap$^+$ osteoclasts were identified. Then osteoblasts that were and were not in direct contact with osteoclasts were manually identified. Finally, ALP expression area of the selected osteoblasts was quantified using ImageJ.

Statistics. All measurements were collected in at least triplicate and expressed as means±standard deviations. P values were calculated using the t test and one-way analysis of variance (ANOVA) with post hoc Bonferroni test in SPSS (IBM). Analysis of variance was employed to assess significance, with P values less than 0.05 (*) and 0.01 (**).

TABLE 1

Summary of in vitro osteoblast and osteoclast assays. (single layer of DBP)

| Materials Transparency | TCP High | TCP + collagen High | TCP + HA NPs High | TCP + Bone chips Partially opaque | TCP + Bone disk Opaque | TCP + DBP Semi-transparent | TCP + RDBP Semi-transparent |
|---|---|---|---|---|---|---|---|
| Osteoblast assay | Yes (lengthy) | Yes (lengthy) | — | — | — | Yes (rapid) | — |
| Osteoclast assay | Yes (not functional) | Yes (not functional) | Yes (functional) | Yes (functional) | Yes (functional) | — | Yes (functional) |
| Co-culture assay | — | — | — | — | — | Yes (functional) | — |

TCP: Tissue Culture Plastic
DBP: Demineralized Bone Paper
HA NPs: Hydroxyapatite Nanoparticles
RDBP: Remineralized Decellularized Bone Paper Results
DBP Effectively Simulates the Trabecular Osteoid.

Figure 1B:
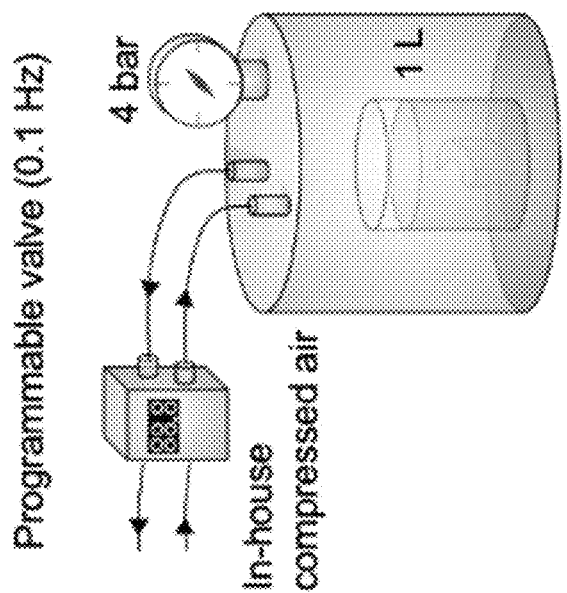
Figure 1C:
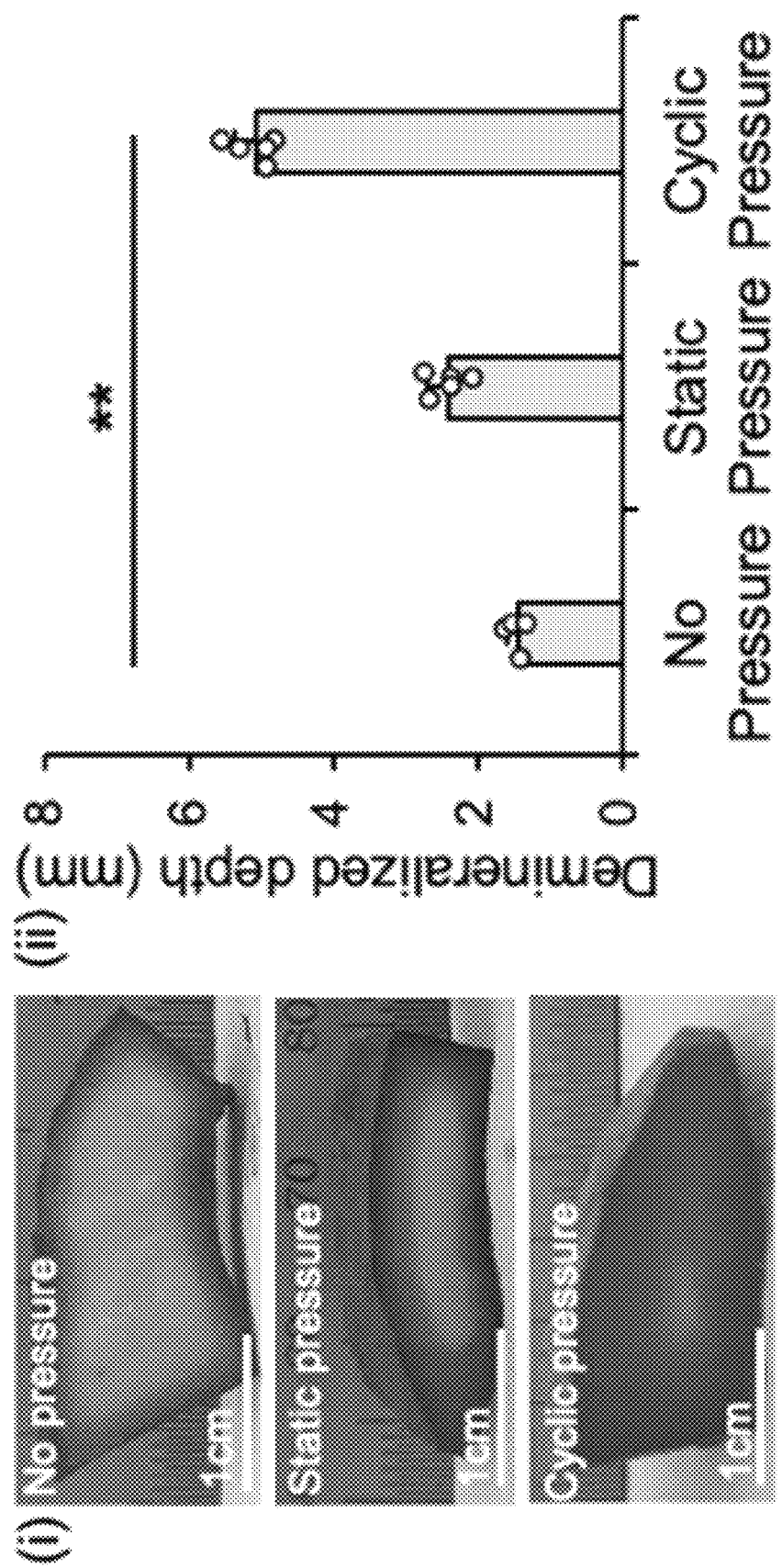
Figure 1D:
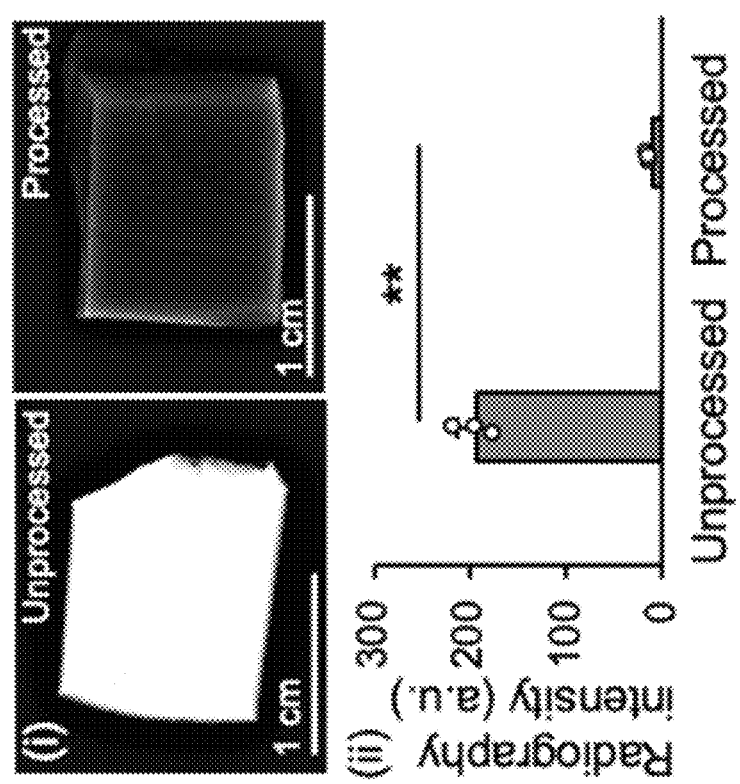
Figure 7:
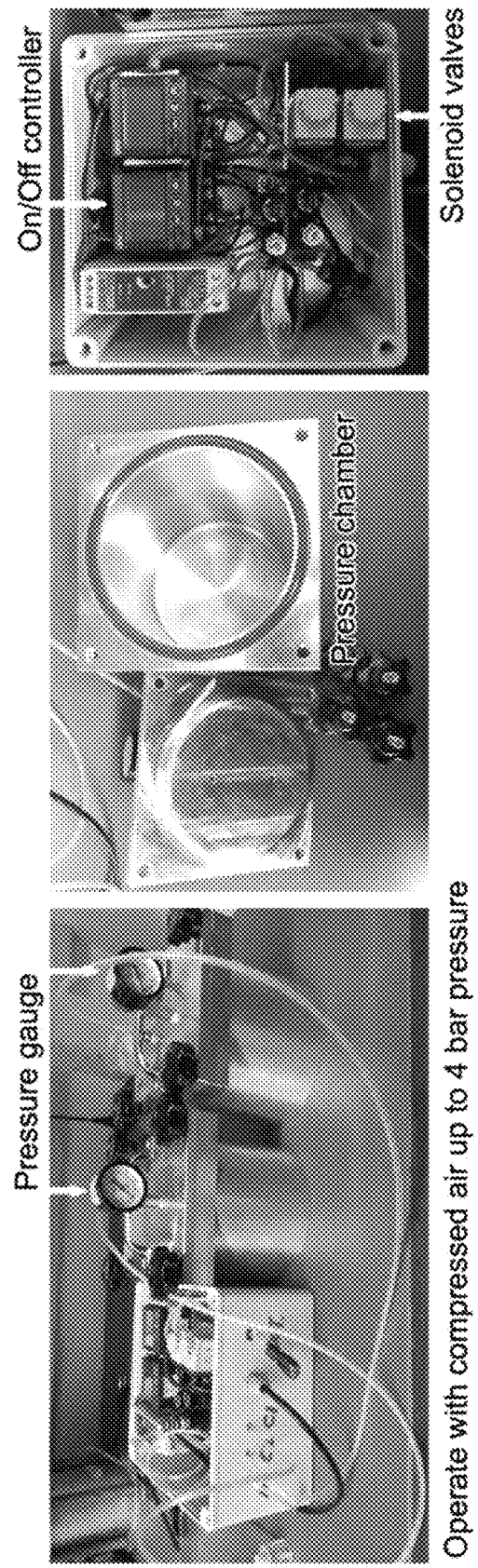
FIG. 7 shows programmable pressure chambers for rapid bone demineralization.
Figure 8B:
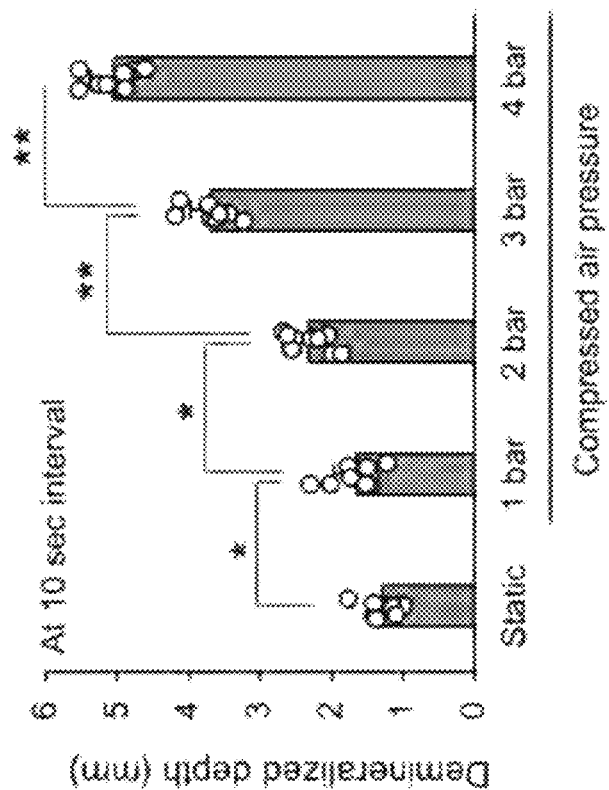
FIGS. 8A and 8B show demineralization depth in varying on-off cycles and compressed air pressures. Cleaned bovine compact bone blocks were demineralized in programmable pressure chamber for 48 hours under four different on/off cycles (FIG. 8A) and four compressive air pressures (FIG. 8B). (n=10) (*P<0.01, **P<0.001).
Figure 8A:
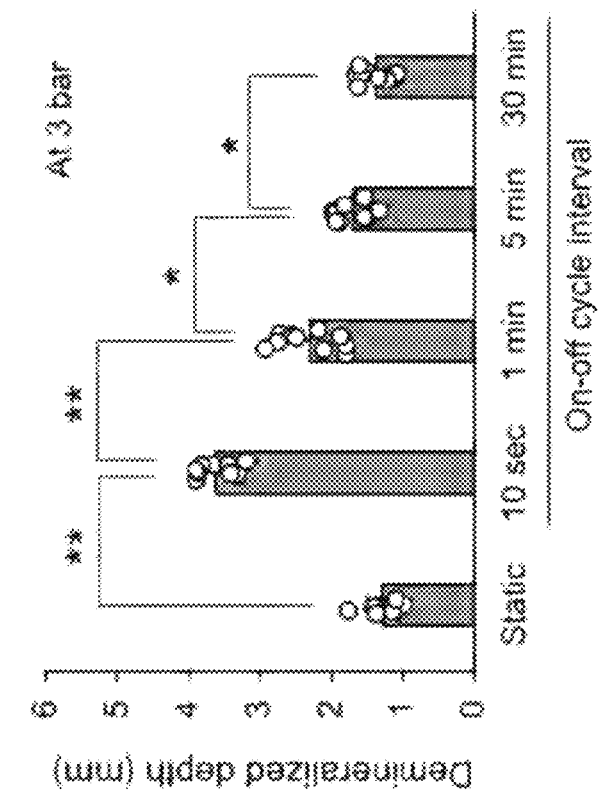

To reproduce the bone remodeling process in a controlled and analytical manner, a biomaterial was developed that mimics the dense structural collagen matrix of the unmineralized osteoid with thin sections of demineralized bovine compact bone. First, a method was established to rapidly demineralize bone matrix. Bovine femurs were cut into 4 cm to 5 cm blocks, marrow and connective tissue were removed, and the fat dissolved in methanol and chloroform. Then the blocks were submerged in 1.2 N hydrochloric acid to dissolve bone mineral. The outer layer of bone turned semitransparent after 5 days, but demineralization progressed little over the next 4 weeks because diffusion through the dense collagen matrix was limited (FIG. 1A). Under the hypothesis that cyclic hydrostatic pressure can promote the demineralization process, a programmable pressure chamber operated with compressed air was devised (FIGS. 1B, 7). Demineralization depth increased when hydrostatic pressure was applied and increased further when hydrostatic pressure was applied in a cyclic pattern. The most effective operating condition was 4 bar pressure with a 10-second on-off interval. This process demineralized 5.1±0.3 mm compact bone matrix in 5 days (FIGS. 1C, 8). Radiographic images confirmed that the processed bone tissue was fully demineralized (FIG. 1D).

Figure 1E:
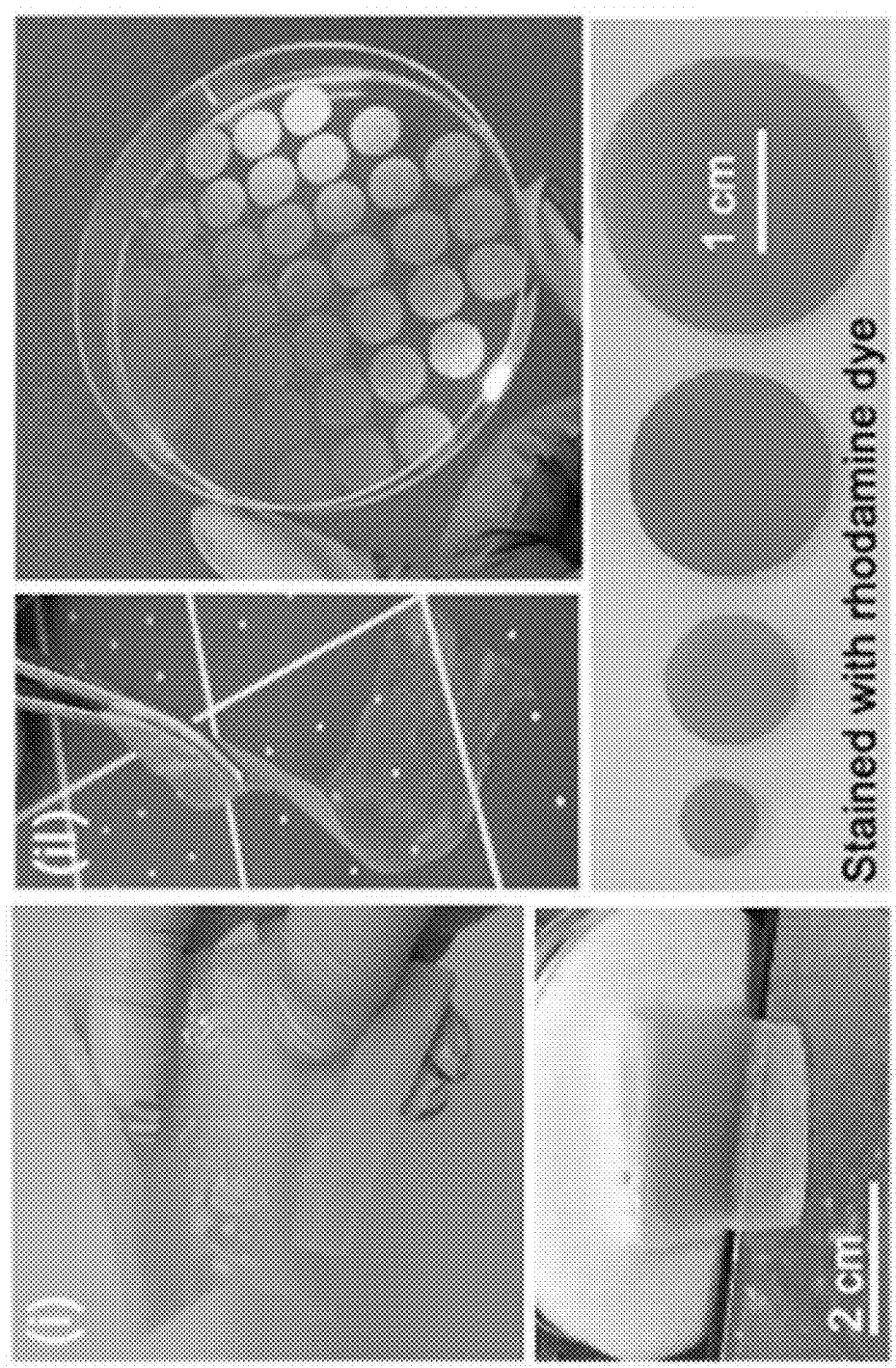
Figure 1F:
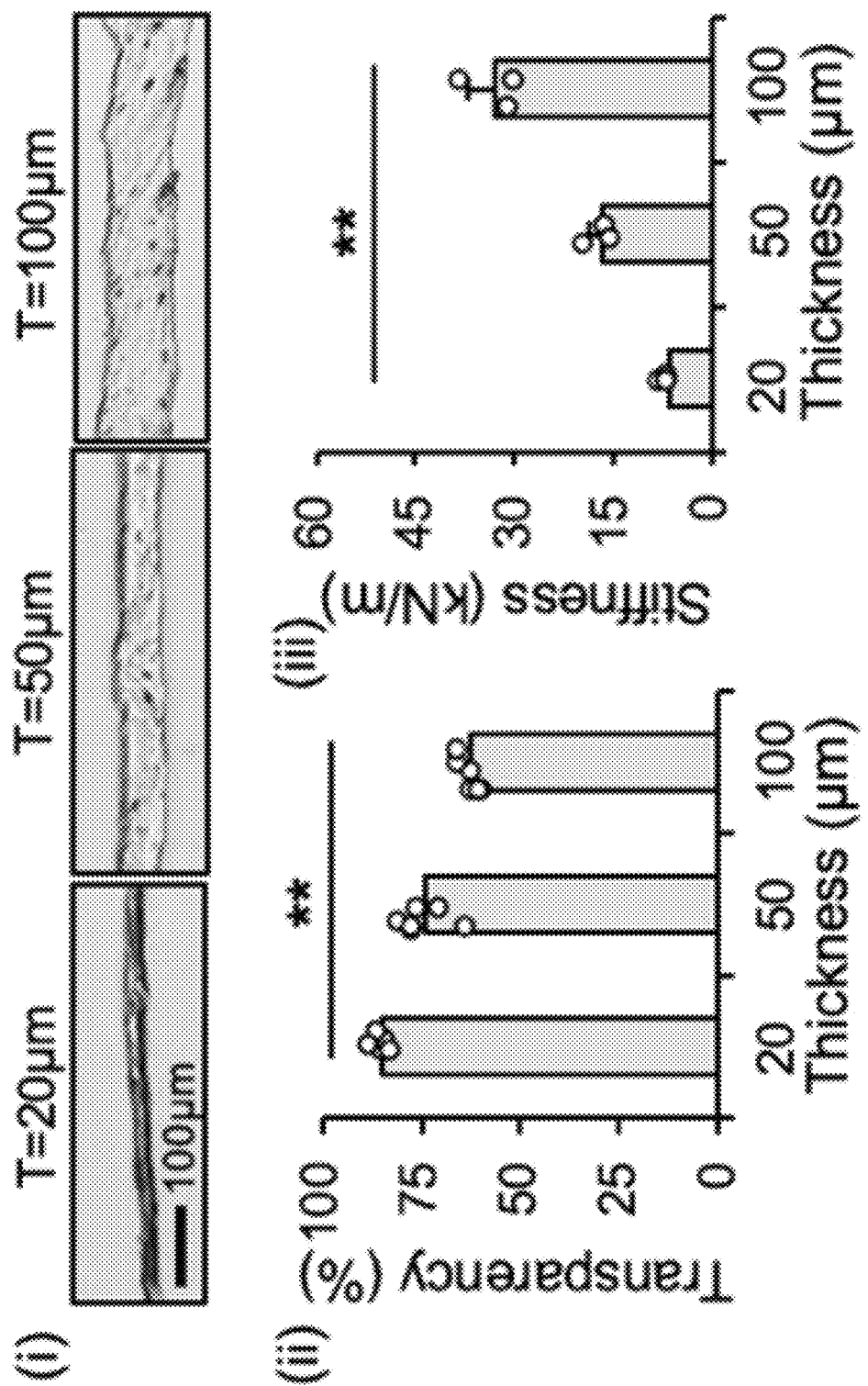
Figure 1G:
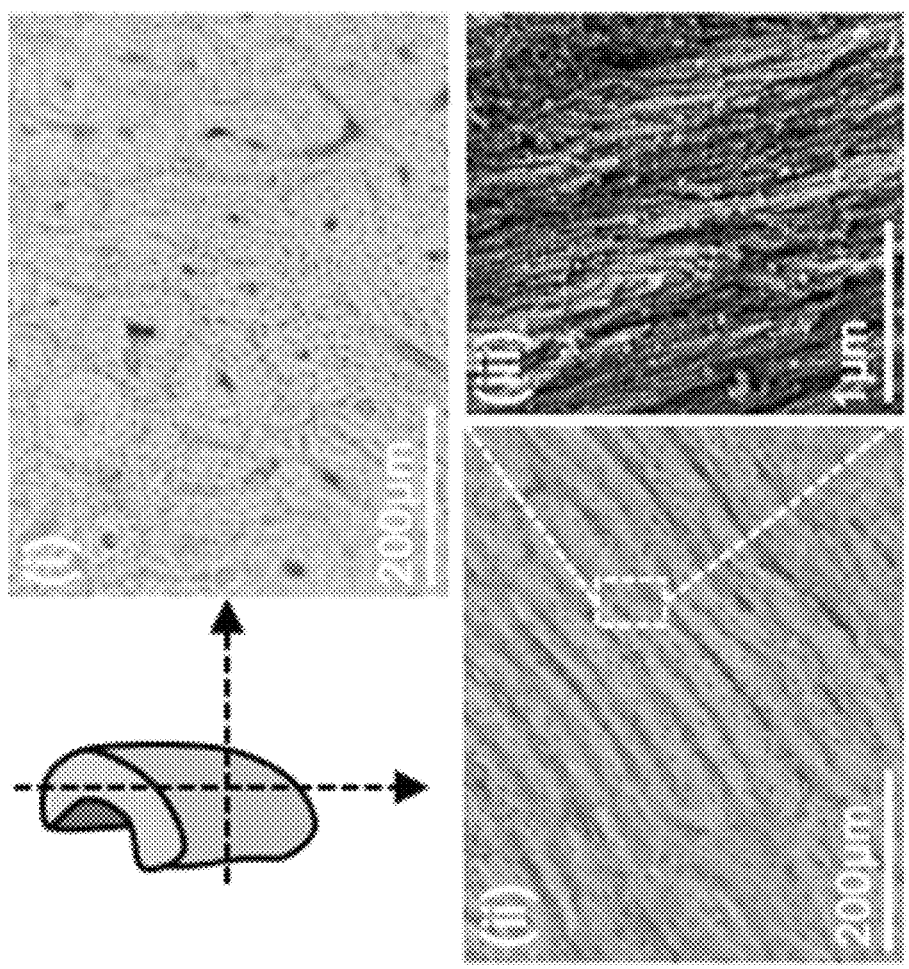
Figure 1H:
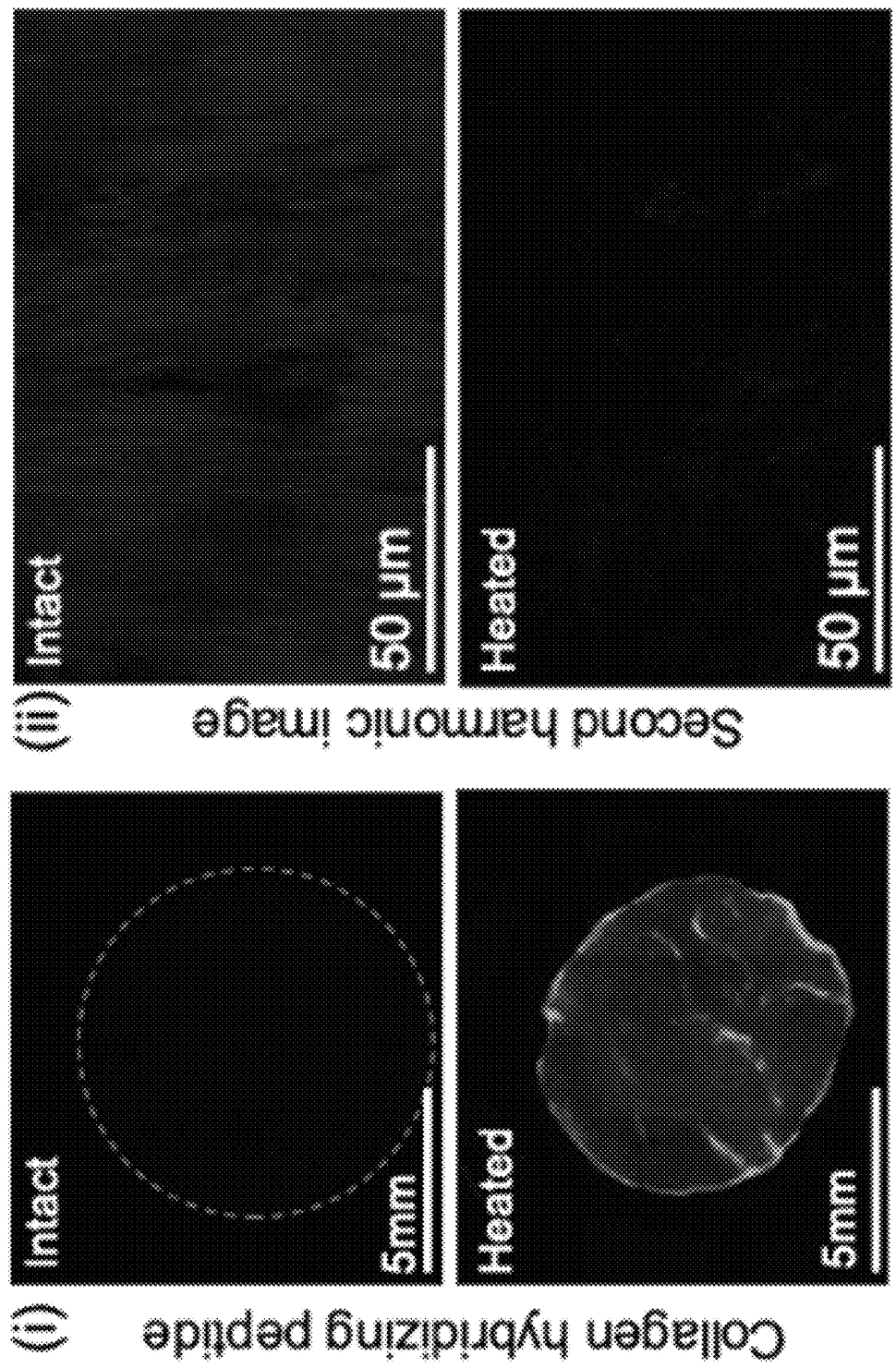
Figure 1I:
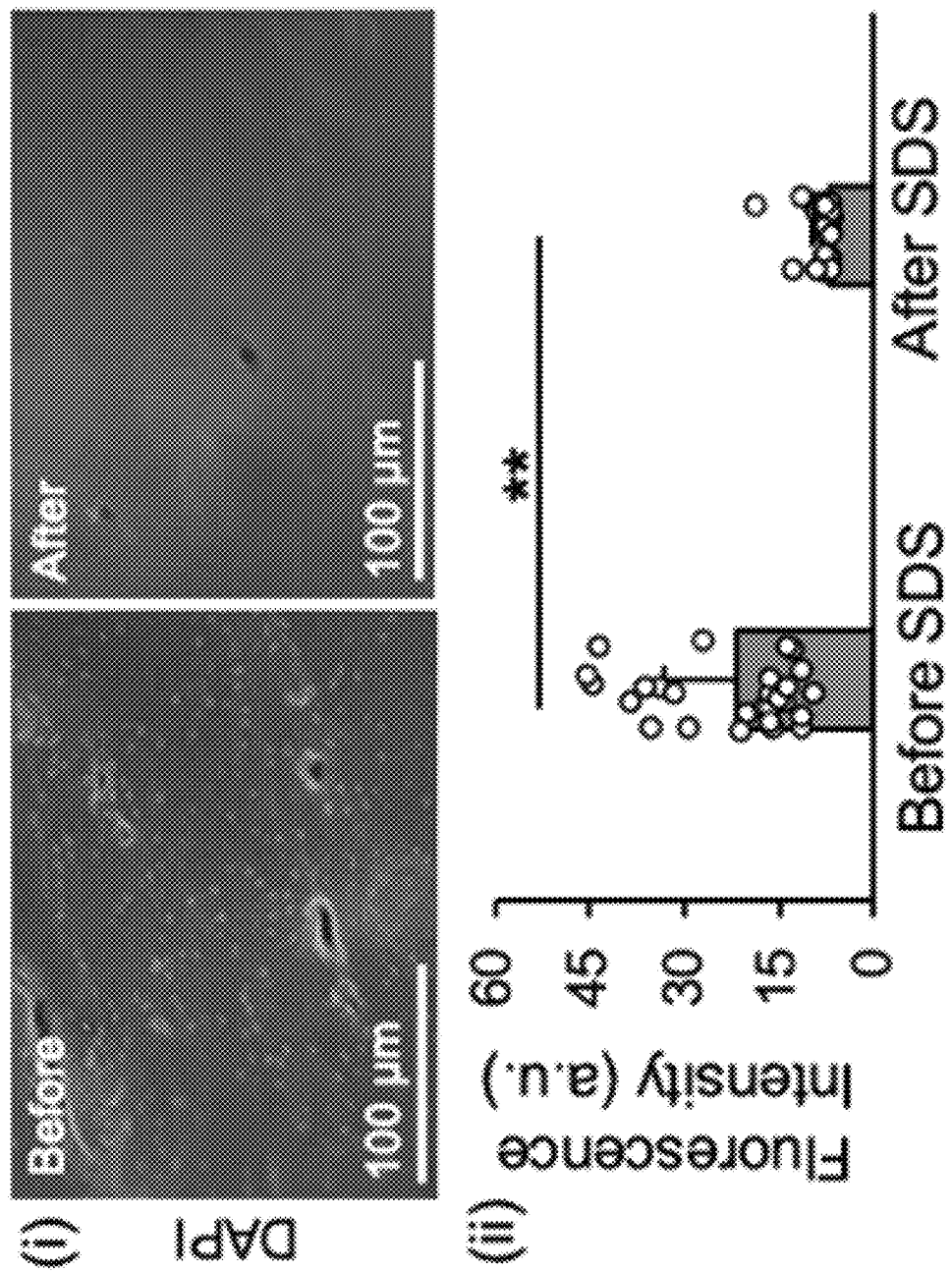

A demineralized compact bone block was then cryosectioned to generate 3×4 cm slices and the slices biopsy-punched to obtain disks that will fit in multiwell plates (FIG. 1E). 20 μm was shown to be a practical thickness that provides 80% of the light transmittance of tissue culture plate (TCP) yet retains sufficient mechanical durability for handling (stiffness: 6.5±0.4 kPa) (FIG. 1F). Transmission micrographs confirmed a well-preserved bony ECM structure that exhibited distinct morphology depending on sectioning direction: vertical sections had parallel lamellar structure and transverse sections had concentric lamellar layers. Scanning electron micrographs (SEM) showed densely aligned collagen fiber bundles (FIG. 1G). Collagen-hybridizing peptides that specifically bind to damaged collagen fibrils (Bennink, L L, et al., Biomaterials 2018 183: 67-76) did not bind to demineralized bone slices. In addition, multiphoton second harmonic imaging that visualizes intact fibrillar collagen structure (Chen, X, et al. Nat Protoc 2012 7:654-669) revealed aligned collagen fibers (FIG. 1H). These results indicate the preserved biochemical integrity of the collagen. Finally, residual cellular materials were removed from demineralized bone sections by treating with sodium dodecyl sulfate (FIG. 1I). These sheets of demineralized bone matrix were named "DBP."

DBP Directs Rapid and Structural Mineralization by Osteoblasts.

Figure 2A:
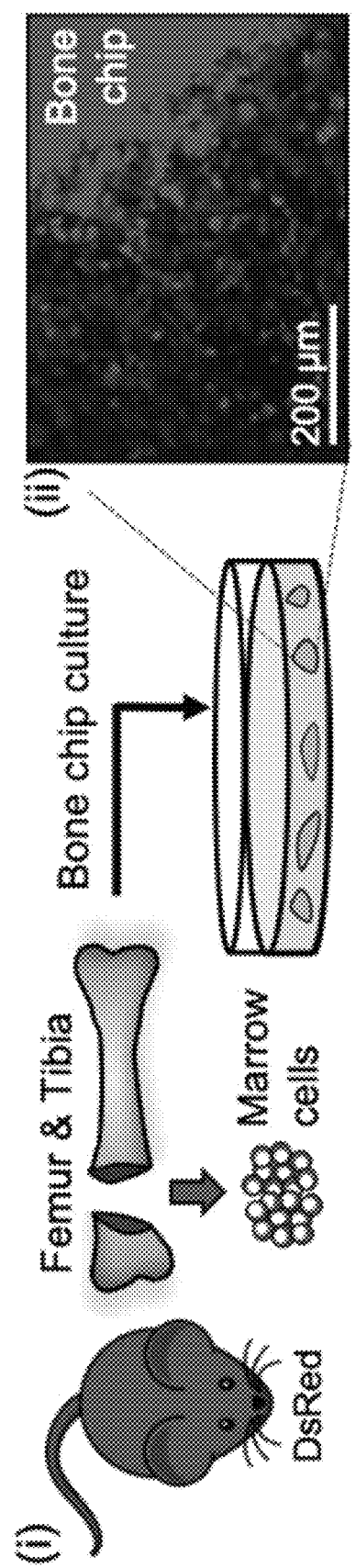
FIGS. 2A to 2H show osteoblasts rapidly mineralize DBP in a way that preserves the underlying lamellar structure.
Figure 2B:
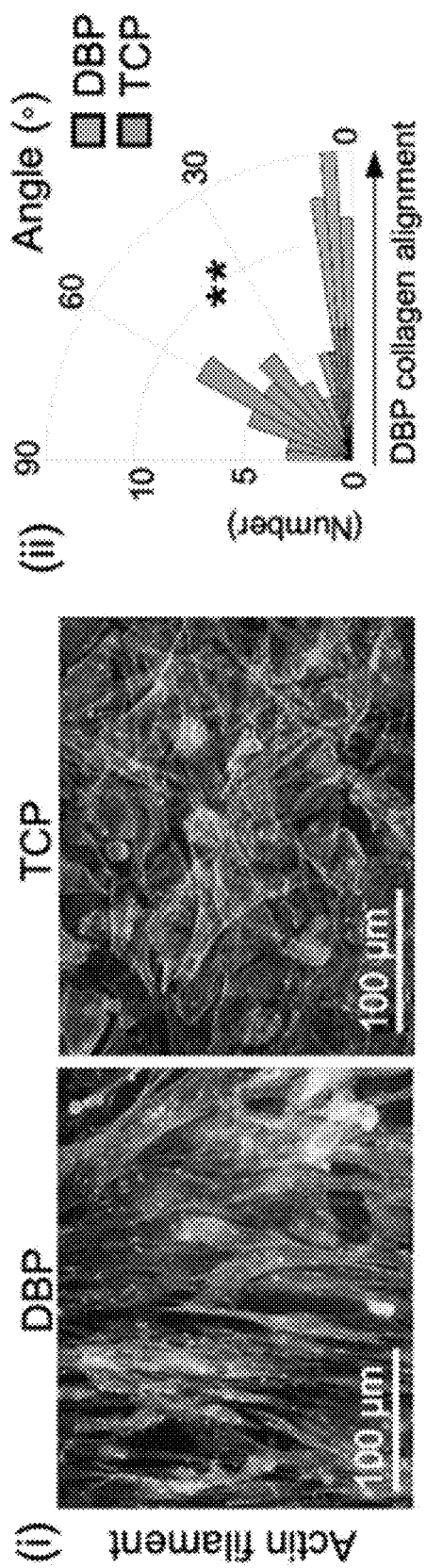
Figure 2C:
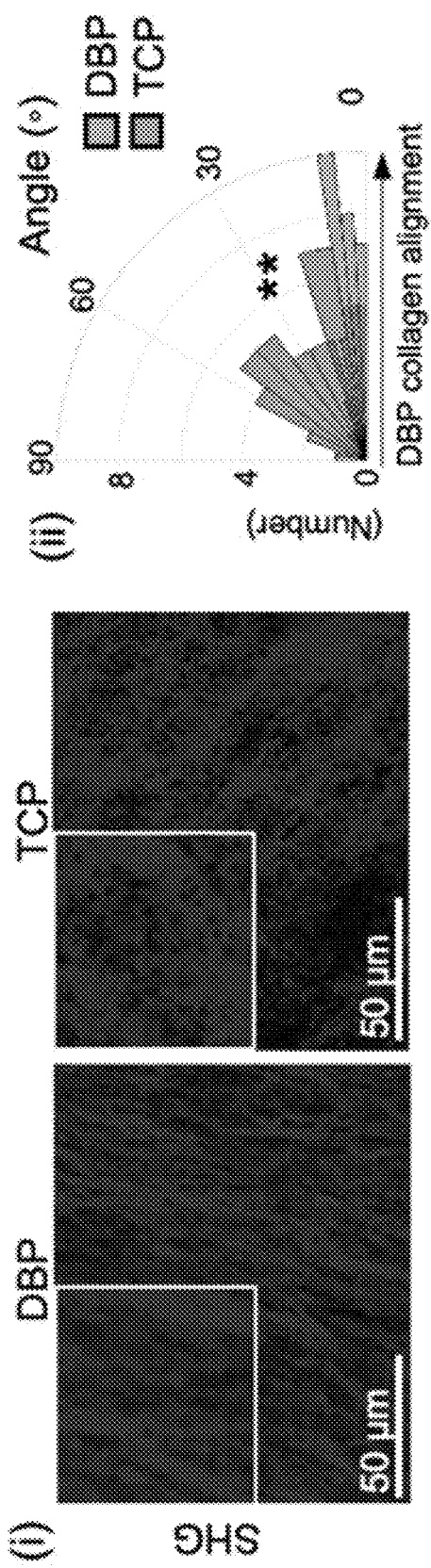
Figure 9A:
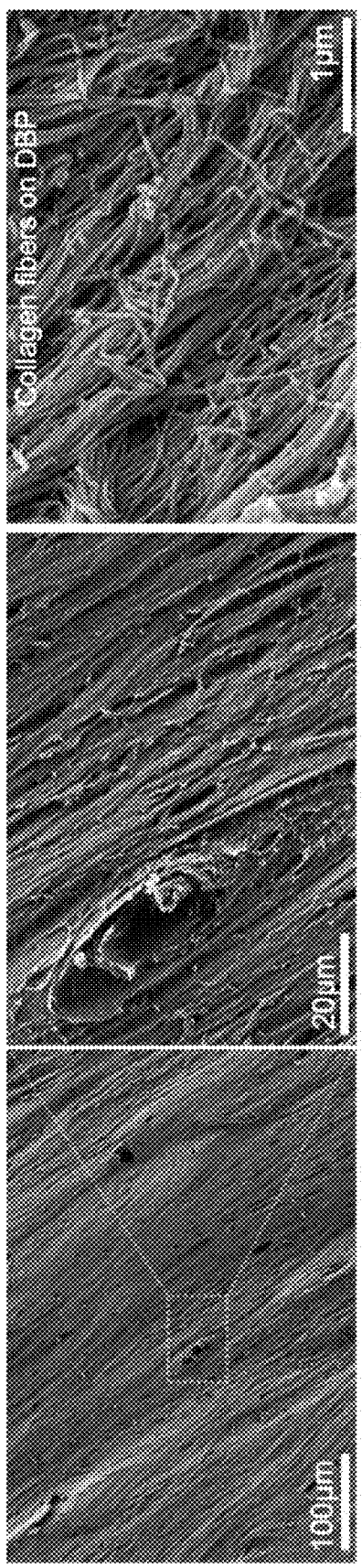
FIGS. 9A and 9B are SEM images showing the surface of DBP and after 1-week culture of osteoblasts.
Figure 9B:
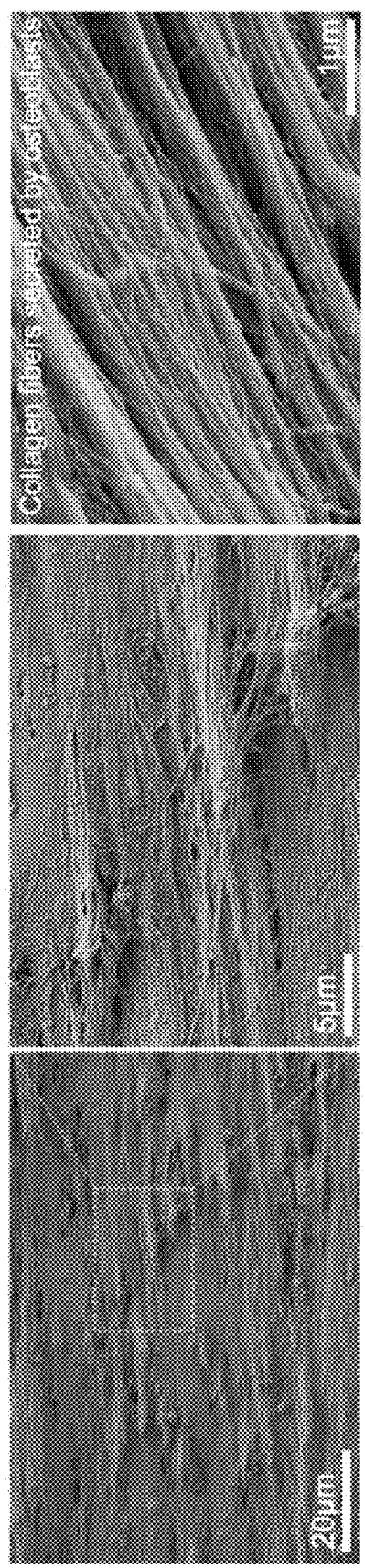

To monitor long-term cellular processes on DBP, osteoblasts were collected from DsRed reporter mice by gently crushing femoral and tibial bones and treating the bone chips with collagenase (FIG. 2A). TCP was used as a control substrate for DBP. Although TCP lacks bone-relevant ECM, it is similar to DBP in that it supports reproducible and analytical osteogenic cell culture experiments because it is standardized, bioactive, and has optical transparency. Osteoblasts cultured on vertically sectioned DBP for 3 days developed elongated morphology aligned with the underlying lamellar structure of the demineralized bone (±4.9°), whereas osteoblasts cultured on TCP had irregular shape and inconsistent alignment (±25.6°) (FIG. 2B). Multiphoton second harmonic imaging microscopy showed that osteoblasts on DBP deposited collagen fibers that were directionally aligned with the lamellar structure of the bone (±7.3°), whereas those cultured on TCP had irregular collagen fiber alignment (±26.2°) (FIG. 2C). SEM imaging further confirmed that osteoblasts on DBP deposit collagen fibers directionally (FIG. 9).

Figure 2D:
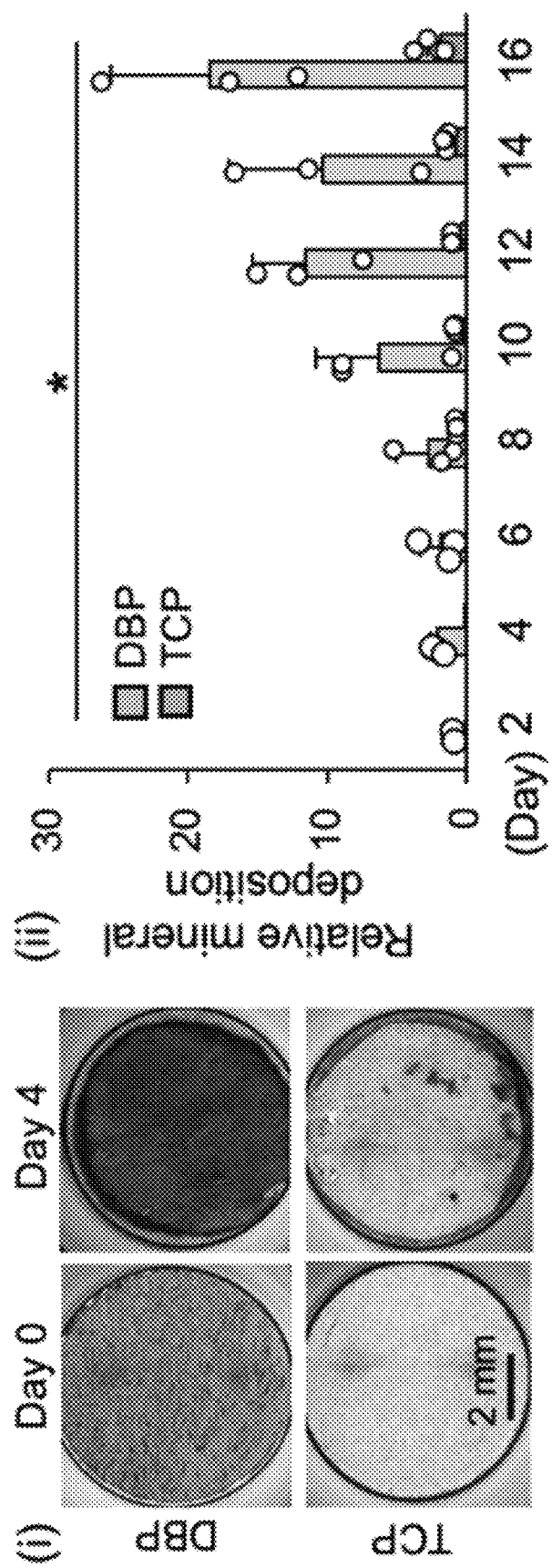
Figure 2E:
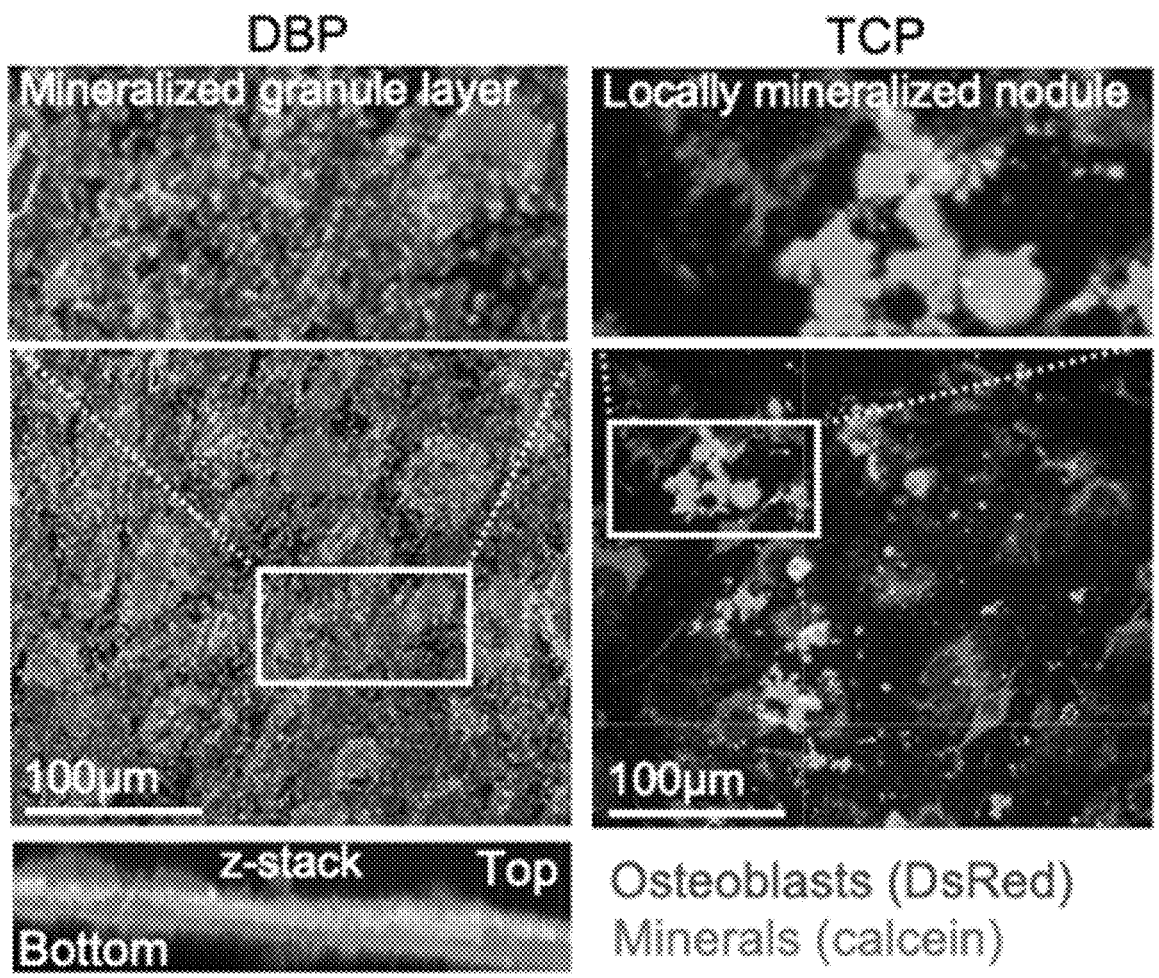
Figure 2F:
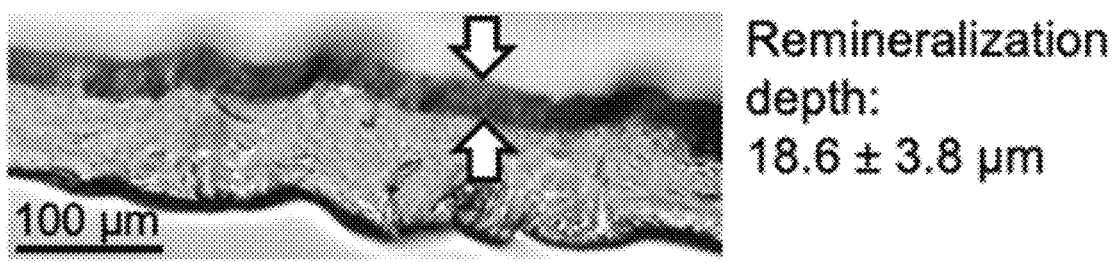
Figure 2G:
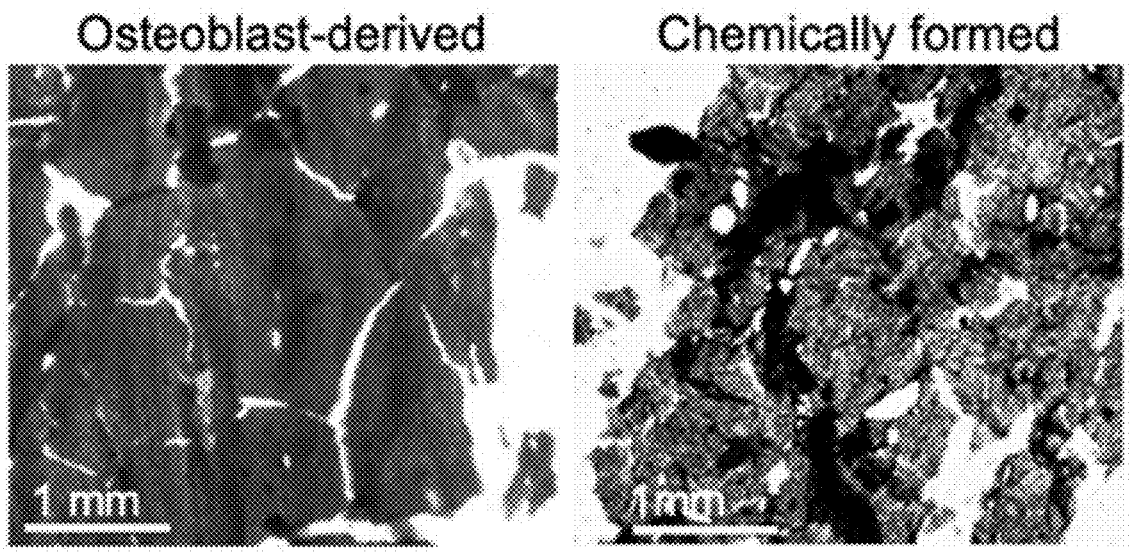
Figure 2H:
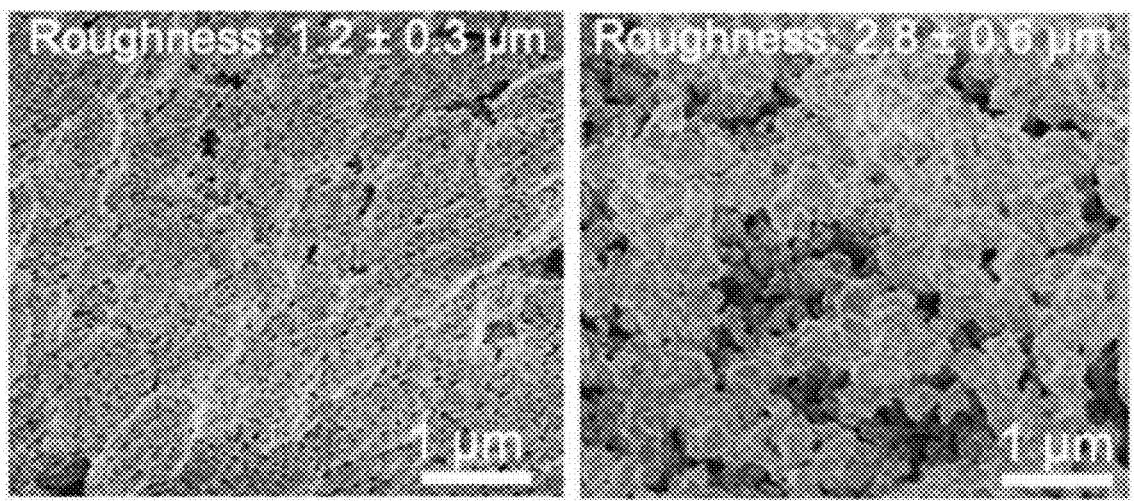
Figure 10:
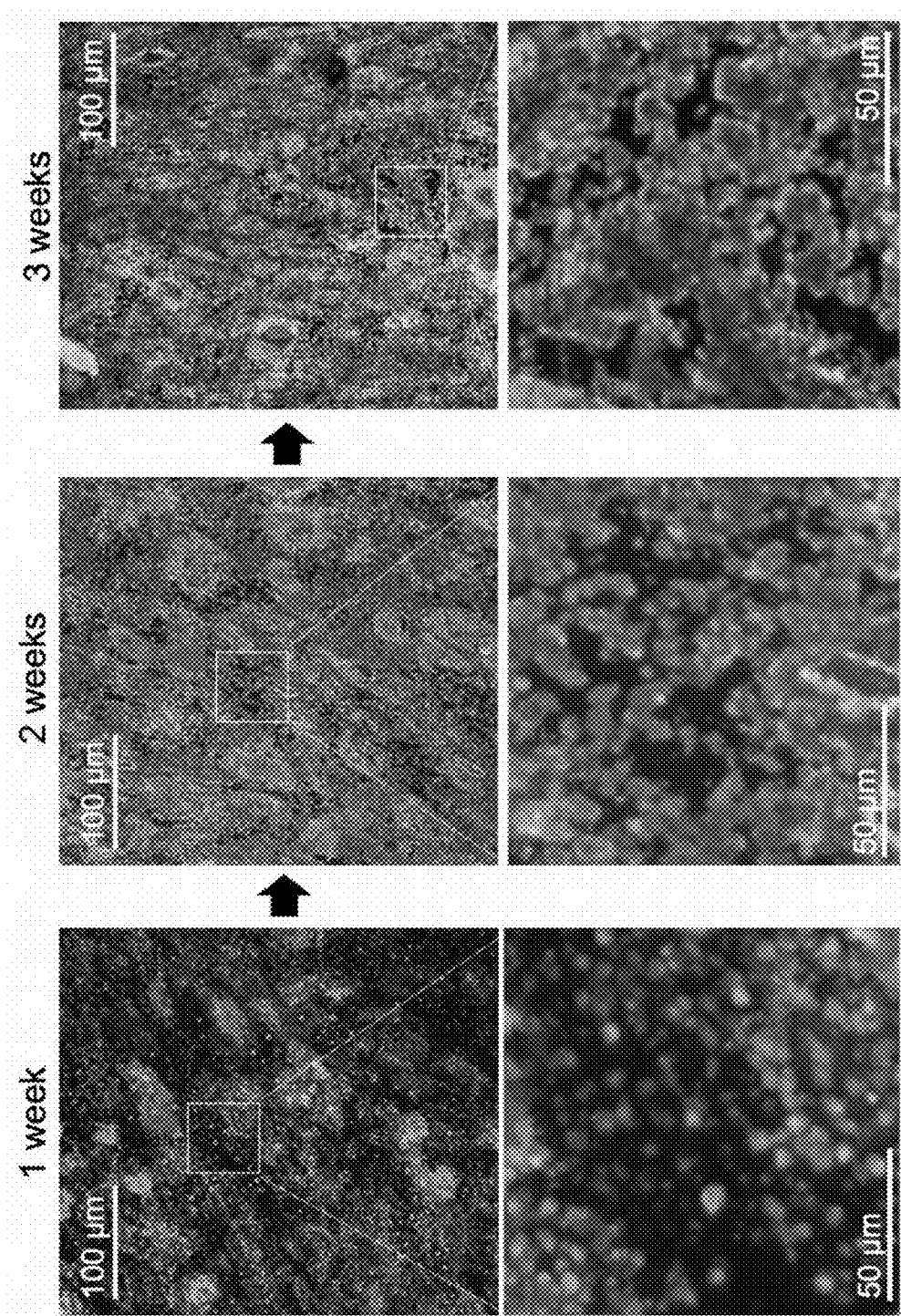
FIG. 10 contains time-course confocal images showing mineral deposition on DBP by osteoblasts. Osteoblasts and deposited mineral stained with fluorophore calcein over 3 weeks of culture.
Figure 11B:
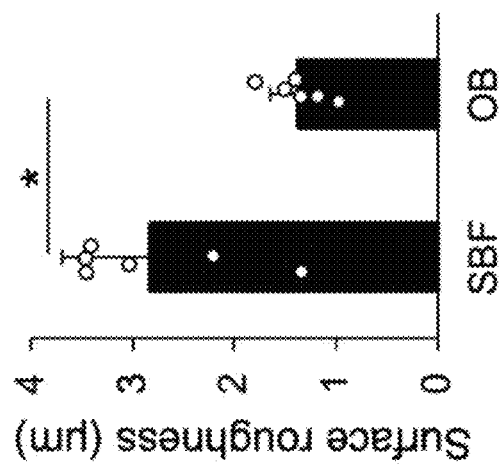
FIGS. 11A and 11B show characterization of mineralized surface roughness on DBP between simulated body fluid and osteoblasts using a 3D optical profilometer.
Figure 11A:
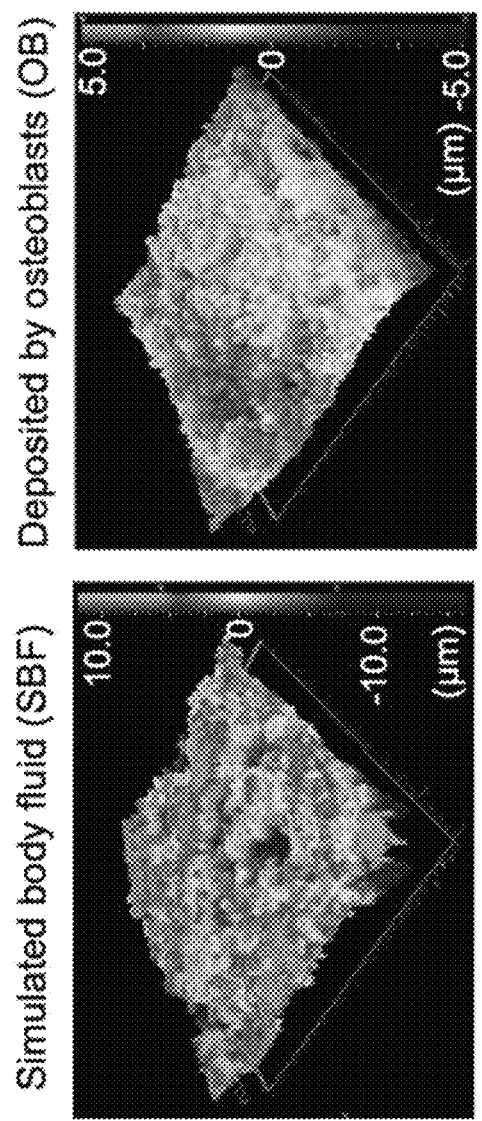

Next mineralization by osteoblasts in osteogenic differentiation medium was characterized. Time-course images with alizarin red mineral stain showed that osteoblasts on DBP completely covered the surface after 4 days and continued to deposit minerals for more than 2 weeks. In the same time period, osteoblasts on TCP deposited collagen, but deposited minerals in only a few localized regions (FIG. 2D). Fluorochrome calcein staining was then conducted to characterize mineral deposition patterns. On DBP, mineral deposition began with small granules embedded in the preexisting collagen matrix that gradually grew and developed into a mineralized layer (FIG. 10). In contrast, on TCP mineral deposition occurred at local spots where clusters of osteoblasts formed mineralized nodules. Cross-sectional confocal imaging revealed that on DBP most mineral deposition occurred beneath osteoblasts (FIG. 2E). After 3 weeks of culture on 100-μm-thick DBP, osteoblasts typically mineralized to a depth of 18.6±3.8 μm (FIG. 2F). Finally, the deposited mineral structure without organic components was characterized via thermal decomposition. Cell-derived mineral layers exhibited long-range crystalline-like morphology. By contrast, mineral layers that were only formed chemically with simulated body fluid had a disorganized structure (FIG. 2G). SEM showed that cell-derived mineral had densely fused, smooth mineral layers, whereas chemically formed mineral layers exhibited coarse aggregation of mineral granules (FIG. 2H). The characteristic surface roughness of chemically formed mineral layers was 2.3-fold higher than that of mineral layers formed by osteoblasts (FIG. 11). These results indicate that DBP directs osteoblasts to proceed with rapid and structural mineralization similar to that seen in in vivo osteoid bone (Reznikov, N, et al. Science 2018 360:eaao2189; Boonrungsiman, S, et al. Proc Natl Acad Sci USA 2012 109:14170-14175).

Osteoblasts on DBP Acquire the Bone Lining Cell Phenotype.

Figure 3B:
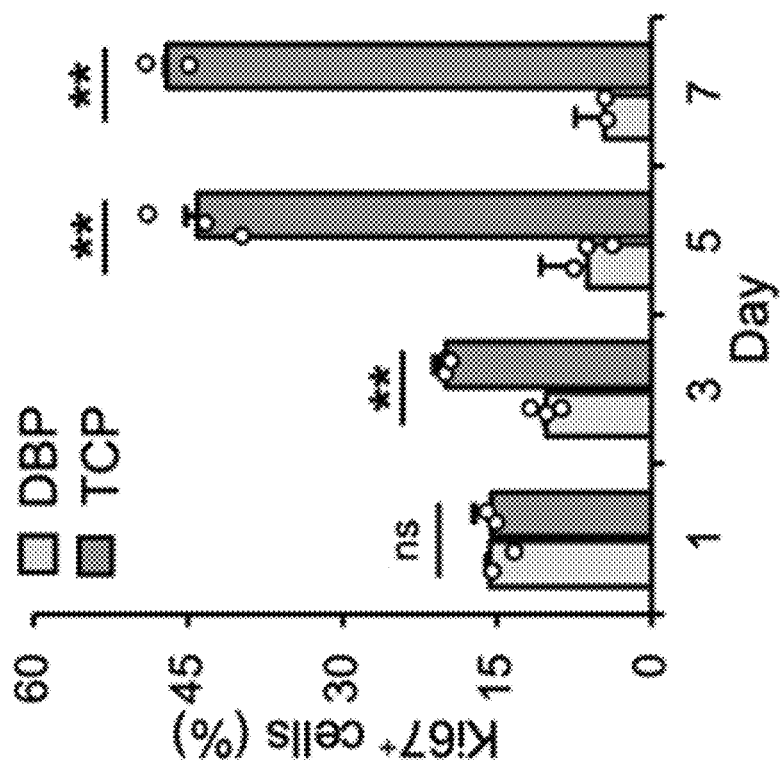
FIGS. 3A to 3F show osteoblasts on DBP acquire the bone lining cell phenotype.
Figure 3A:
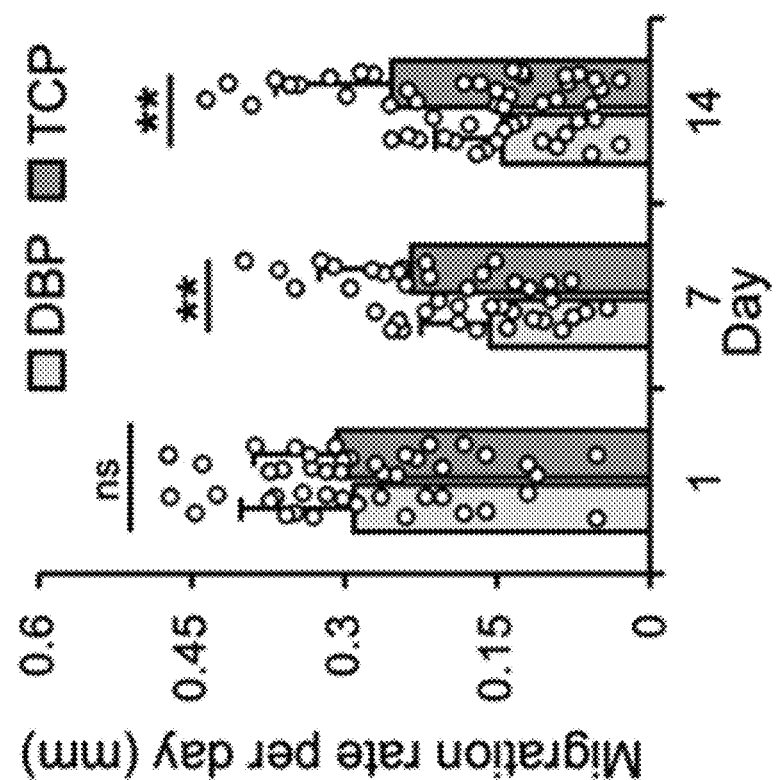
Figure 3C:
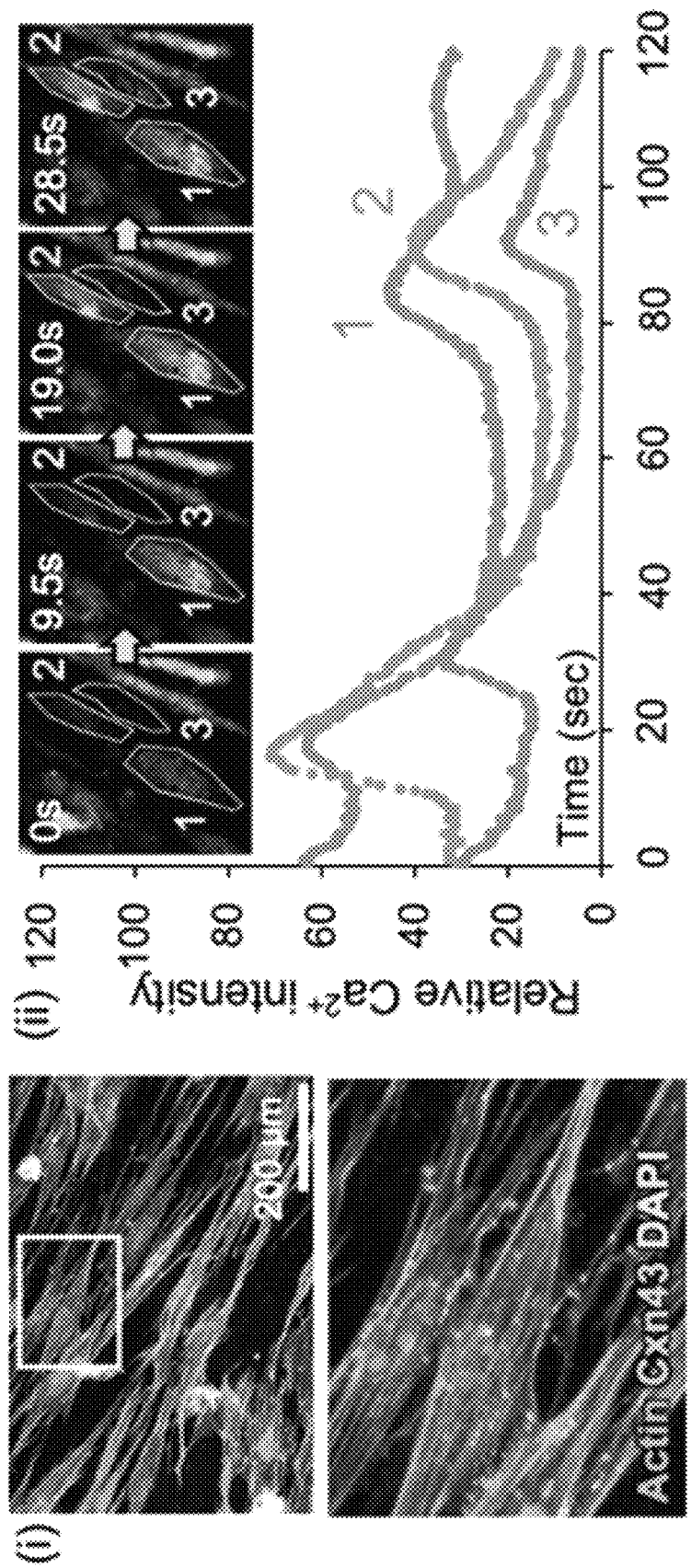

Next investigated was whether DBP can direct osteoblasts to acquire the bone lining cell phenotype and associated cellular organization and communication (Miller, S C, et al. Scanning Microsc 1989 3:953-960). Osteoblasts seeded on DBP decreased migration and proliferation over time. After they were cultured for 2 weeks, osteoblasts on DBP showed 2-fold decreased motility (157±15 μm/d), whereas those on TCP maintained high motility (309±29 μm/d) (FIG. 3A). Immunofluorescent staining of 1-week cultures with mitogenic marker Ki67$^+$ showed four times downregulated proliferation on DBP, but three times upregulated mitogenic activity on TCP (FIG. 3B). Next examined was whether osteoblasts cultured on DBP develop functional gap junctions. Immunofluorescent staining confirmed that osteoblasts express connexin 43, a key molecule in gap junction (Plotkin, L I, et al. Bone 2013 52:157-166). Gap junction-mediated cellular communication was further confirmed by time-lapse fluorescent imaging of $Ca^{2+}$, which showed sequential $Ca^{2+}$ influx to adjacent bone lining cells under potassium stimulation (FIG. 3C). These data confirm that osteoblasts cultured on DBP for 1 week take on the bone lining cell phenotype. Hereafter osteoblasts that have been cultured on DBP for more than 1 week are referred to as "bone lining cells."

Figure 3D:
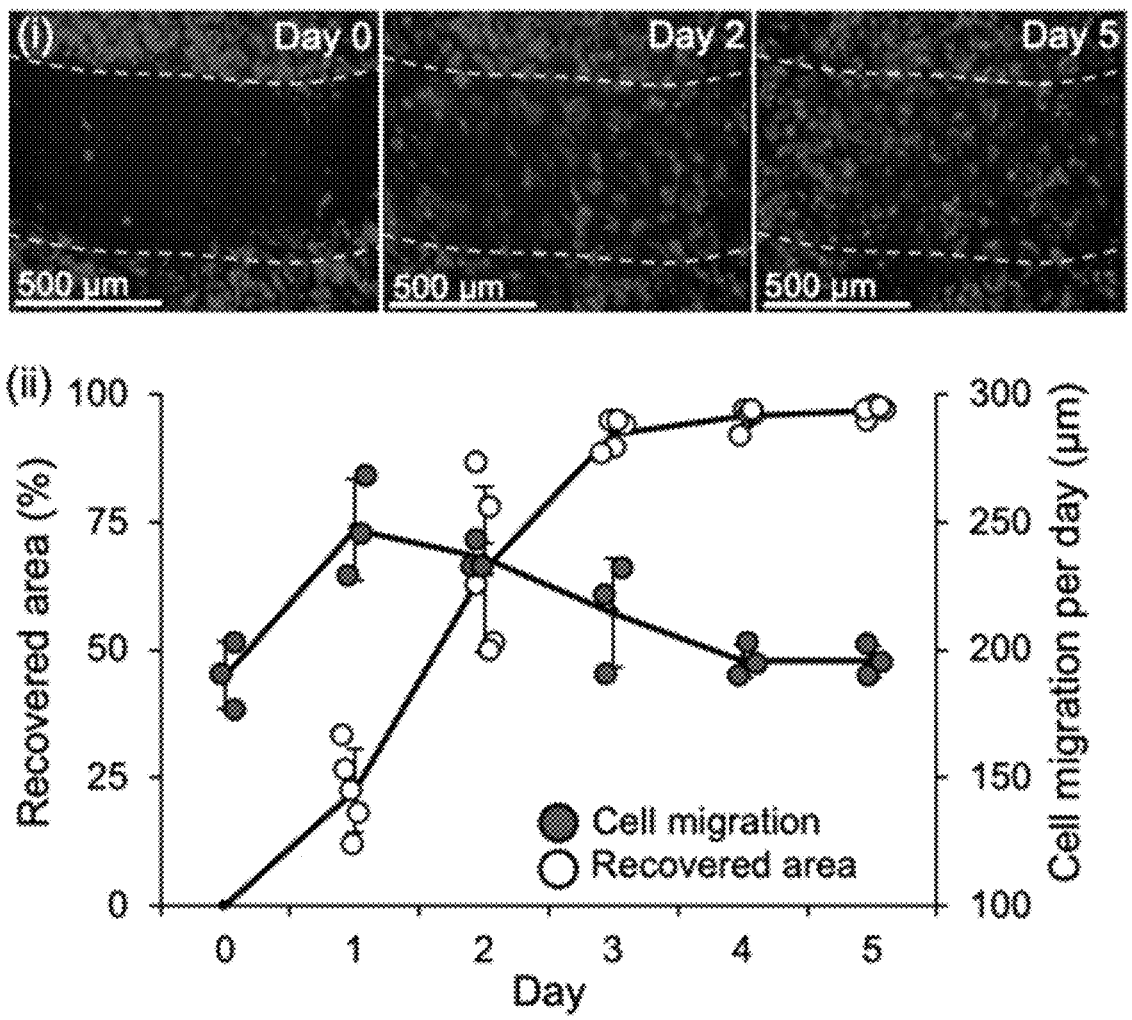
Figure 3E:
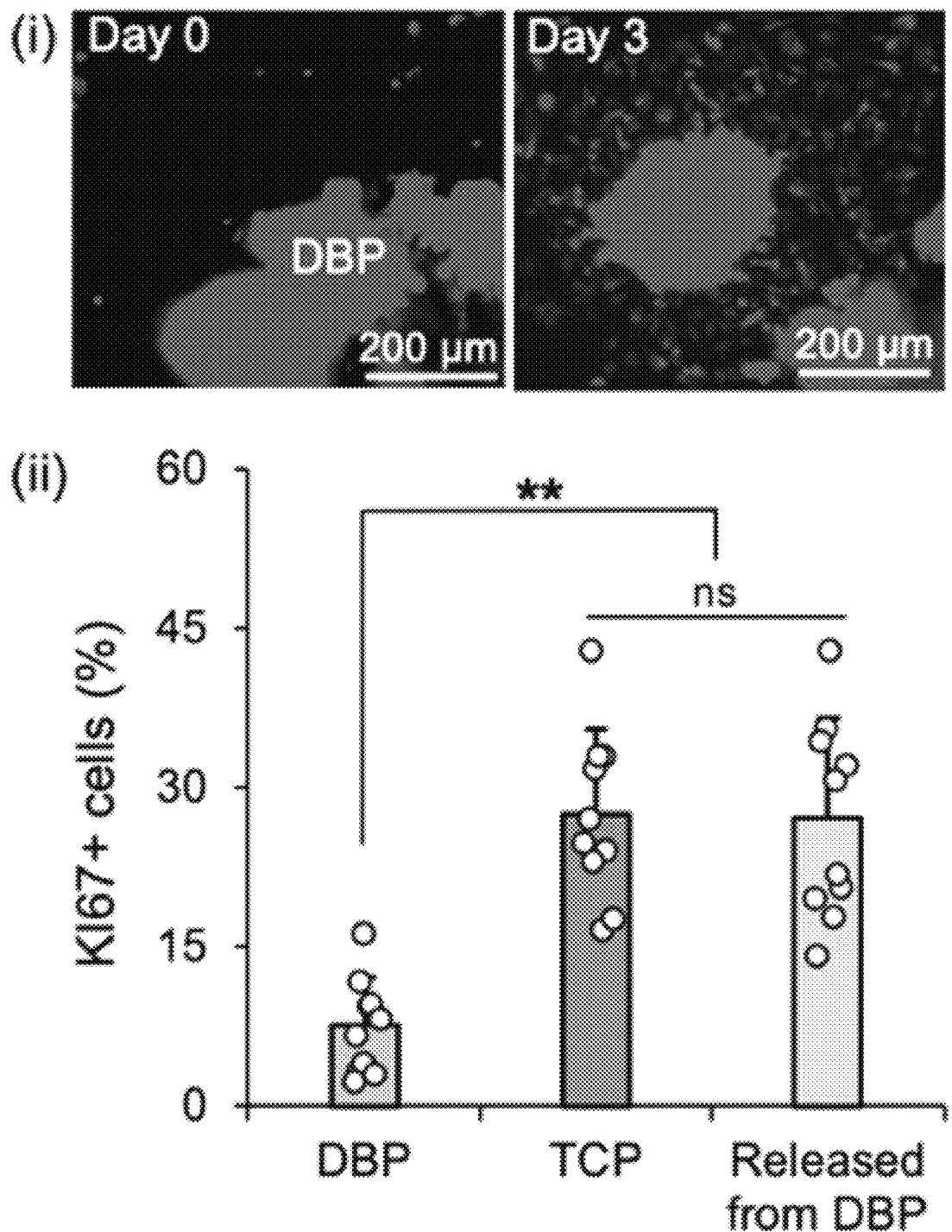
Figure 3F:
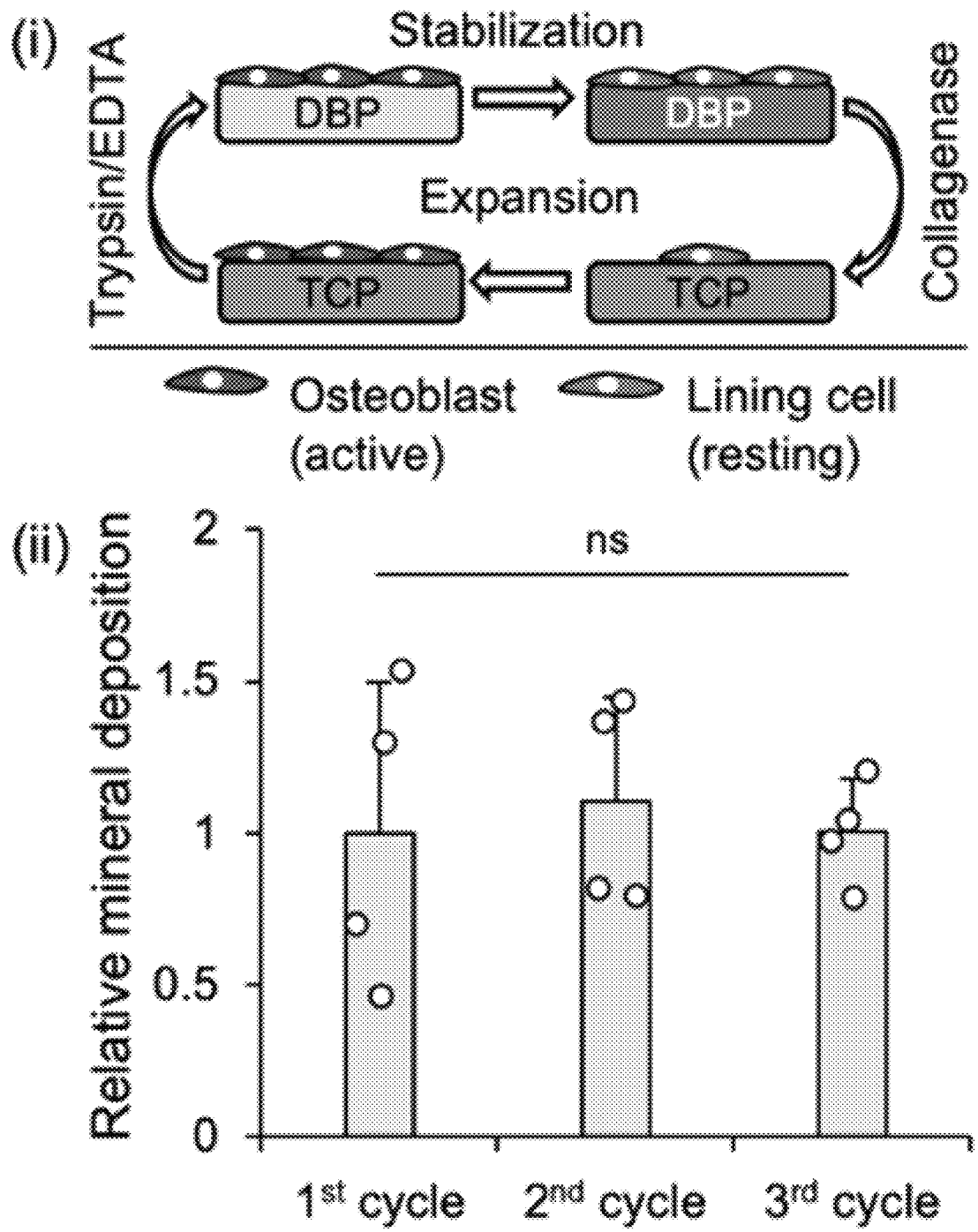

Two functional assays were developed to determine if cells that have taken on the bone lining cell state can regain osteogenic activity. First, a bone surface healing assay was developed. The surface of DBP containing bone lining cells were scratched and the subsequent activation of lining cells and increase in surface coverage was monitored. Time-lapse imaging over 5 days showed that migratory activity of bone lining cells increased transiently then gradually returned to a resting state as the damaged area became completely confluent (FIG. 3D). Second, an osteoblast phenotypic switching assay was developed. Established bone lining cells from DBP were released by degrading the DBP with collagenase. The released cells on TCP was then cultured, showing that they resumed their migratory and proliferative activity. Quantitative analysis of Ki67+ cells confirmed that bone lining cells released from DBP and cultured on TCP for 1 week recovered mitogenic activity comparable to that of osteoblasts that were continuously cultured on TCP (FIG. 3E). When the TCP-expanded osteoblasts were detached and reintroduced onto DBP, they regained the bone lining cell phenotype. This cycle of phenotypic switching from resting to active states by alternating DBP and TCP substrates was repeated at least three times. With each cycle, the time required to reach 80% confluency on TCP increased: 8 days in the first cycle, 15 days in the second cycle, and 30 days in the third cycle. Alizarin red staining showed that mineral deposition activity was similar in each of the three cycles (FIG. 3F). These data indicate that cells that take on the bone lining cell phenotype on DBP retain the ability to revert to active state osteoblasts, as they would in the bone remodeling cycle in vivo (Raggatt, L J, et al. J Biol Chem 2010 285:25103-25108; Matic, I, et al. Stem Cells 2016 34:2930-2942).

The microenvironment of DBP supports the bone remodeling cycle.

Figure 4A:
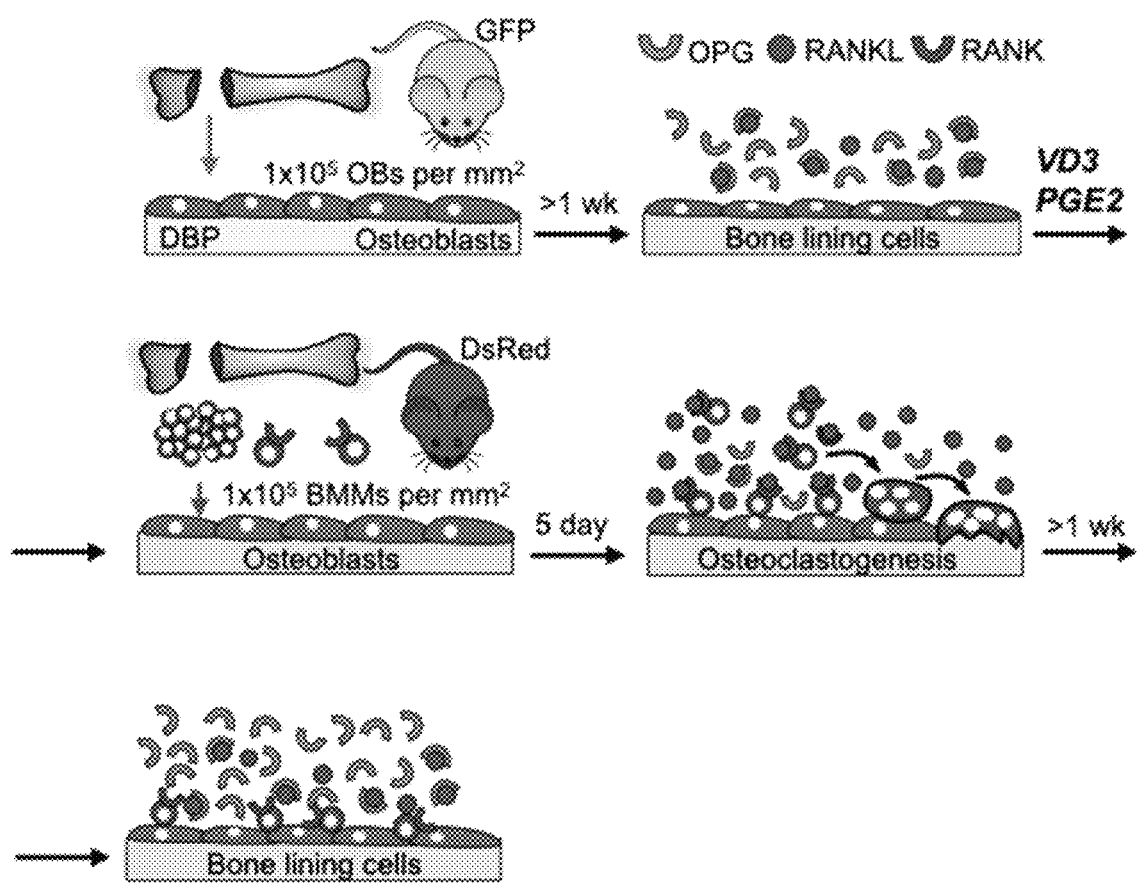
Figure 4B:
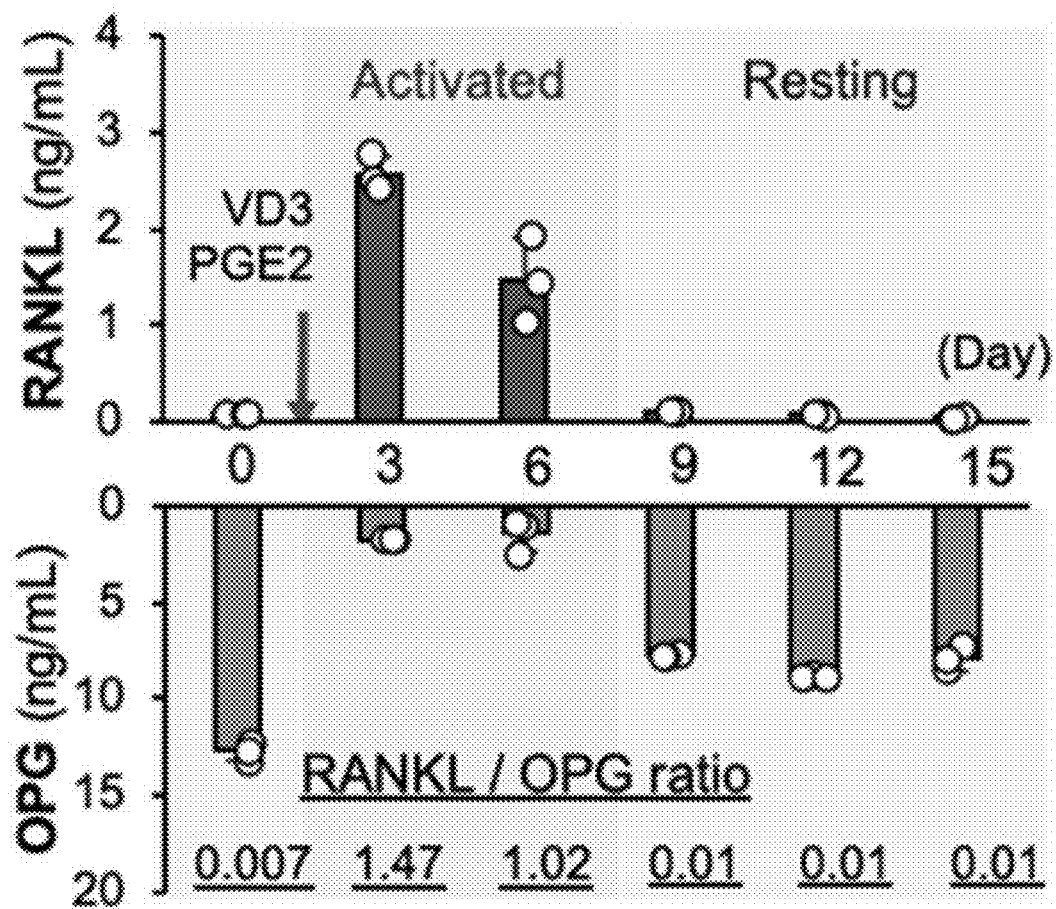
Figure 12:
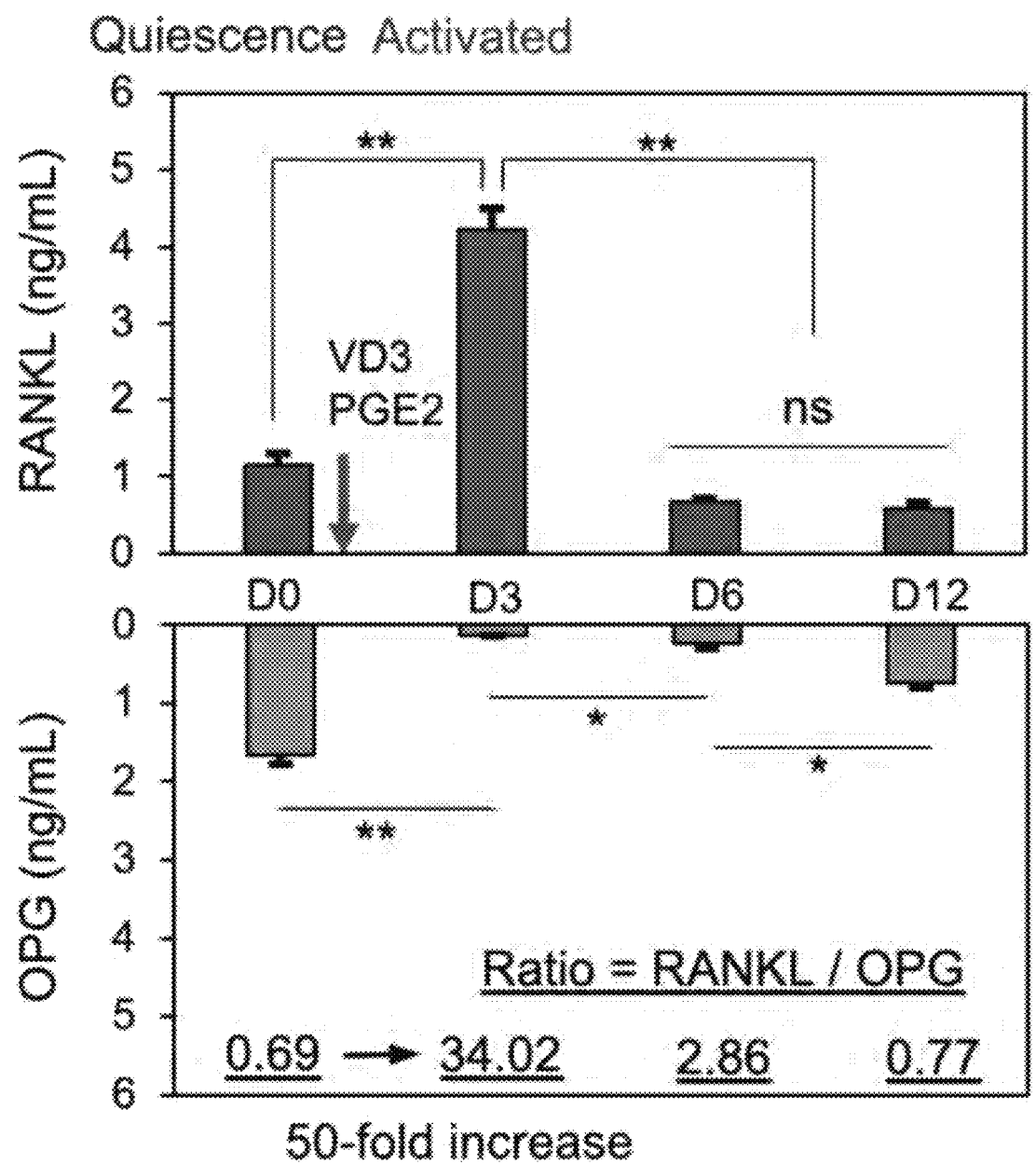
FIG. 12 shows time-course measurement of OPG and RANKL secretion by osteoblasts on TCP after VD3 and PGE2 stimulation. (n=6) (*P<0.05, **P<0.01)

Bone remodeling begins when chemical or mechanical stimulation triggers a shift in the local profile of osteogenic regulatory molecules that induces BMMs to differentiate into osteoclasts. When stimulation ceases, upregulated stimulatory molecules return to resting levels and bone remodeling terminates (Raggatt, L J, et al. J Biol Chem 2010 285:25103-25108). To reproduce the activation of a bone remodeling cycle, bone lining cells on DBP were stimulated to become active and then BMMs added to see if the BMMs differentiated into osteoclasts and initiated bone remodeling (FIG. 4A). First, enzyme-linked immunosorbent assays were used to measure the profiles of representative stimulative and suppressive molecules—RANKL and OPG—secreted by bone lining cells on DBP. The bone lining cells secreted high OPG (12.7±0.5 ng/mL) and low RANKL (0.09±0.001 ng/mL). The ratio of OPG to RANKL was 0.007, which indicates a highly suppressive molecular milieu for the initiation of bone remodeling cycle. Next examined was whether bone lining cells on DBP change their secretory profile when exposed to chemical instigators of bone remodeling, vitamin D3 (VD3) and prostaglandin E2 (PGE2) (Borciani, G, et al. Acta Biomater 2020 108:22-45). When exposed to a physiological range of VD3 (10 nM) and PGE2 (1 µM), the secretion profile of the bone lining cells dramatically shifted: OPG decreased 6-fold and RANKL increased 30-fold. The shifted RANKL/OPG ratio was 1.47, which indicates a permissive molecular niche for bone resorption. Without additional stimulation, the secretion profile gradually returned to the initial resting state in 1 week (FIG. 4B). In contrast, osteoblasts on TCP secreted moderate levels of OPG (1.6±0.02 ng/mL) and RANKL (1.1±0.04 ng/mL) at a ratio of 0.65, nearly 100 times higher than the ratio secreted by bone lining cells on DBP. VD3 and PGE2 stimulation also shifted the secretory profile of osteoblasts on TCP to a RANKL/OPG ratio to 34.2. After stimulation, the cells on TCP returned to the initial state of molecular secretion more slowly than did those on DBP (FIG. 12).

Next examined was whether the upregulated secretion of stimulatory molecules by activated bone lining cells on DBP can induce BMMs to differentiate into osteoclasts. GFP-expressing osteoblasts and DsRed-expressing BMMs were used to facilitate long-term, time-lapse fluorescent monitoring of multicellular processes in the DBP. Established bone lining cells were stimulated with VD3 and PGE2 and cocultured with $1 \times 10^6$ BMMs. After 1 week, multinucleated osteoclasts began to appear (FIG. 4C). SEM showed localized removal of the mineral layer and exposure of the collagen fibers underlying osteoclasts, confirming functional osteoclasts (FIG. 4D). These results indicate that shifted secretion of regulatory molecules was sufficient to induce BMMs to differentiate into osteoclasts that resorbed mineral. The process was repeated on TCP for comparison and found that osteoclasts began to emerge on TCP after 3 days.

Figure 4G:
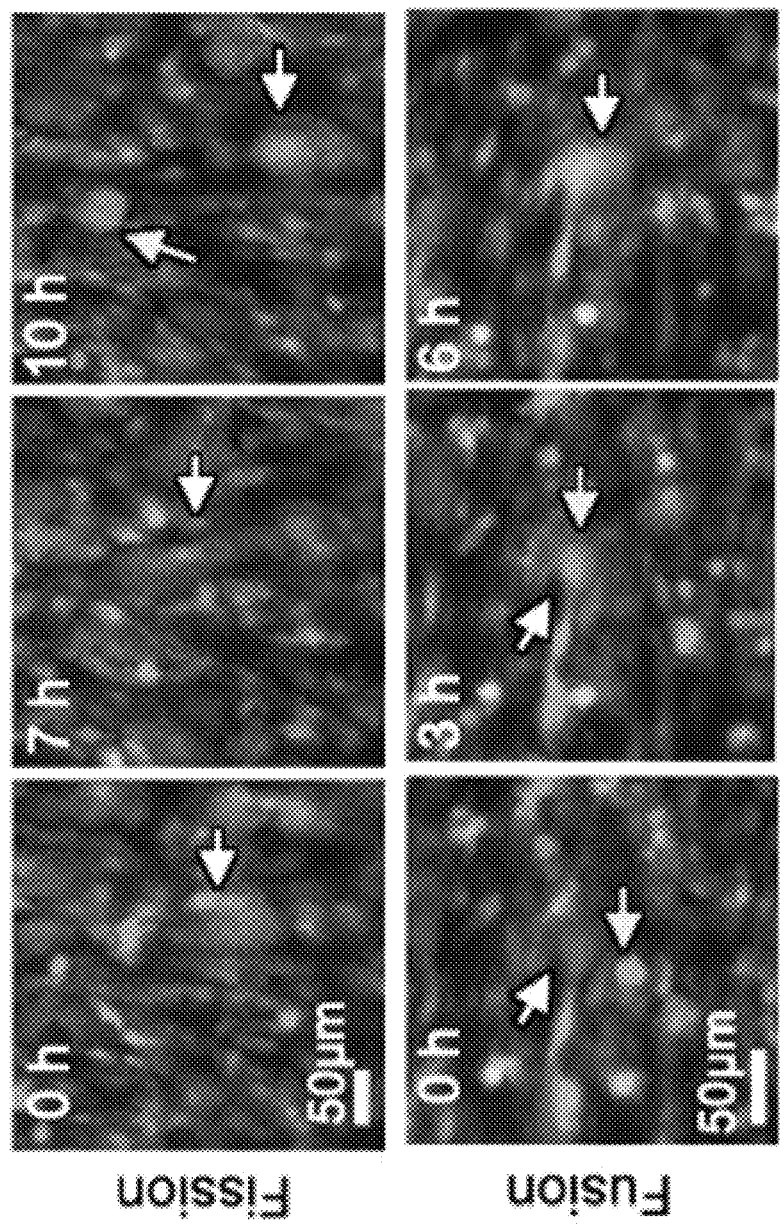
Figure 4H:
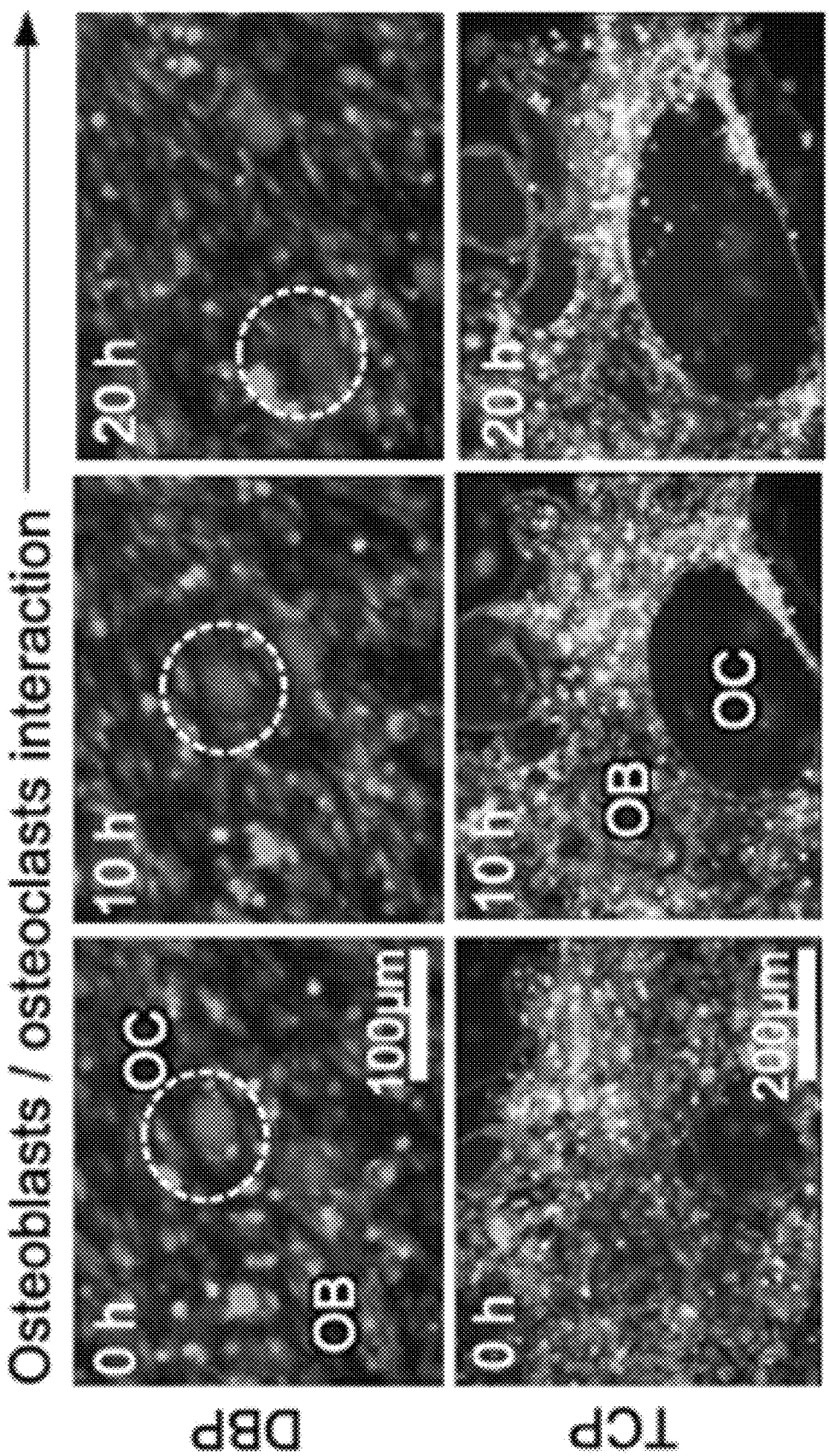
Figure 4I:
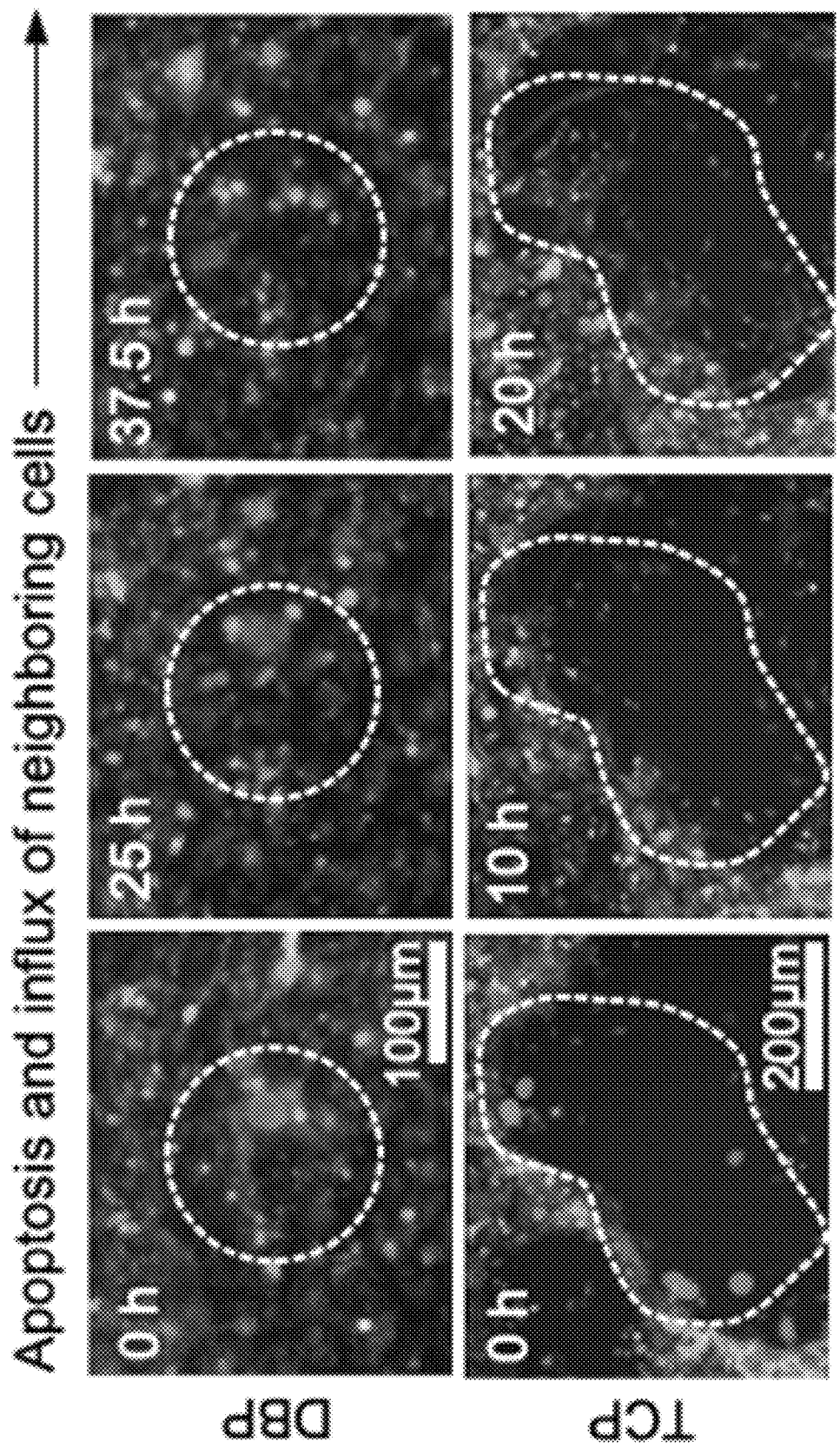
Figure 13B:
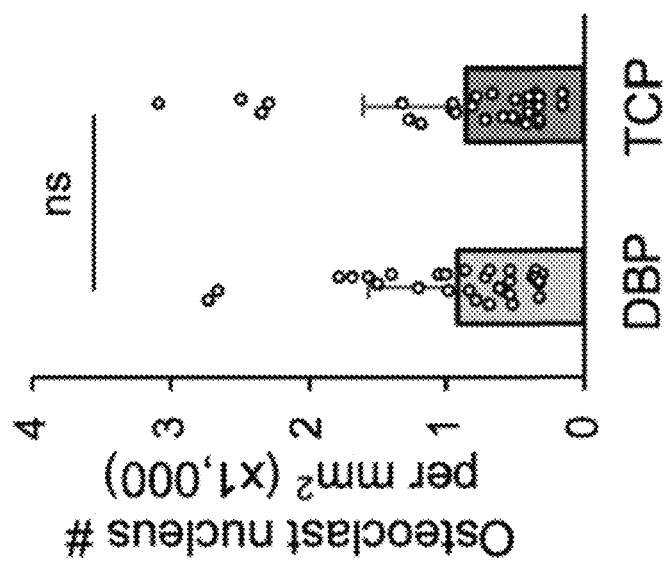
FIGS. 13A and 13B show quantitative comparison of osteoclast size and nucleus number.
Figure 13A:
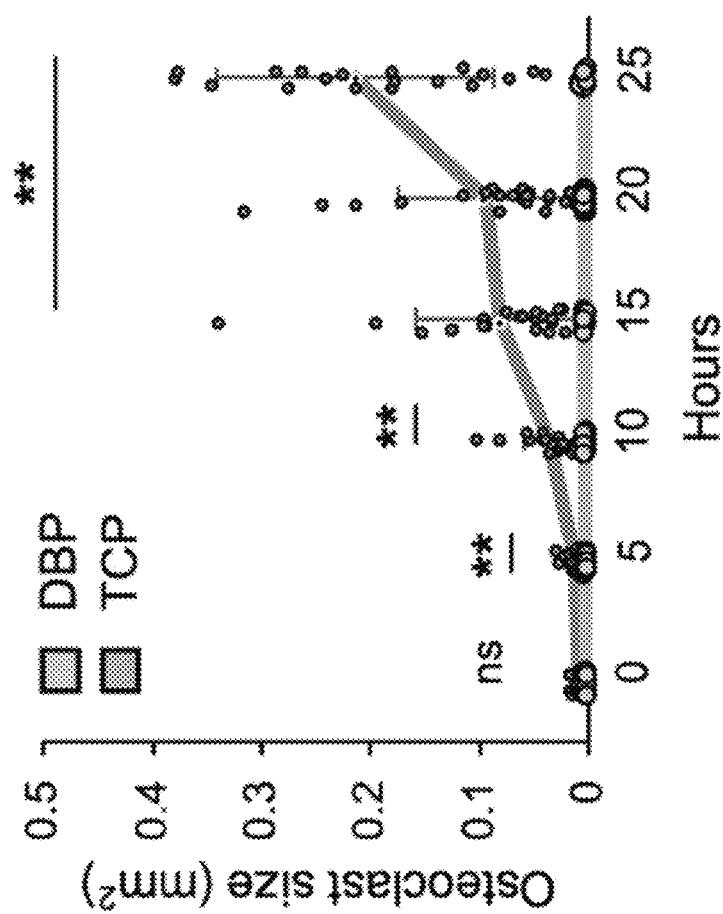

Detailed time-lapse imaging captured cellular migration activity on both materials. Stimulated osteoblasts migrated 2 times faster than their unstimulated counterparts on both DBP and TCP (FIG. 4E). On DBP, osteoclasts cocultured with stimulated osteoblasts migrated twice as fast as osteoclasts stimulated in the absence of osteoblasts. On TCP, osteoclasts cocultured with stimulated osteoblasts migrated at the same rate as osteoclasts stimulated in the absence of osteoblasts (FIG. 4F). On DBP, osteoclasts underwent cell fusion and cell fission, in which individual cells separated from the multicellular body (30) (FIG. 4G). By contrast, osteoclasts on TCP underwent cell fusion repeatedly until the cells became giant and multinucleated and cell death occurred by apoptosis. As a result of the repeated cell fusion, the osteoclasts on TCP exhibited a broad range of cell sizes (720±400 µm$^2$). Osteoclasts on DBP were significantly smaller and had narrower cell size distribution (140±43 µm$^2$), similar to that seen in trabecular bone (Jacome-Galarza, C E, et al., Nature 2019 568:541-545). Osteoclasts cultured on DBP and TCP had a similar ratio of number of nuclei to cell area (FIG. 13). Active osteoblasts on DBP held their position in the presence of osteoclasts, whereas osteoblasts on TCP were pushed aside by migrating osteoclasts (FIG. 4H). When osteoclasts on TCP underwent apoptosis, they left behind large actin-ring structures that prevented migration of neighboring osteoblasts. Instead, BMMs were the first to migrate to the region that had been occupied by the dead cell body, because they are floating cells, and osteoblasts entered 10 hours later. A similar process occurred on DBP, but was less pronounced because the osteoclasts were smaller and apoptosis was infrequent (FIG. 4I).

Figure 4J:
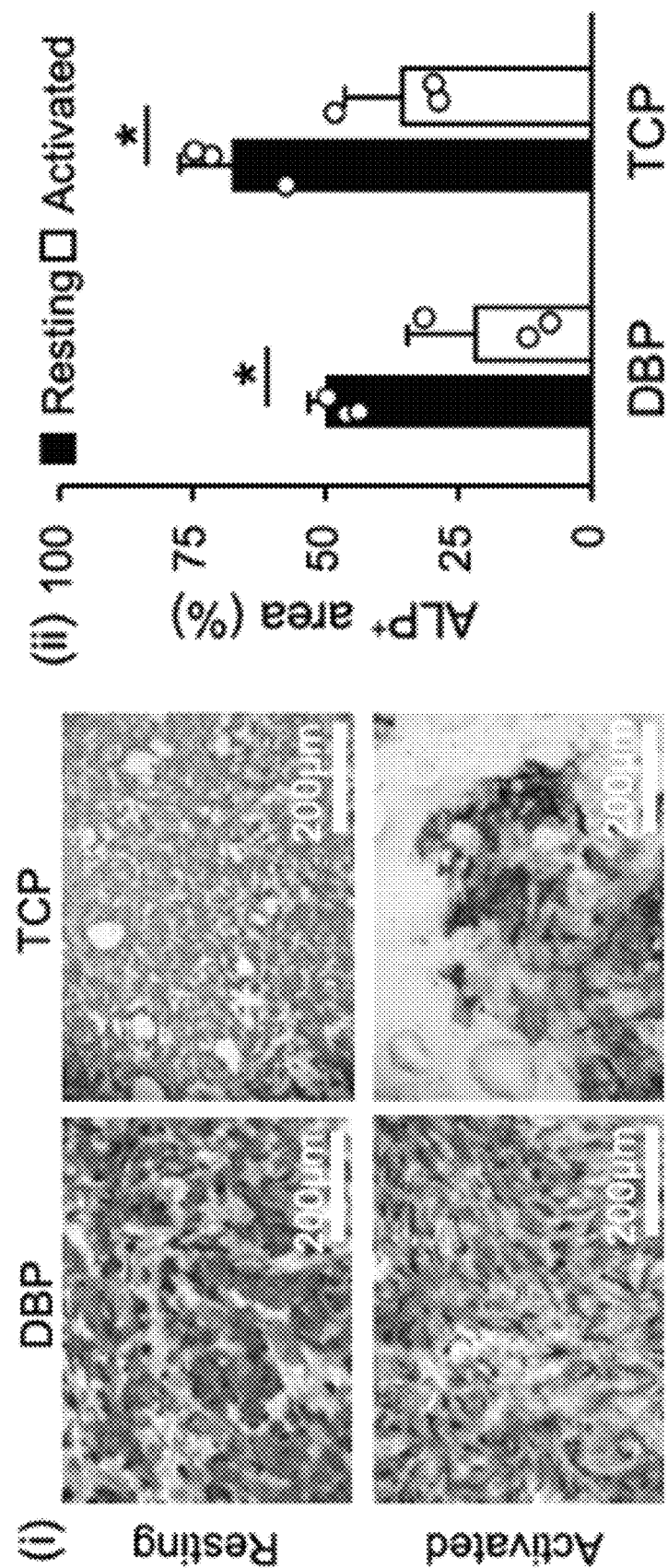
Figure 4K:
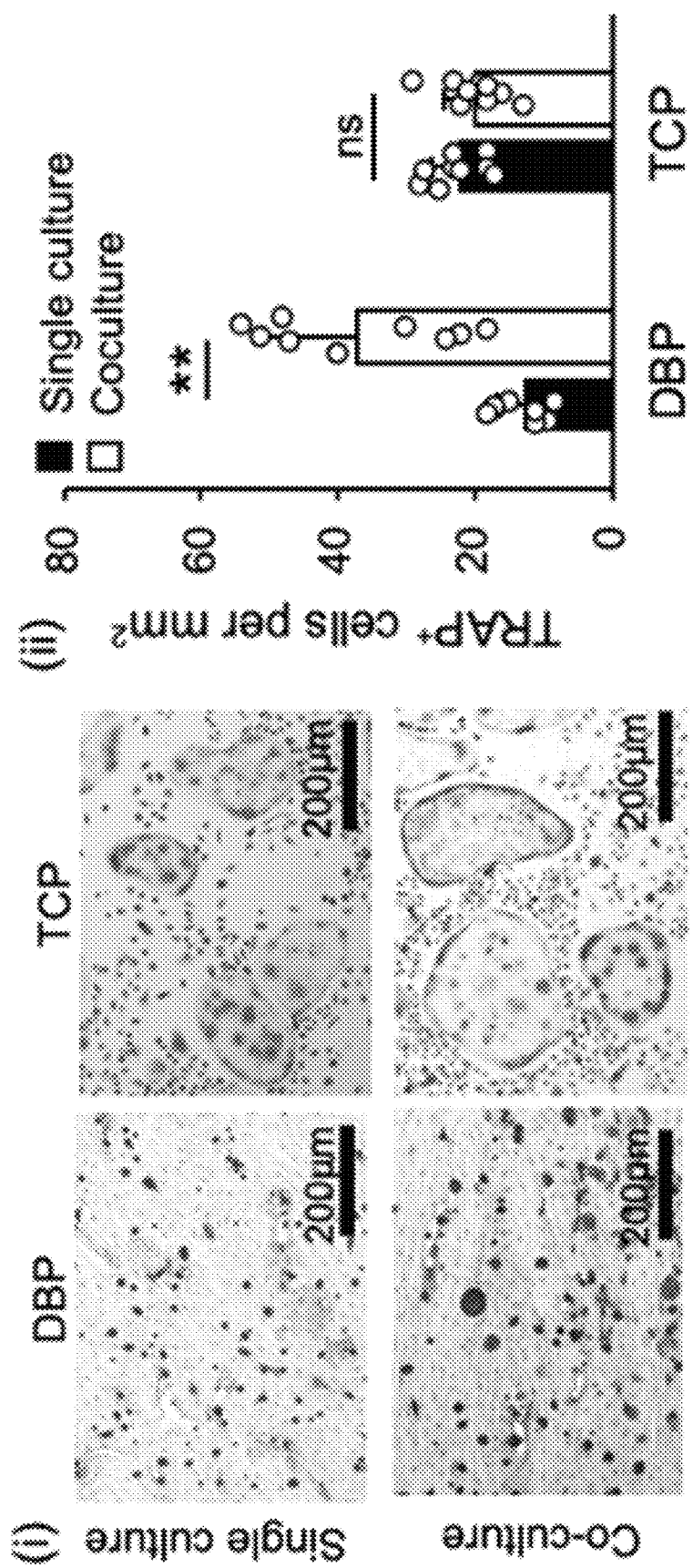

Recent data suggest that osteoblasts promote osteoclast differentiation and osteoclasts enhance osteoblast activity (Sims, N A, et al. Annu Rev Physiol 2020 82:507-529). The coupling of osteoblast and osteoclast activities was examined by measuring changes in osteoblast- and osteoclast-specific functional enzyme activities under VD3 and PGE2 stimulation. There was a focus on alkaline phosphatase (ALP), which is expressed by osteoblasts during mineral deposition, and tartrate-resistant acid phosphatase (TRAP), which is expressed by osteoclasts during mineral resorption. Before stimulation, osteoblasts expressing ALP covered 50% of the surface of DBP and 67% of the surface of TCP; after stimulation this was reduced by half on both substrates (FIG. 4J). This indicates that half of the bone lining cells actively deposit mineral and that activation interrupts the mineral deposition process. Nearly all multinucleated osteoclasts expressed TRAP. The number of TRAP+ osteoclasts on DBP increased 3-fold when the osteoclasts were cocultured with osteoblasts, whereas TRAP+ osteoclast numbers on TCP were not affected by coculture with osteoblasts (FIG. 4K). This result, along with the increased motility of osteoclasts on DBP (FIG. 4F), indicates that DBP effectively facilitates crosstalk between osteoblasts and osteoclasts. These results suggest that DBP faithfully reproduces the bone remodeling cycle and provides a quantitative analytical platform to probe the multicellular processes of trabecular bone remodeling.

DBP-based trabecular bone organoid model recapitulates localized bone remodeling in trabecular bone cavities.

Figure 5A:
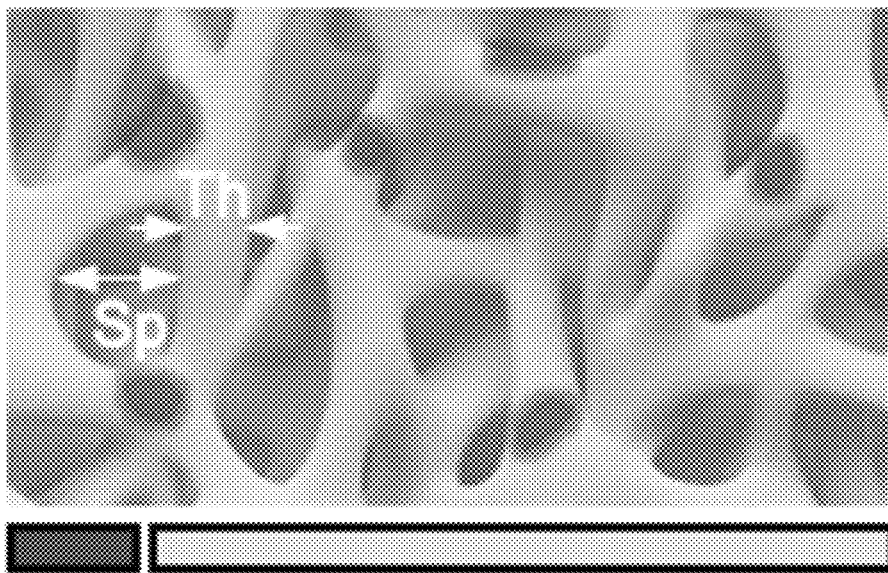
FIGS. 5A to 5G show the trabecular bone organoid model recapitulates coexisting active and resting bone surfaces.
Figure 5A:
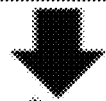
Figure 5A:
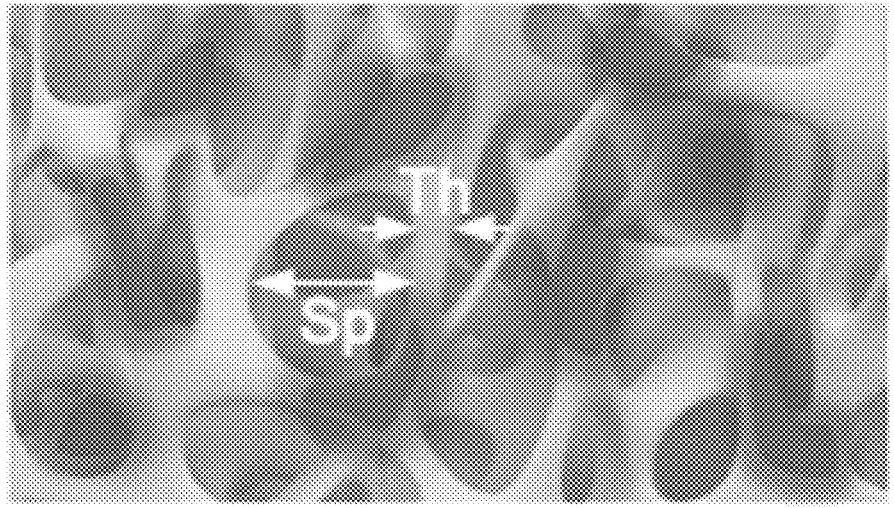
Figure 5B:
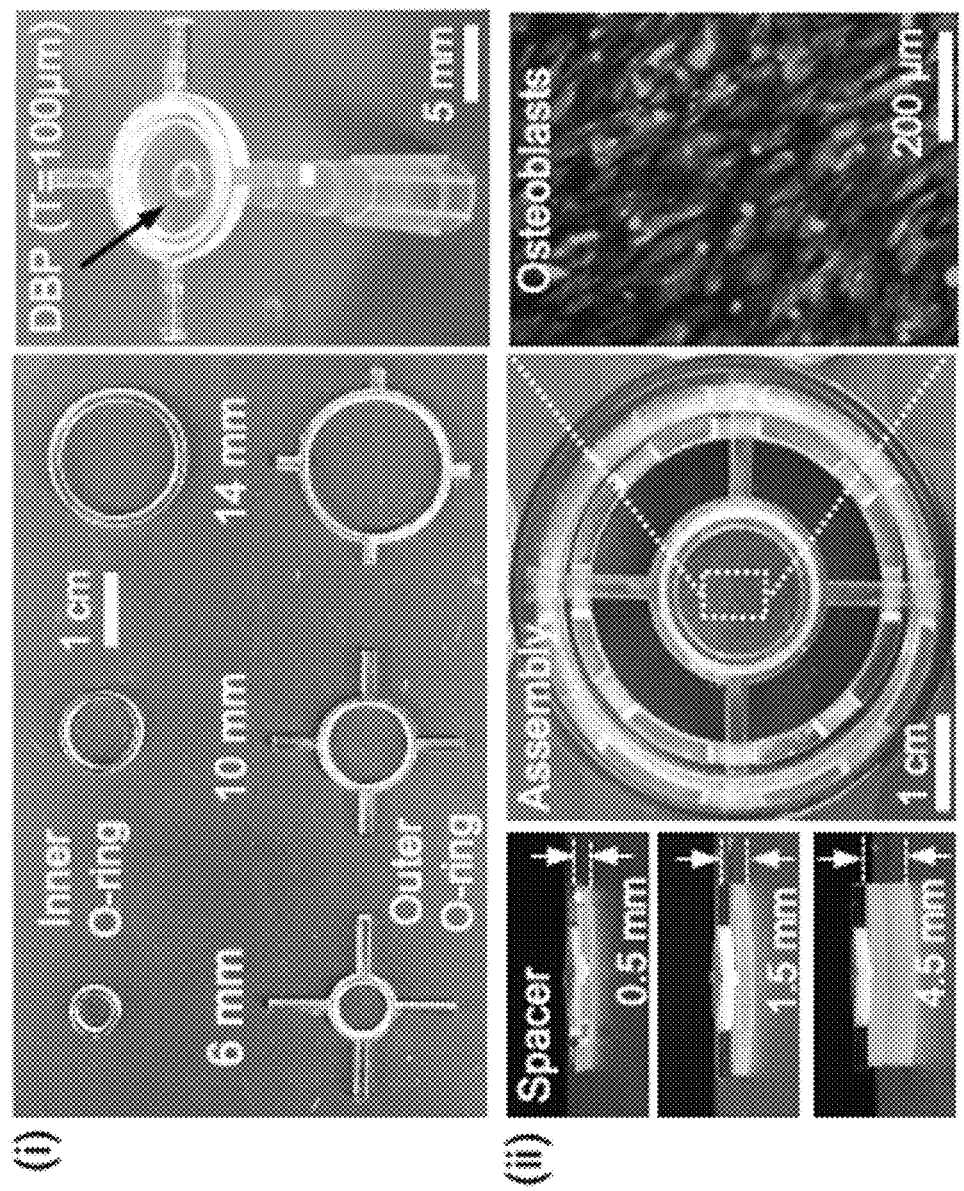
Figure 5C:
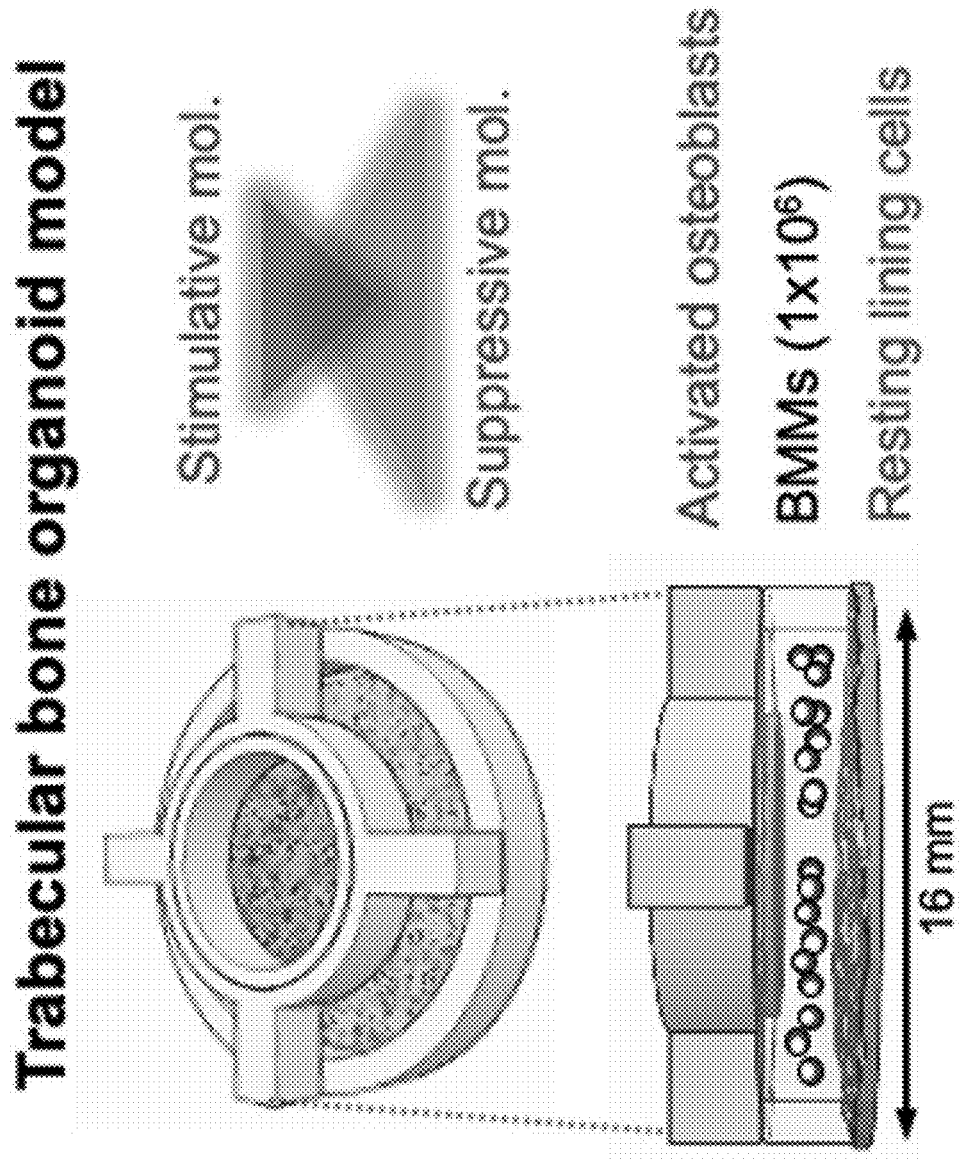

In healthy trabecular bone, remodeling activity is confined to local spots surrounded by resting surfaces. The active and resting surfaces maintain different profiles of stimulatory and suppressive secretions, which results in a unique spatiotemporal pattern of regulatory molecules (Raggatt, L J, et al. J Biol Chem 2010 285:25103-25108). Unbalanced remodeling with excessive bone resorption decreases bone thickness and increases cavity diameter (FIG. 5A). It was hypothesized that localized bone remodeling is maintained by integrated metabolic and morphological regulation. To test this hypothesis, coexisting active and resting bone surfaces were simulated by culturing DBP disks with resting-state bone lining cells with DBP inserts with active osteoblasts. DBP inserts were created by fastening 100-μm-thick circles of DBP between two concentric O-rings. Ring-shaped spacers were built to separate the resting-state and active-state surfaces to simulate the space in trabecular bone cavities (FIG. 5B). 6 mm, 10 mm, and 14 mm diameter inserts were used to represent different-sized areas of active bone surface, and 0.5 mm, 1.5 mm, and 4.5 mm spacers were used to simulate different-sized trabecular bone spaces. BMMs were added to the space between the DBP disk and the DBP insert. The BMMs undergo osteoclastogenesis in response to spatiotemporal gradients of regulatory molecules. The ability to systematically manipulate the relative area of active to resting surfaces and the distance between them allowed investigation of the role of spatiotemporal profiles of regulatory molecules in localized bone remodeling. This setup was named the "trabecular bone organoid model" (FIG. 5C).

Figure 5D:
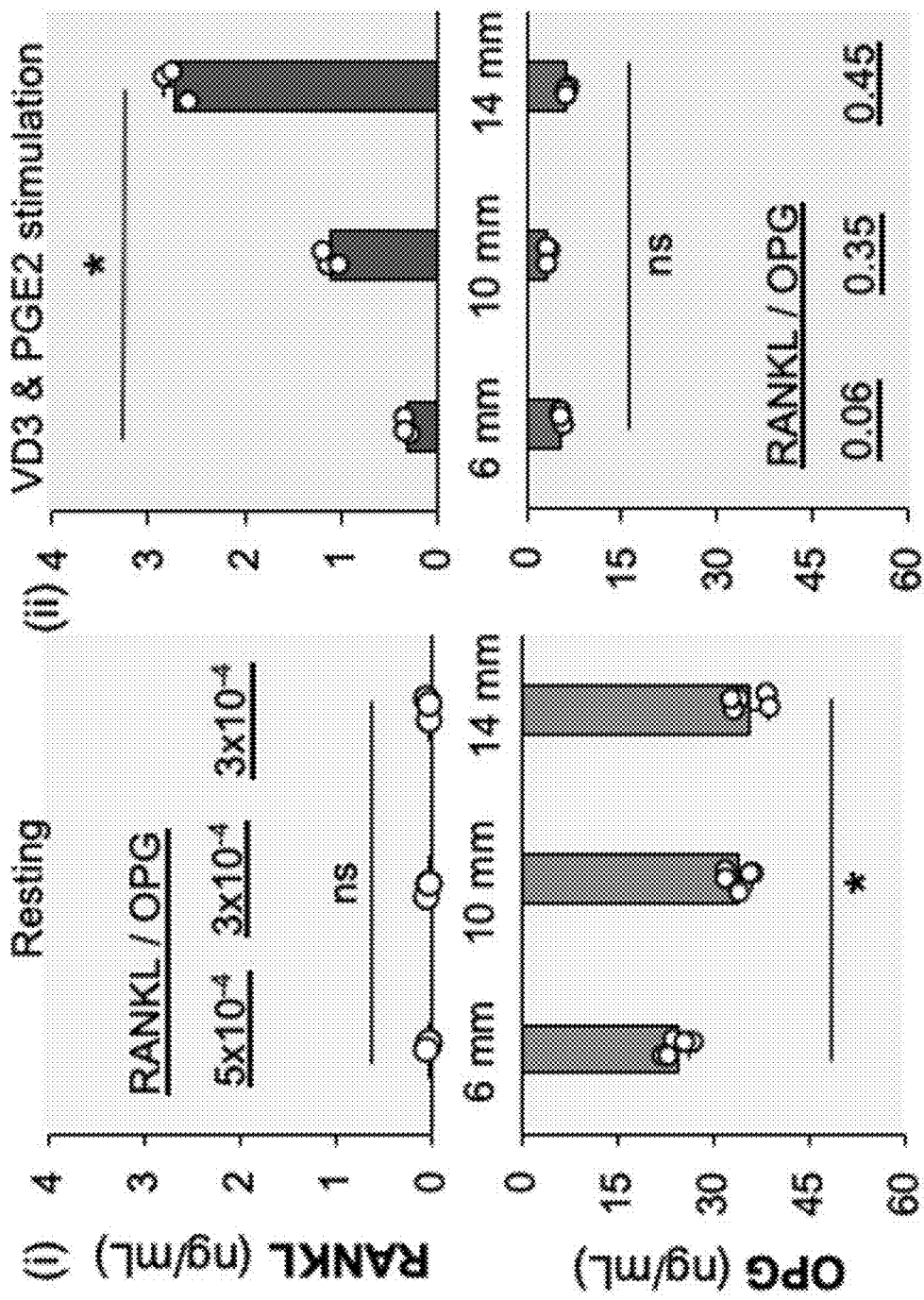
Figure 5E:
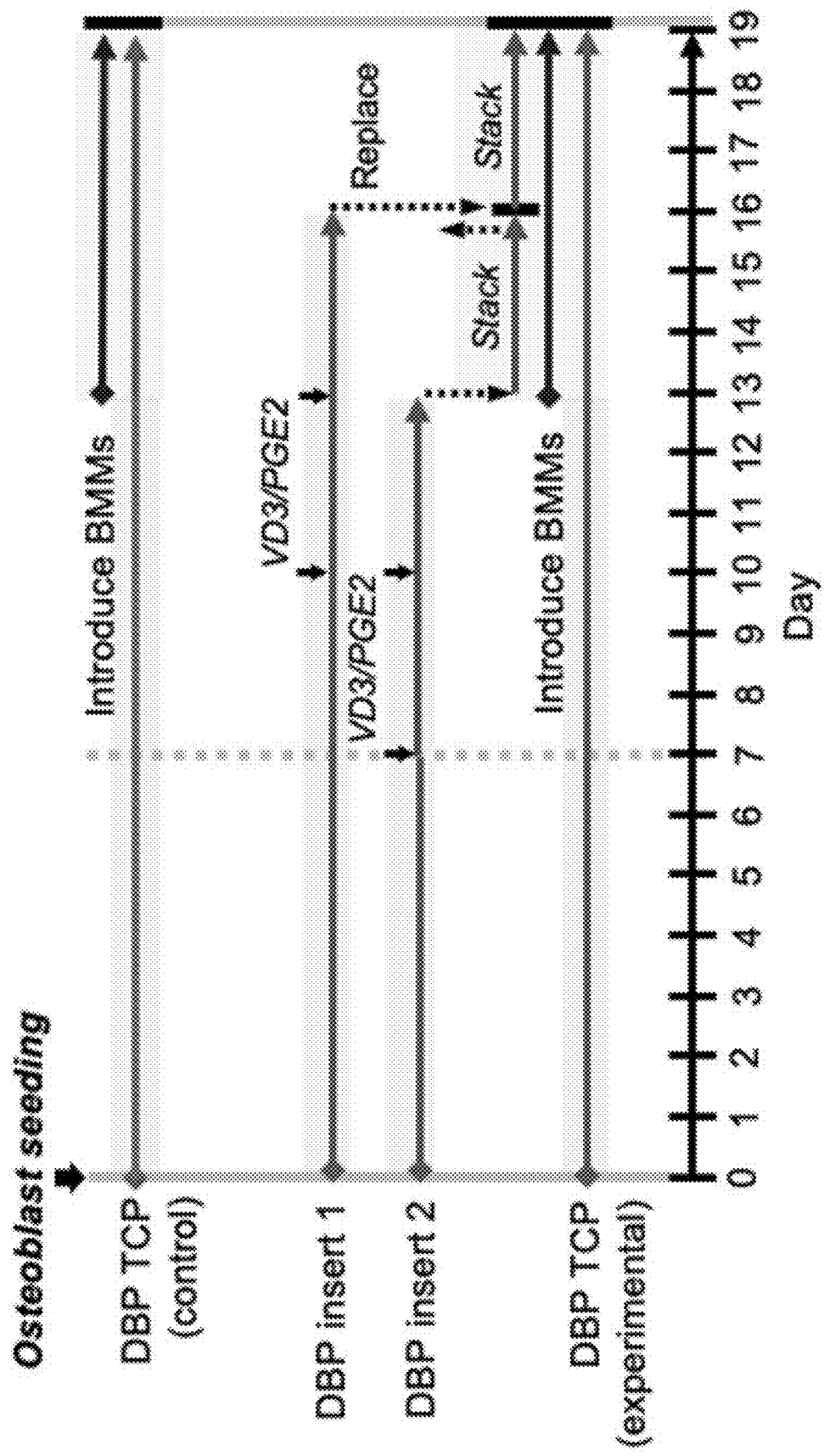

The study began by examining the secretion profiles of the DBP inserts. Osteoblasts cultured on various-sized DBP inserts for 1 week acquired the bone lining cell phenotype, with low RANKL and high OPG secretion (FIG. 5D,i). The cells were then stimulated with VD3 and PGE2 (two times, 3 days apart, to ensure that all cells were activated), showing that RANKL secretion increased in proportion to the size of the insert and OPG secretion decreased the same amount regardless of insert size (FIG. 5D,ii). Next the trabecular bone organoid model was assembled by placing a 16-mm DBP disk with bone lining cells in the well of a 24-well plate, adding $1\times10^6$ BMMs, and placing the stimulated DBP insert in the well over a spacer. The activated DBP insert was replaced after 3 days to maintain the level of stimulatory molecule secretion and terminated the coculture by 6 days (FIG. 5E).

Figure 5F:
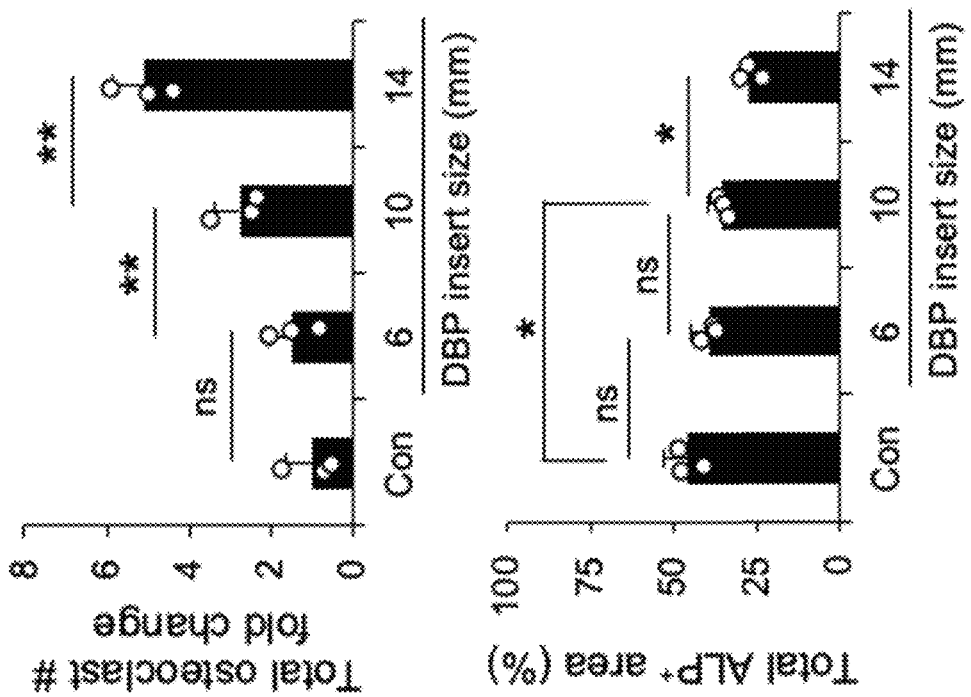
Figure 5F:
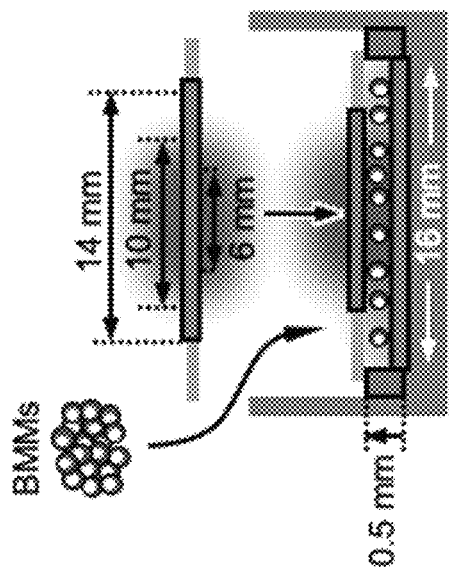
Figure 5G:
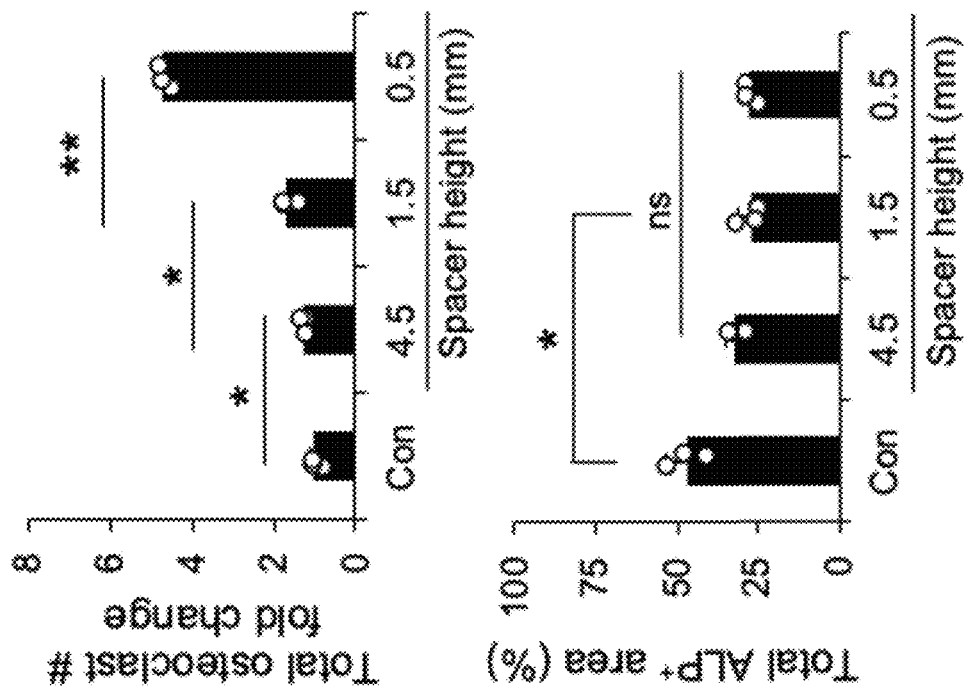
Figure 5G:
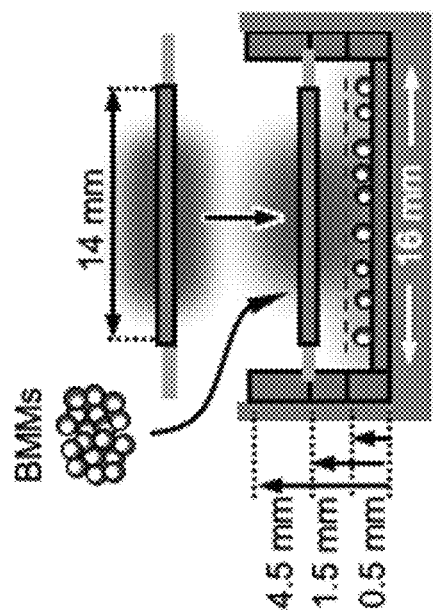

This trabecular bone organoid model was applied to study the effect of spatiotemporal profiles of stimulatory and suppressive molecules on the activation of bone lining cells and the differentiation of BMMs into osteoclasts under two distinct scenarios. First, the effect of activated surface area was examined by testing three sizes of DBP inserts with one spacer height (0.5 mm). At the end of 6 days of coculture, the activation of lining cells was quantified by measuring the ALP+ osteoblast area, and the differentiation of osteoclasts quantified by counting the number of TRAP+ multinucleated cells. The results showed a stepwise increase in osteoclast number with increasing DBP insert size. ALP production of bone lining cells was significantly lower with the 14-mm insert than it was with the 10 mm insert (FIG. 5F). The impact of the gap (spacer) dimension was then examined by testing three spacer heights with one DBP insert size (14 mm diameter). After 6 days of coculture, there was a stepwise decrease in osteoclast number with increasing spacer height. There was no significant difference in ALP+ osteoblast area (FIG. 5G). These results indicate that BMMs and bone lining cells are both responsive to the extent and gradient of stimulative molecules, but differentiation of BMMs into osteoclasts occurs in a more localized pattern than activation of bone lining cells does.

Quantitative spatial mapping of cellular activities in the trabecular bone organoid model shows effect of spatiotemporal profiles of regulatory molecules on bone remodeling activity.

Figure 6A:
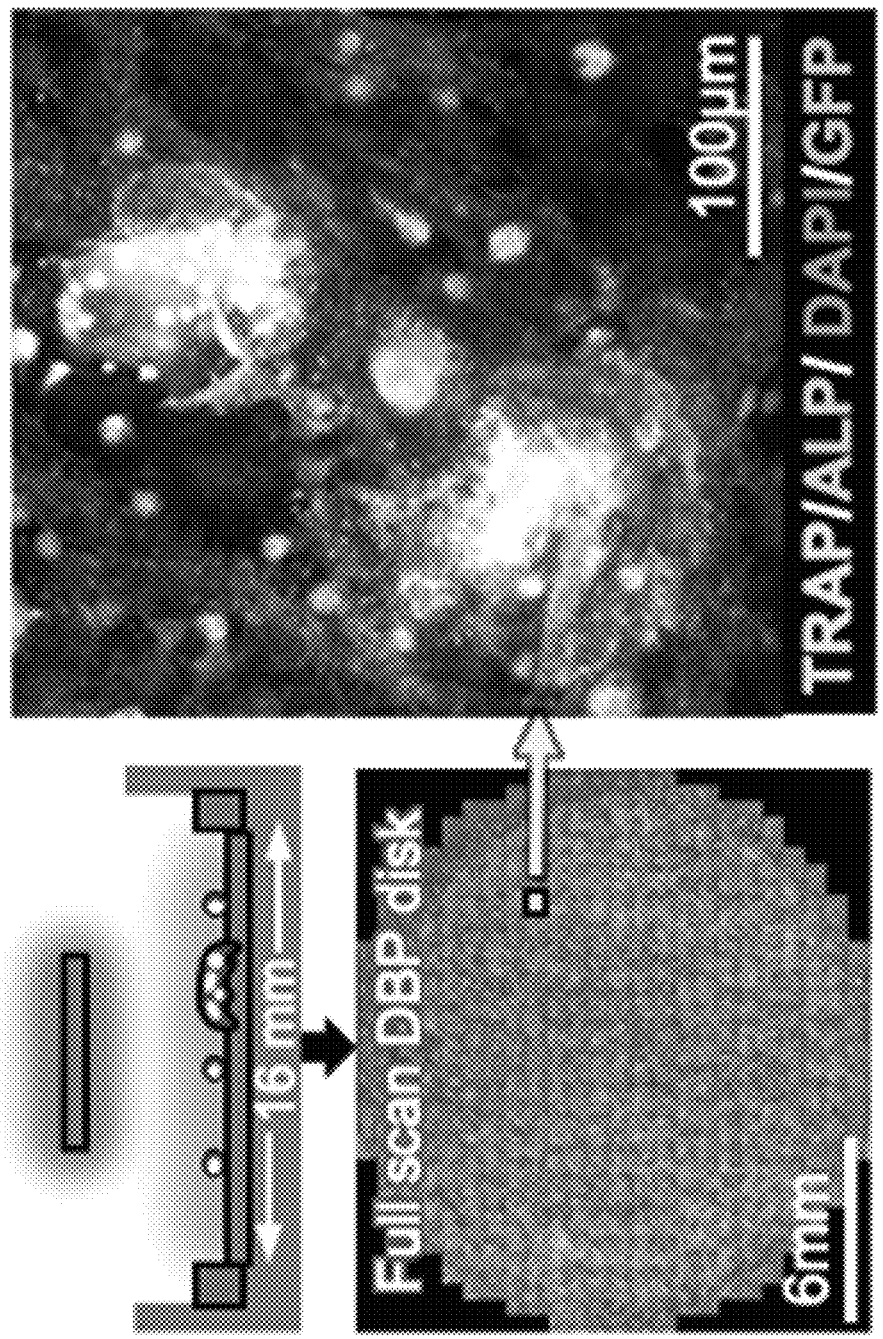
FIGS. 6A to 6G show quantitative spatial mapping of osteoblasts and osteoclasts captures paracrine- and cellular contact-mediated regulation of bone remodeling.
Figure 6B:
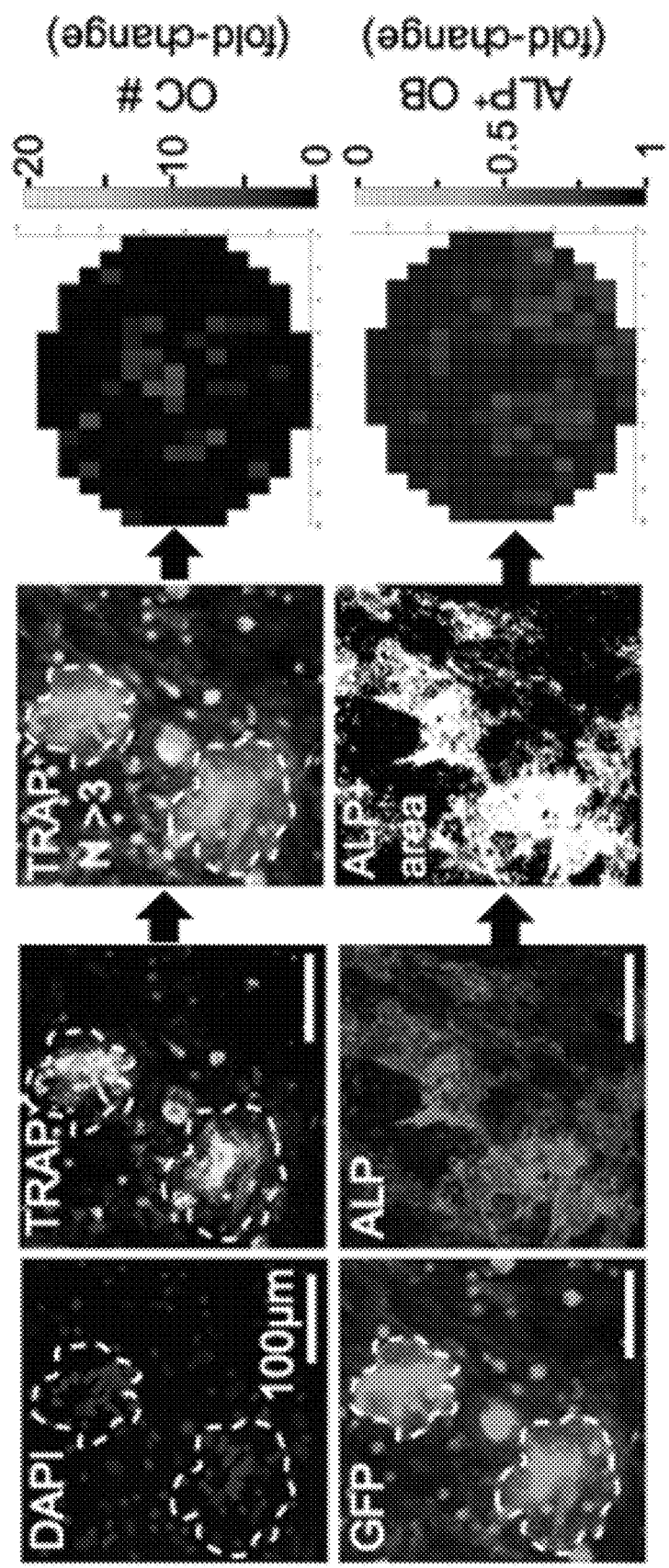
Figure 6C:
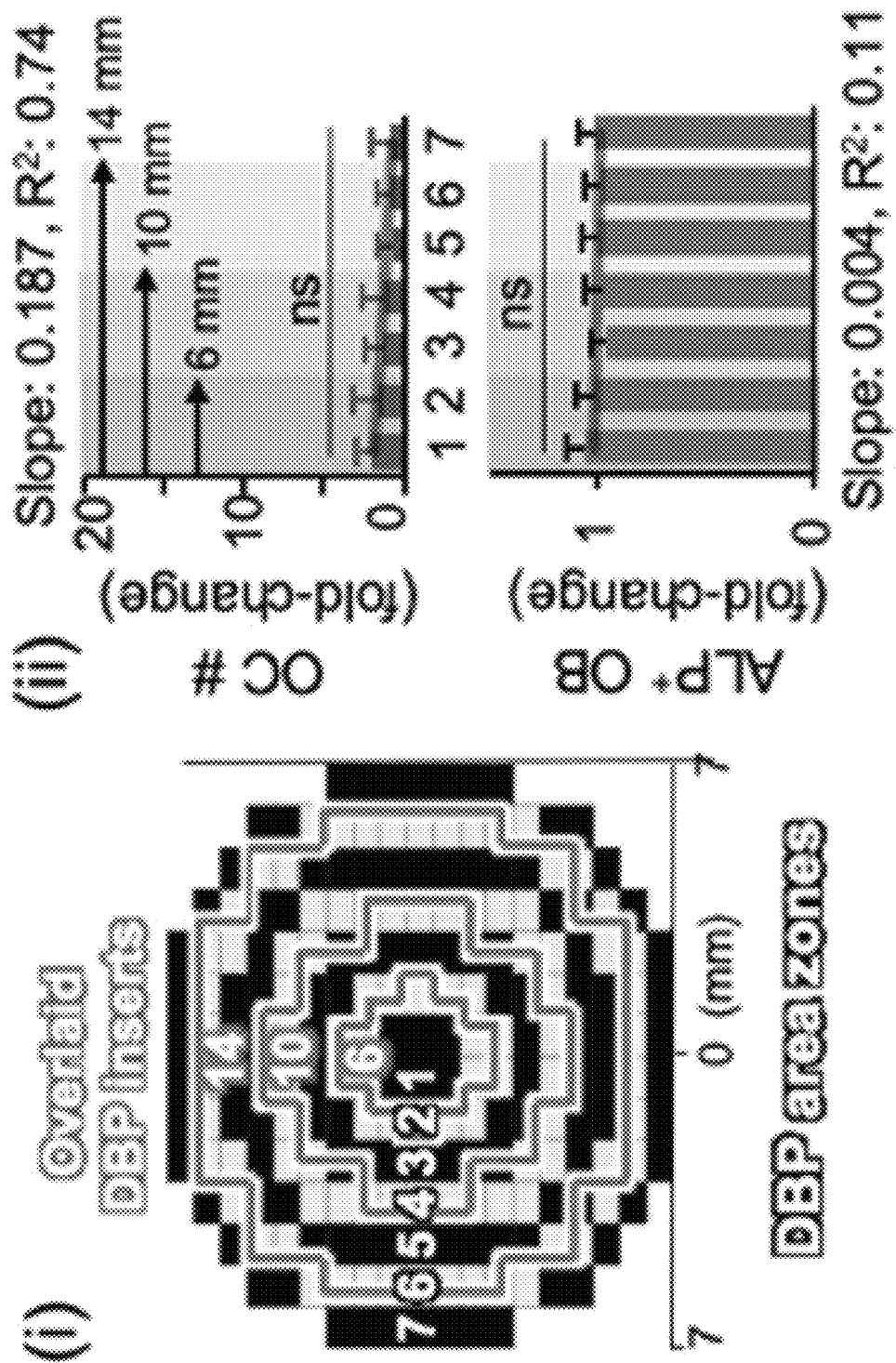
Figure 14:
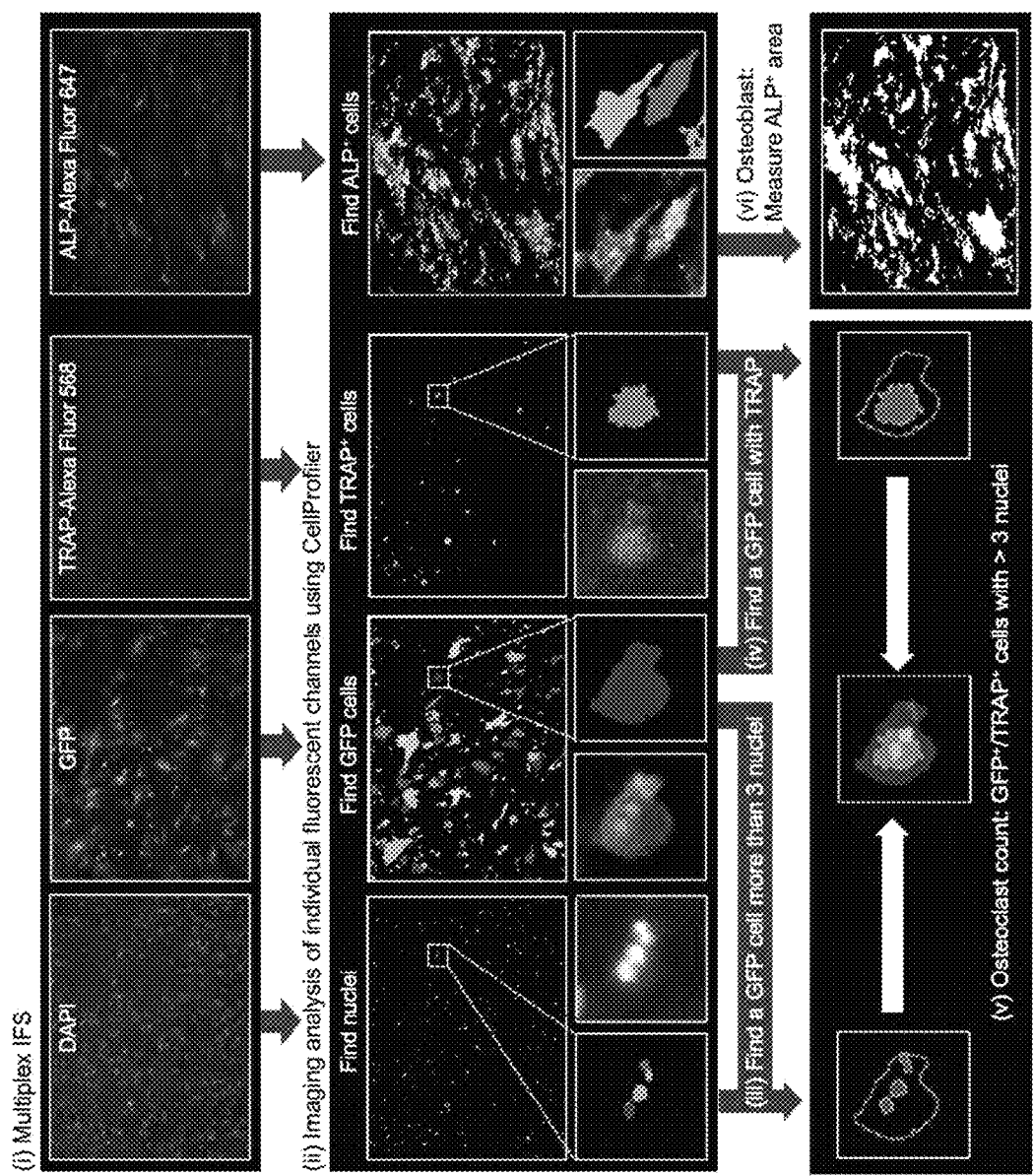
FIG. 14 shows multiplex quantitative imaging analysis algorithm of osteoclast number and ALP+ osteoblast area. (i) GFP-expressing osteoblast and osteoclasts were imaged. TRAP and ALP were labeled by Alexa Fluor 568 and Alexa Fluor 647, respectively. Cell nuclei was stained with DAPI. (ii) Individual channel images were processed to optimize the intensity and contrast by using Cellprofiler. Then, fluorescent signals were identified as objects. (iii) Nuclei in the same cytoplasm were grouped together by merging DAPI and GFP objects. (iv) TRAP+ cells were sorted by merging the GFP and Alexa Fluor 568 signals together. (v) TRAP+ groups with more than 3 nuclei were counted as multinucleated osteoclast. (vi) ALP+ area was quantified from the converted black and white images. (vi) ALP+ area was quantified from the converted black and white images. (black: background, white: ALP)

An algorithm was developed for multiplex quantitative mapping of cellular bone remodeling activities to elucidate the effects of spatiotemporal profiles of regulatory molecules on BMMs and bone lining cells. First, full surface scans of a DBP disk was conducted with four fluorescent channels: GFP, to distinguish cells from DBP; 4',6-diamidino-2-phenylindole (DAPI), to determine the number of nuclei in each cell; TRAP, to monitor osteoclast emergence; and ALP, to measure osteoblast activation (FIGS. 6A, 14). Three independent results were averaged and spatial heat maps of osteoblast and osteoclast activities relative to unstimulated controls generated (FIG. 6B). For statistical comparison, the surface of the DBP disk was discretized into seven concentric zones with 1-mm radius increments and plotted average fold-changes of osteoclast and osteoblast activities within each zone. A trend line was drawn, showing the slope and regression that describes the functional connection between spatiotemporal gradients of stimulatory molecules and local bone remodeling activity. There was no significant difference in spatial distribution of fluorescent markers in the unstimulated controls (FIG. 6C).

Figure 6E:
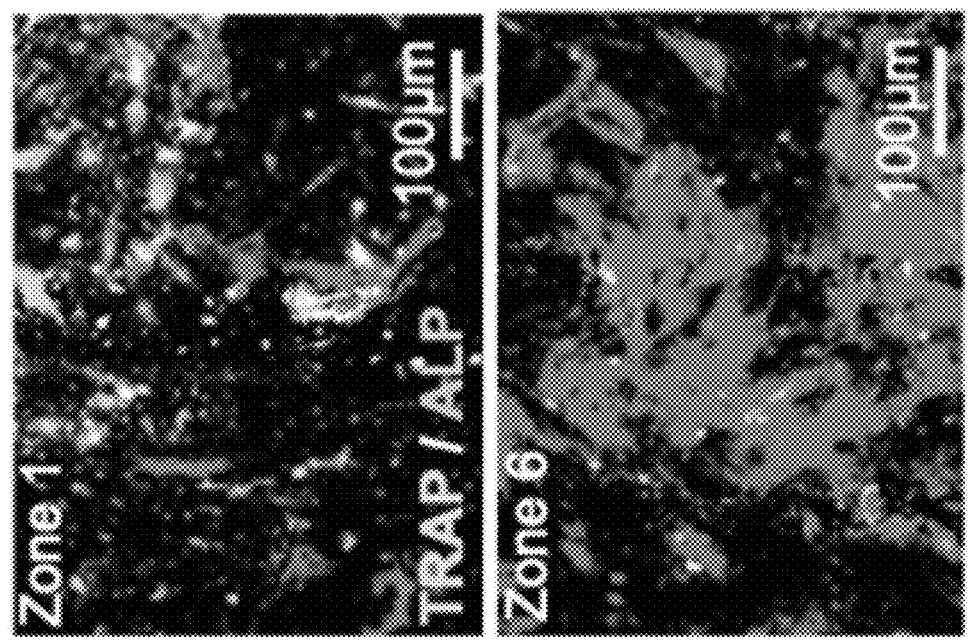
Figure 6D:
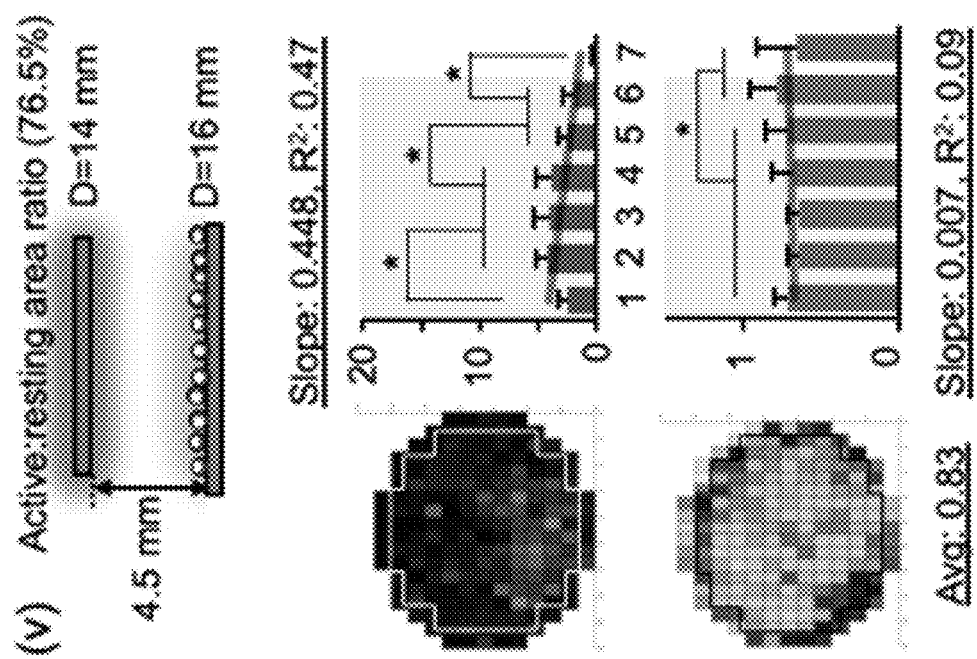

Multiplex quantitative imaging analysis was repeated for trabecular bone organoid models with three insert sizes and three spacer thicknesses. 6 mm, 10 mm, or 14 mm diameter activated DBP inserts were placed above DBP disks with bone lining cells, separated by a 0.5 mm-high spacer, in the well of a 24-well plate (FIG. 6D,i-iii). In wells with 6 mm inserts, the overall number of osteoclasts was no different than that of the unstimulated control, but spatial analysis revealed that the average fold change of osteoclasts in zones 1 and 2 was five times higher than it was in zones 3 through 7. Spatial analysis of 10 mm and 14 mm DBP inserts revealed a stepwise increase in osteoclast number from the edge to the center of the DBP disk. Linear analysis of the correlation between osteoclastogenesis and distance from the center of the DBP disk showed that the slope values increased with insert diameter. The average regression value was 0.66 across all insert sizes. Next, ALP expression change was analyzed in the osteoblasts on the DBP disk. In wells with 6 mm and 10 mm DBP inserts, the overall percentage of ALP+ osteoblasts was not significantly different than that of the unstimulated control; however, spatial analysis revealed a 20% decrease in ALP+ osteoblasts in zones 1 and 2 in wells with a 6 mm DBP insert and a 17% decrease in ALP+ osteoblasts in zones 1 through 3 of wells with a 10 mm DBP insert. The slope value decreased as DBP insert diameter increased from 6 to 14 mm, and the average regression was 0.78. These results capture the effect of the size and distance of activated surfaces on localized activation of BMMs and bone lining cells.

The experiment was repeated with the 14 mm-diameter insert and three spacer thicknesses: 0.5 mm, 1.5 mm, and 4.5 mm (FIG. 6D,iii-v). When the gap size increased, overall osteoclast differentiation decreased and localization to the central regions weakened. Slope values for osteoclast differentiation decreased as gap size increased. Regression analysis produced a value of 0.47 for the largest gap size, which indicates reduced impact of the activated surface on BMMs. When gap size increased from 0.5 to 4.5 mm, the ALP expression slope values approached zero, which indicates poor correlation to a localized phenomenon. However, average ALP$^+$ area did increase with increasing spacer height. These results indicate that localized activation of bone lining cells is sensitive to concentration of stimulative molecules but less dependent on distance of activated surfaces than differentiation of BMMs. Osteoclastogenesis was affected by both active area and distance but had a stronger correlation with active area.

Figure 6F:
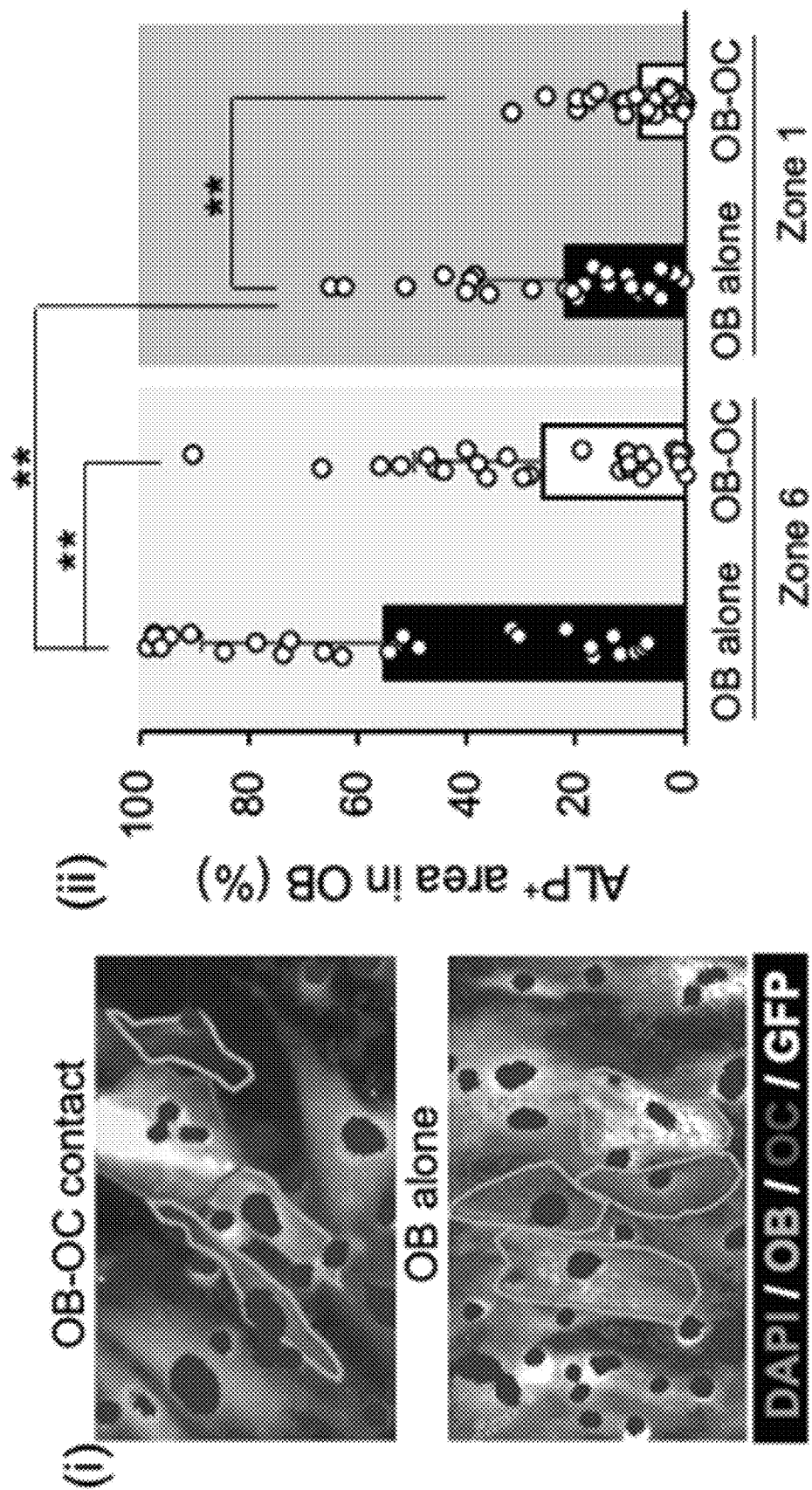
Figure 15:
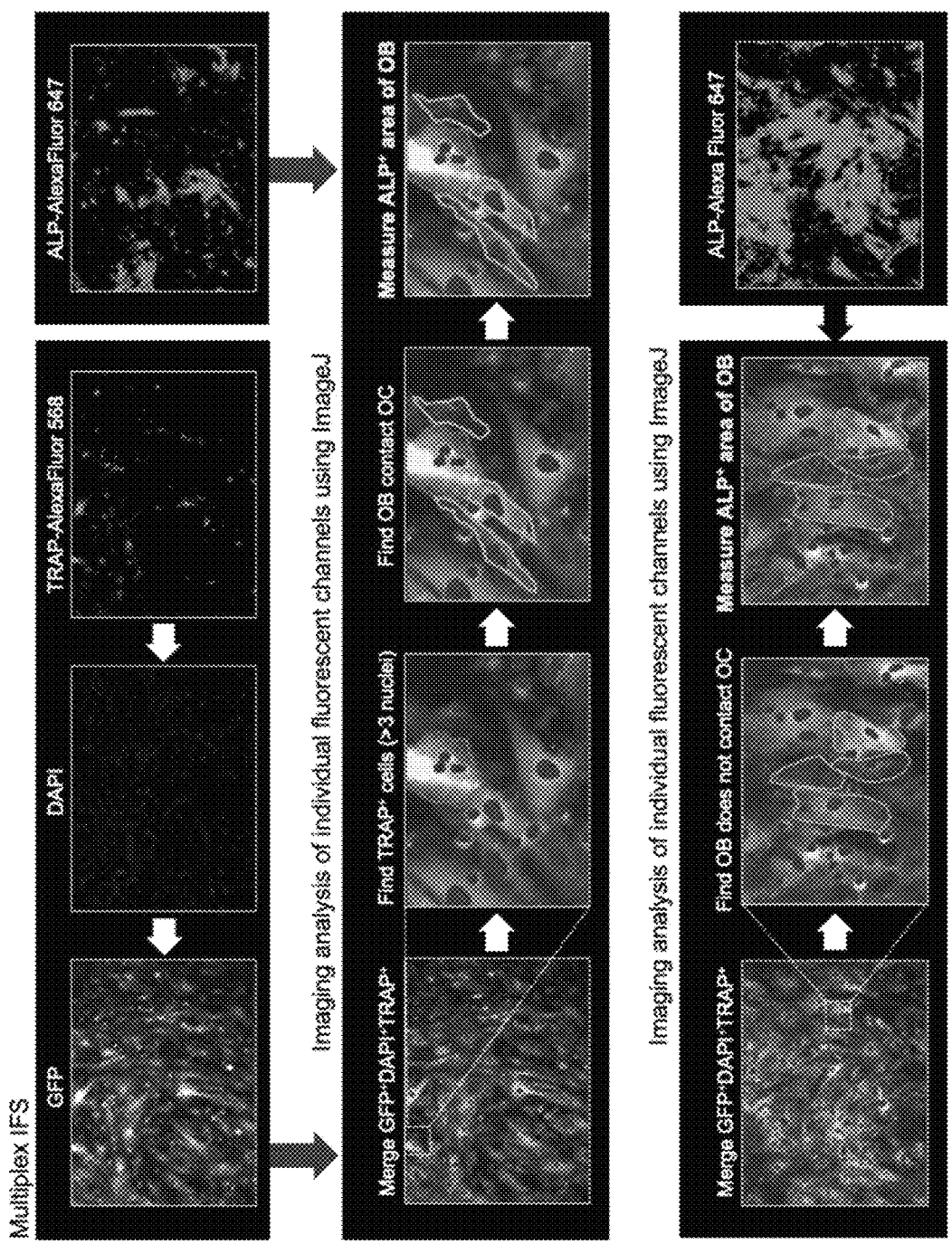
FIG. 15 shows multiplex quantitative imaging analysis algorithm of ALP+ osteoblasts that contact with osteoclasts and do not contact with osteoclasts.

Functional coupling of osteoblasts and osteoclasts can occur by means of direct contact as well as by paracrine signaling (Furuya, M, et al. Nat Commun 2018 9). Therefore, whether localized bone remodeling activity is affected by direct contact between osteoblasts and osteoclasts was examined. The central zone of the DBP disk accommodates higher numbers of osteoblasts and osteoclasts than the peripheral zones. To distinguish between the effect of stimulatory molecules and the effect of physical contact between osteoclasts and osteoblasts, the experiment was repeated with 6-mm DBP inserts. The reduction of ALP was measured in individual osteoblasts that were not in contact with osteoclasts in zone 1, which was exposed to high levels of stimulatory molecules, and in zone 6, which was exposed to low levels of stimulatory molecules (FIGS. 6E, 15). In zone 6, 55% of osteoblasts that were not in contact with osteoclasts were expressing ALP, whereas in zone 1, 22% of osteoblasts that did not have contact with osteoclasts were expressing ALP. This indicates that localized paracrine signaling activated bone lining cells. In both zones, osteoblasts that were in contact with osteoclasts were half as likely to express ALP as osteoblasts that were not in contact with osteoclasts. This indicates that osteoclasts activate bone lining cells via direct contact. These results suggest that there is a synergetic effect between localized stimulative paracrine signaling and osteoblast-osteoclast contact in the regulation of bone remodeling (FIG. 6F). Collectively, studies with the trabecular bone organoid model show the importance of spatiotemporal profiles of regulatory molecules and direct contact between osteoblasts and osteoclasts in regulating local trabecular bone remodeling.

DISCUSSION

To effectively reproduce the bone remodeling cycle, an in vitro bone tissue model should (i) be built from bone-relevant biomaterials that support intrinsic phenotypes and processes of osteoblasts and osteoclasts, (ii) include bone lining cells to simulate activation and termination of bone remodeling, and (iii) coculture osteogenic and hematopoietic cells to reproduce their functional interactions in the regulation of bone metabolism. With this in mind, a tissue-engineered trabecular bone organoid model was developed to investigate spatiotemporal aspects of molecular and cellular regulation of bone remodeling.

The trabecular bone organoid model is based on DBP, a novel, bone-derived biomaterial that supports intrinsic phenotypes and processes of osteoblasts and osteoclasts-cells that exclusively reside and function on the bone surface. DBP serves as a functional template on which osteoblasts rapidly deposit structural minerals, guided by the lamellar structure of the dense collagen, and resultantly form osteoid bone having a depth similar to that seen in vivo (Raina, V. J Clin Pathol 1972 25:229-232). DBP's semitransparency makes it possible to monitor ongoing cellular processes with fluorescent microscopy, and it is thin but durable enough to be handled easily. The consistent thickness and diameter of DBP supports reproducible functional assays including osteoclast mineral resorption, bone surface healing, and osteoblast metabolic switching assays. DBP can be produced in large quantities—more than 5,000 from one bovine femur—for high-throughput and high-content experiments. The model's modular design allows it to be integrated with other models to represent additional tissue complexity. For example, the space between two DBPs could be filled with marrow-mimicking viscous gels (Choi, J S, et al. Sci Adv 2017 3:e1600455; Bai, T, et al. Nat Med 2019 25:1566-1575), porous scaffolds (Li, X, et al. J Biomed Mater Res A 2013 101:2424-2435; Kwak, J G, et al. Adv Healthc Mater 2020 9:e1901556), or microfluidic chips (Chou, D B, et al. Nat Biomed Eng 2020 4:394-406; Glaser D E. et al., bioRxiv 2020.04.17.039339).

Figure 16A:
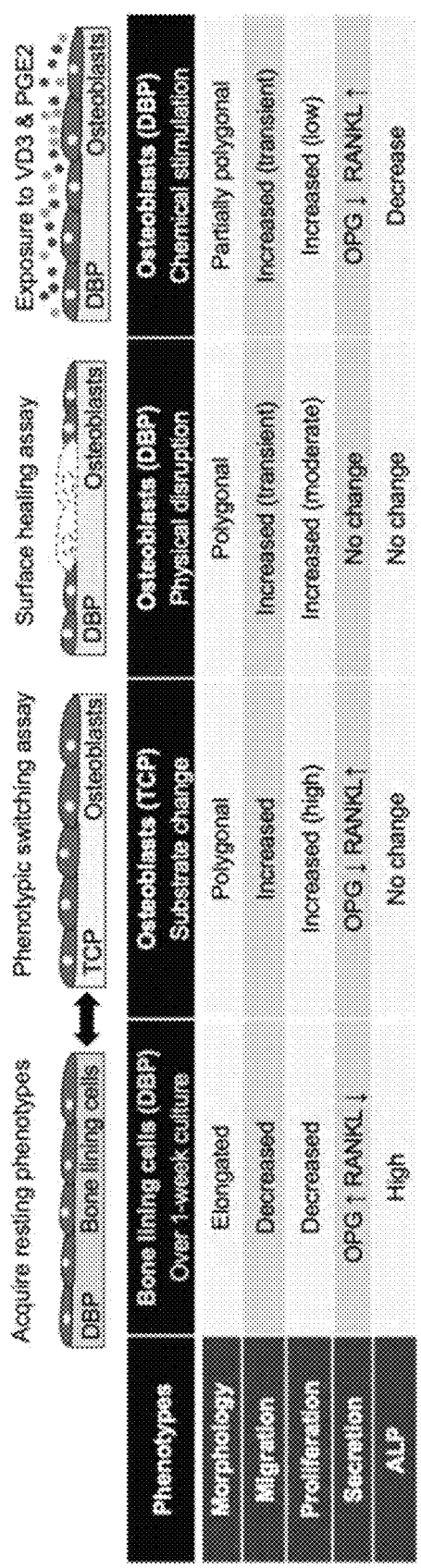
FIGS. 16A and 16B show phenotypic comparison of osteogenic cells between osteoblasts and bone lining cells.
Figure 16B:
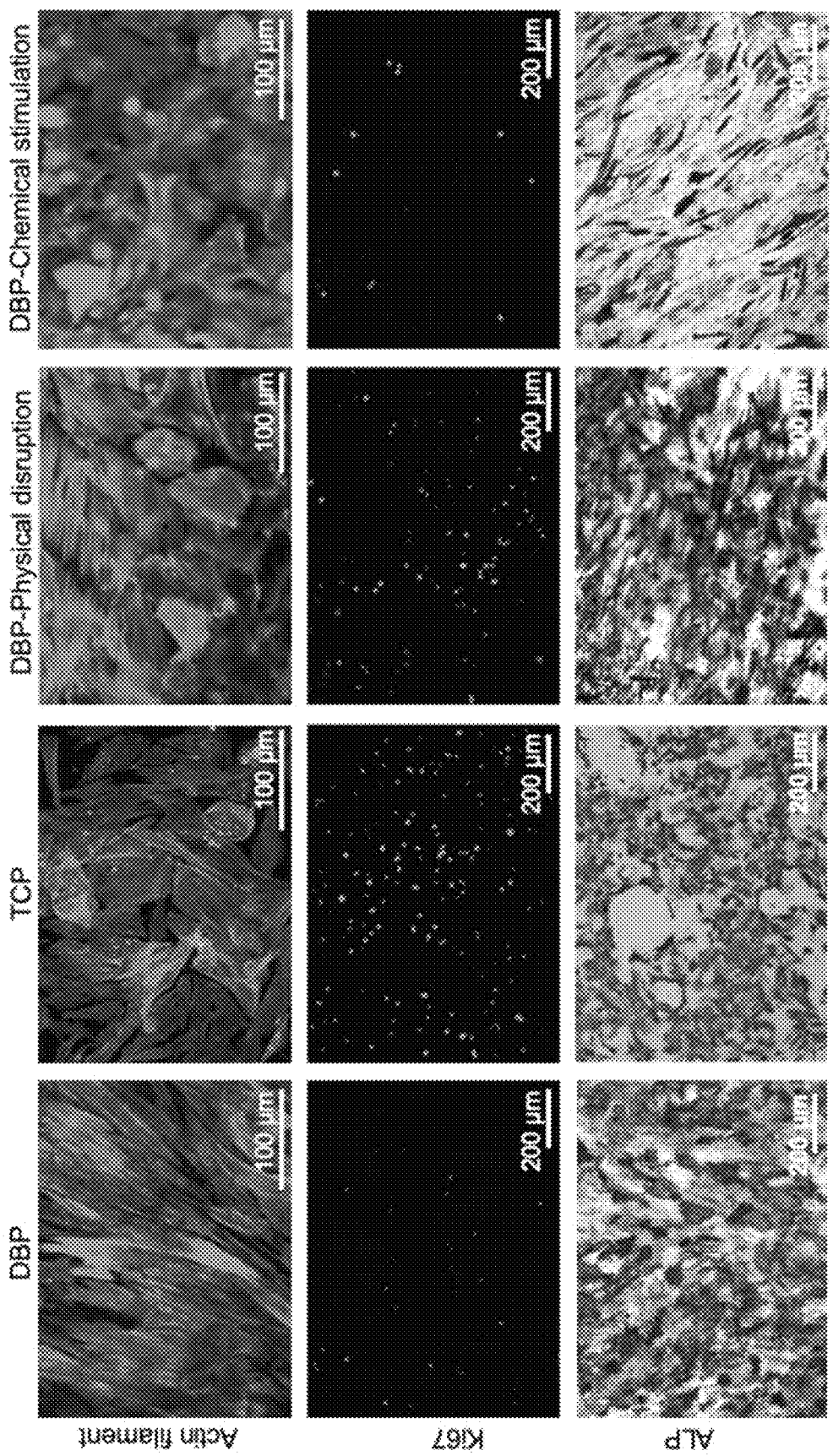
Figure 17:
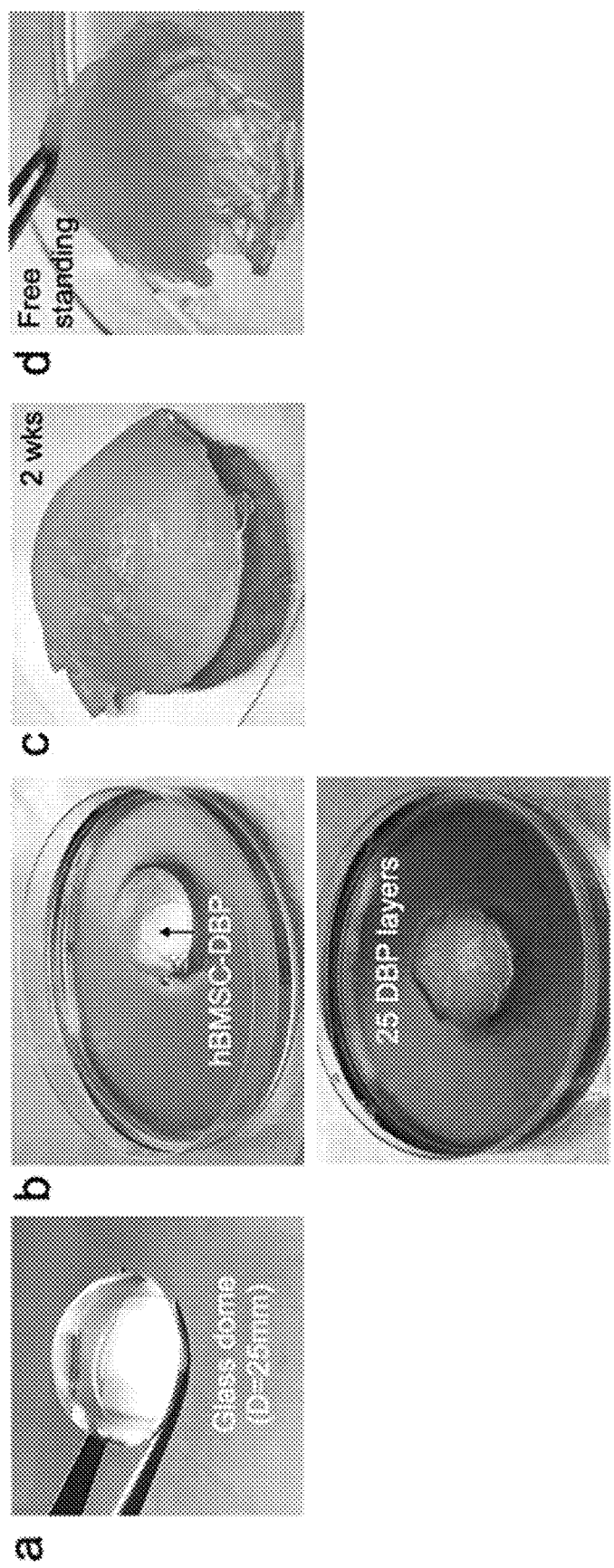
FIG. 17 is a demonstration of three-dimensional bone tissue graft generation. Panel (a) shows a glass dome (D=25 mm) used as a sample negative mold for customized bone tissue graft generation. Panel (b) shows 25 layers of human bone marrow stromal cell seeded demineralized bone papers were layered on a glass dorm. Panel (c) is an image after 2 weeks culture. Panel (d) shows removal of stacked freestanding demineralized bone papers that retains a dome shape.
Figure 18:
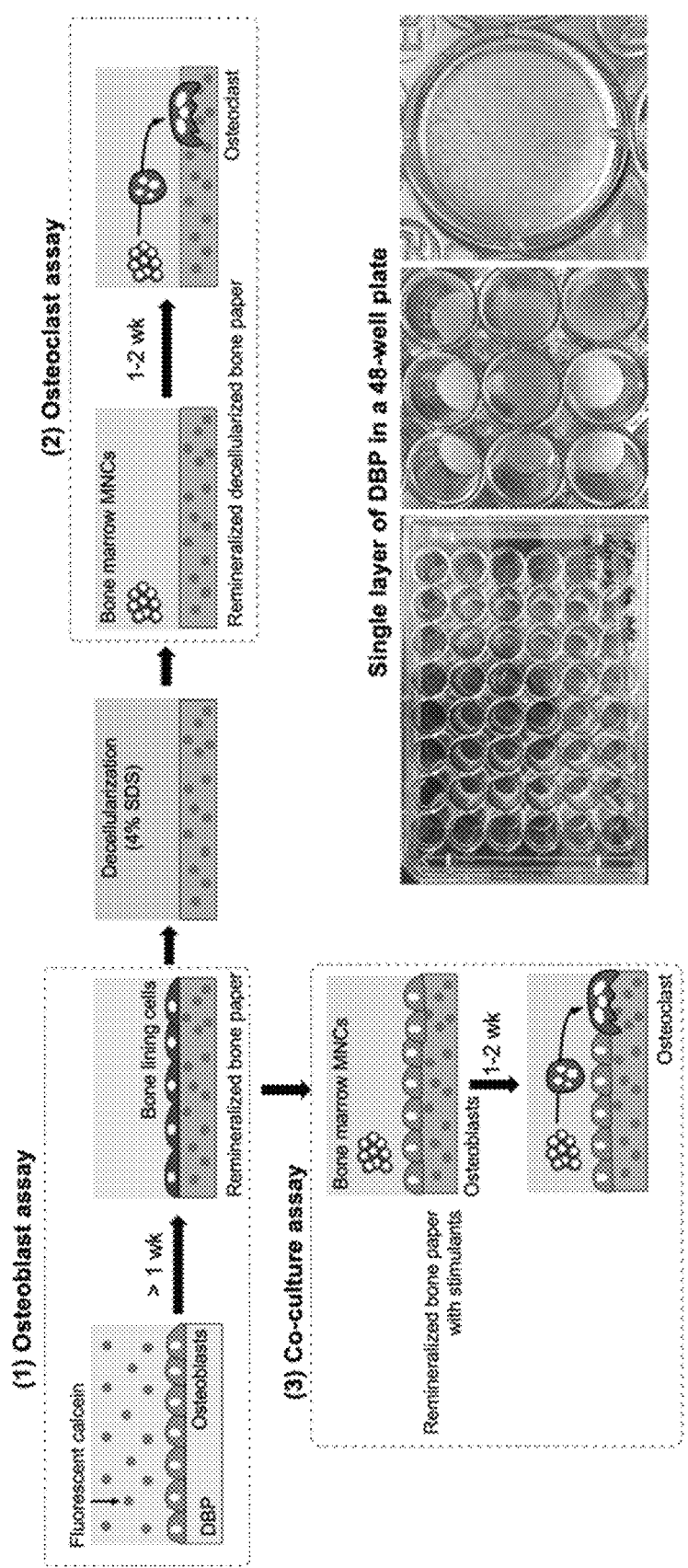
FIG. 18 illustrates an embodiment of a disclosed in vitro osteogenic assay on a single layer of DBP.

Bone lining cells cover most of the trabecular bone surface and likely play a significant role in biochemical regulation (Miller, S C, et al. Scanning Microsc 1989 3:953-960), but they are difficult to study because there are no definitive surface markers to distinguish bone lining cells from osteoblasts. DBP addresses this limitation by facilitating functional investigation of the bone lining cell phenotype. The disclosed experiments captured phenotypic distinctions between bone lining cells and osteoblasts on TCP and DBP including morphology, migration, proliferation and secretion (FIG. 16). Osteoblasts on DBP rapidly take on the bone lining cell phenotype, confirmed by the appearance of organized cellular morphology with gap junction communication, lower migration and proliferation, higher OPG secretion, and lower RANKL secretion than osteoblasts on TCP. The bone lining cells on DBP demonstrated ability to regain osteoblast activity when they were replated on TCP in the phenotypic switching assay, physically disrupted in the bone surface healing assay, or chemically stimulated with VD3 and PGE2. These results are consistent with recent in vivo findings that bone lining cells are a major source of osteoblasts (Matic, I, et al. Stem Cells 2016 34:2930-2942). Under chemical stimulation, the bone lining cells switched from a suppressive secretory profile (high OPG and low RANKL) to a stimulatory secretory profile (low OPG and high RANKL). This suggests that bone lining cells use paracrine signaling to actively regulate the extent and duration of localized bone remodeling. To the best of our knowledge, this is the first demonstration of a bone remodeling cycle that includes the controlled and reversible activation of bone lining cells under physiologically relevant chemical stimulation. This makes it possible to study the initiation and termination of bone remodeling, which is difficult to do with existing models.

Figure 6G:
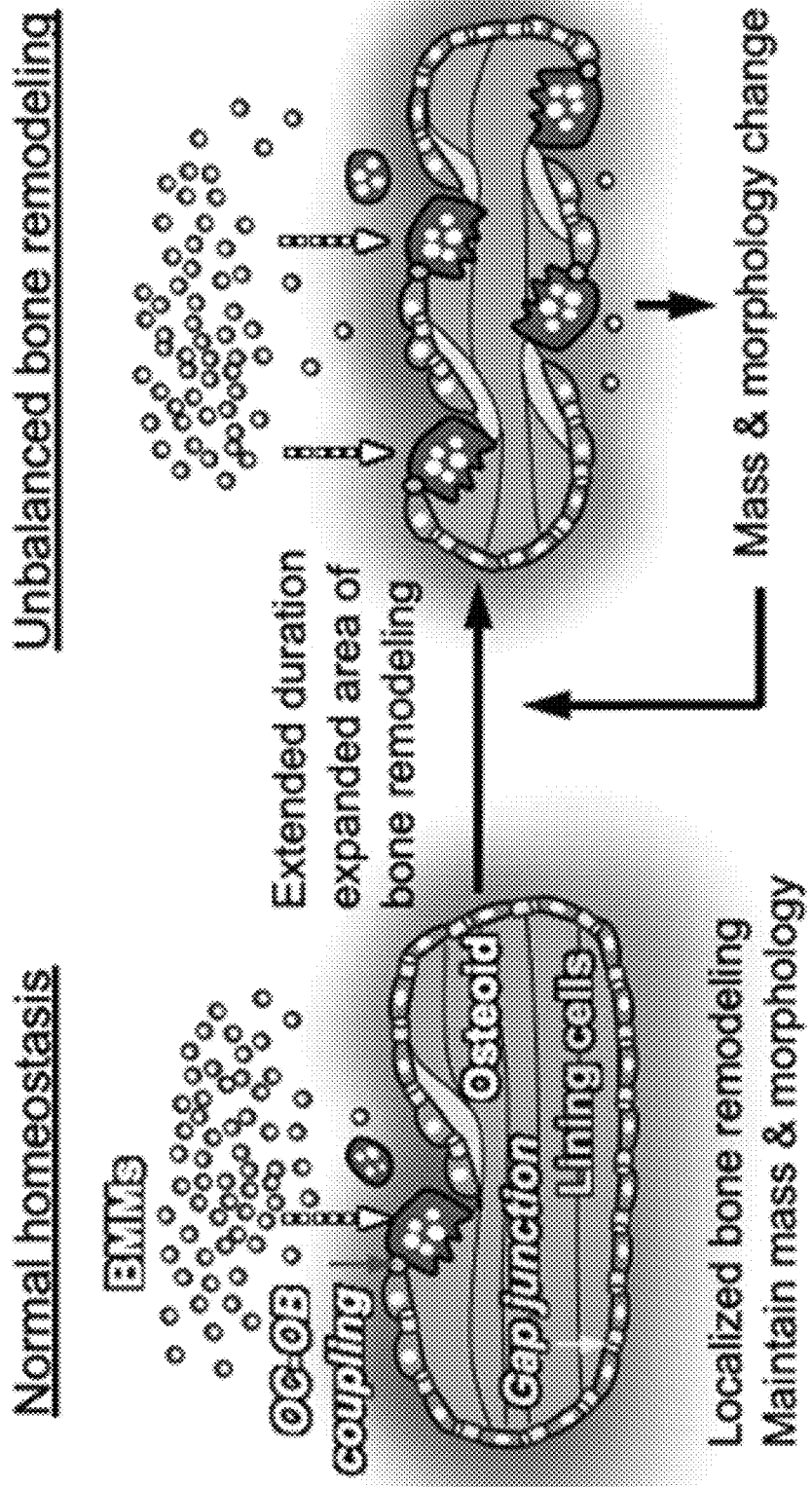

The coexistence of active and resting bone tissue surfaces was simulated by placing DBP disks with bone lining cells and BMMs in multiwell plates with DBP inserts containing stimulated osteoblasts. This setup enabled integration of osteogenic and hematopoietic cells in the context of trabecular bone cavities. The combination of resting and active DBP surfaces created defined spatiotemporal profiles of regulatory molecules, and BMMs introduced into the gap responded to the regionally concentrated paracrine signaling. The effect of the gap size between the DBP disk and the insert was weak, possibly because the selected gap dimensions were too large to capture the gradient effect (Wartlick, O, et al. Cold Spring Harb Perspect Biol 2009 1:a001255). The area of the activated DBP insert correlated positively with differentiation of BMMs into osteoclasts and activation of bone lining cells. Multiplex quantitative spatial analysis captured differences between BMMs and bone lining cells in the spatial pattern of response to paracrine molecules. These differences could be due to differences in cellular organization between osteogenic and hematopoietic cells (Mendez-Ferrer, S, et al. Nature 2010 466:829-834). Osteogenic cells develop multicellular organization and gap junction communication, and thus respond to stimuli as a collective group (Plotkin, L I, et al. Bone 2013 52:157-166). This collective response could attenuate their responsiveness to the gradient of stimulant signals and result in weak responsiveness. On the other hand, hematopoietic cells reside and function individually in the bone marrow (Mendez-Ferrer, S, et al. Nature 2010 466:829-834), which could cause them to be more sensitive to gradients of stimulative molecules and have a stronger spatial pattern of responsiveness. These results suggest that trabecular bone thickness and the number of osteogenic cells and their connectivity may be critical to keep bone remodeling localized. Quantitative image analysis elucidated the functional coupling between osteoblasts and osteoclasts. Coculture with osteoblasts increased differentiation and migration of osteoclasts. ALP expression in osteoblasts appeared to decrease as a result of direct contact with osteoclasts. Interactions between osteoblasts and osteoclasts have been viewed as individual cellular interactions (Chen, X, et al., Connect Tissue Res 2018 59:99-107), but these results suggest that individual hematopoietic cells interact with groups of osteogenic cells. Along with metabolic and anatomical considerations, this may be another intrinsic regulatory mechanism that confines localized bone remodeling activity (FIG. 6G).

Example 2: DBP Under Mechanical Vibration

Figure 20A:
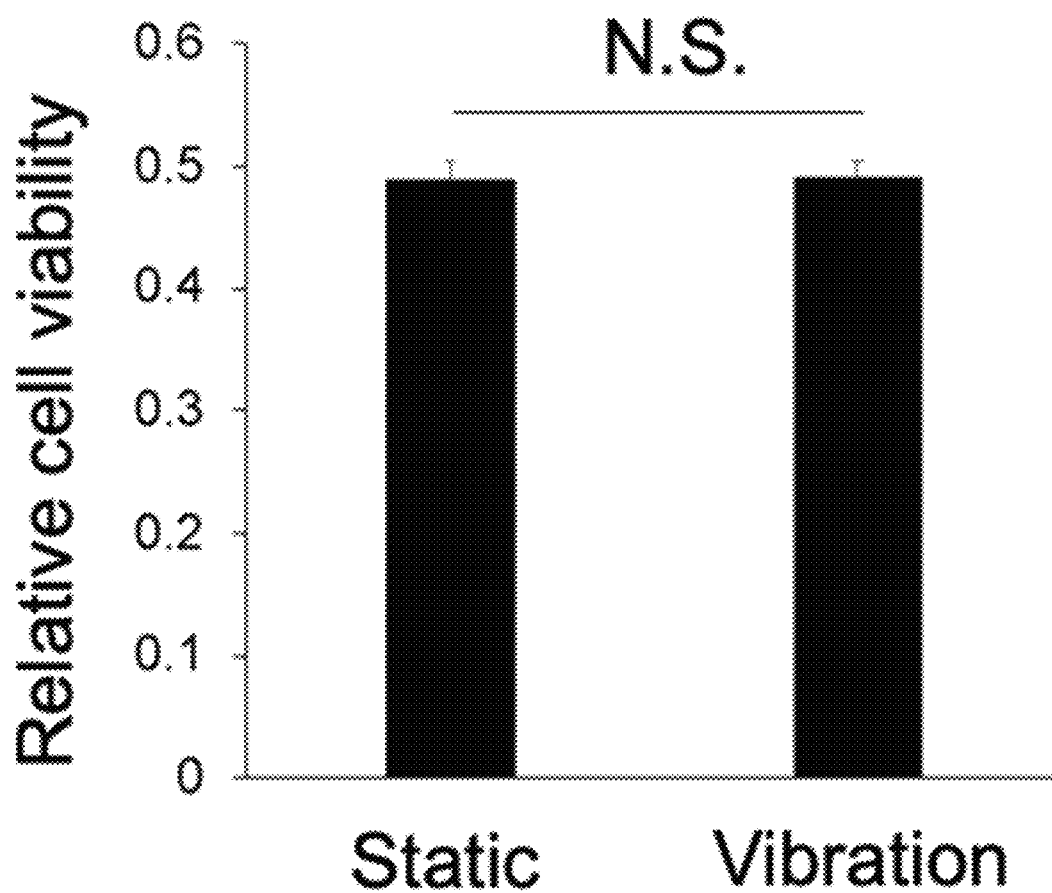
FIGS. 20A and 20B show DBP under vibration stimulates osteoblasts to deposit mineralized bone tissue development.
Figure 20B:
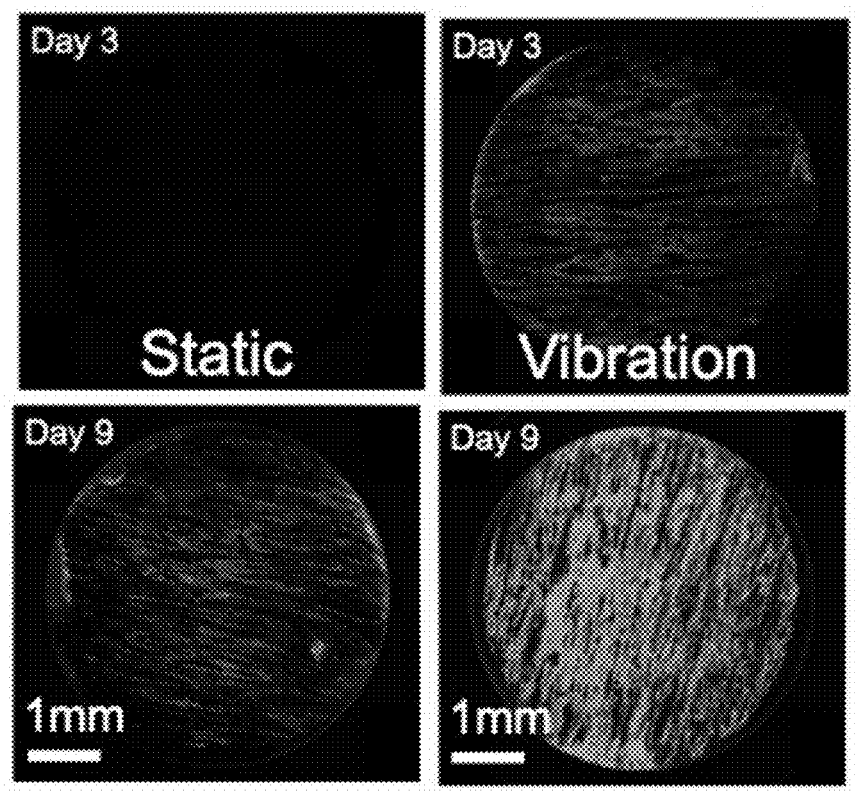
Figure 20B:
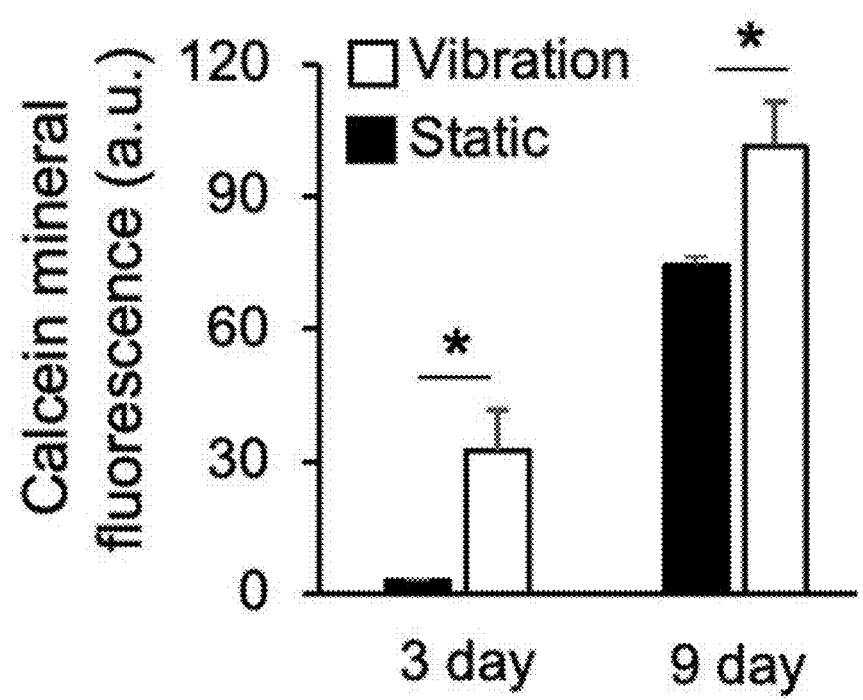

DBP under mechanical vibration significantly increases mineralized bone development by primary human and mouse osteoblasts. Primary human and mouse osteoblasts cultured on a DBP exhibited rapid, considerable deposition of mineralized bone matrix compared to tissue culture plastic. Furthermore, we have demonstrated that the mineralized bone tissue forming process further accelerated under mechanical stimulation. To trigger mechanical signals to osteoblasts residing on a DBP, a mechanoculture platform that vibrates collagen fibers on a DBP was developed. This mechanical vibration was applied 30 min per day up to 2 weeks, during which osteoblasts maintained comparable viability to a static culture (FIG. 20A). The time-course mineral deposition was visualized and quantitatively measured by conducting mineral binding fluorescent calcein staining. There was a significantly increased mineral deposition even after three days of vibrational culture, and high mineral deposition was continued at least nine days of vibrational culture (FIG. 20B). These results indicate that collagen fibers on DBP effectively respond to vibrational mechanical stimulation that triggers mechanotransduction of osteoblasts and subsequent mineralized bone-forming processes.

Figure 21C:
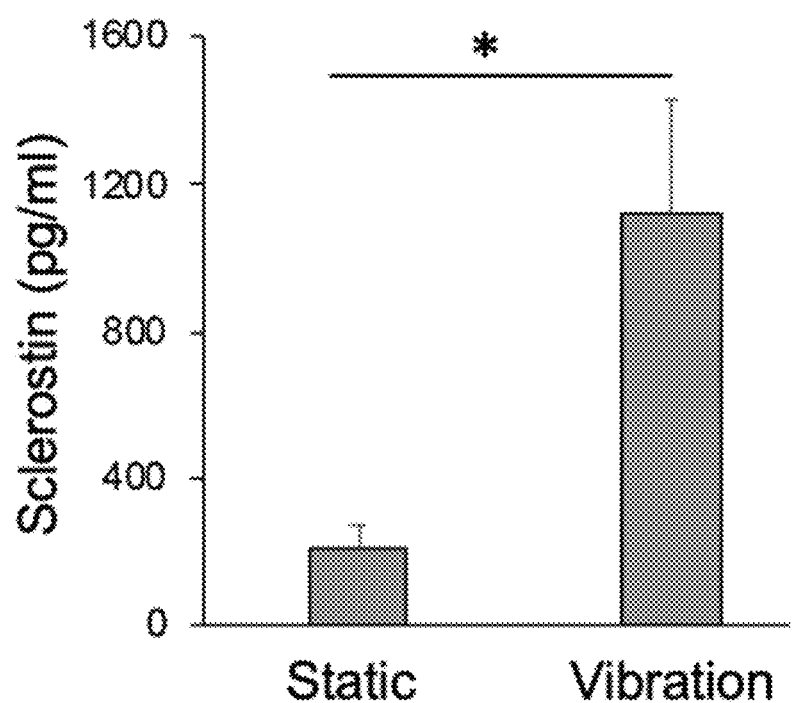

DBP under mechanical vibration significantly augments the response of mechanosensory osteocyte cell line (OCY454). The most potent mechanosensory cells in the bone tissue are osteocyte that comprises more than 90% of total bone cells. A murine pre-osteocyte cell line (OCY454) that expresses green fluorescence and secretes sclerostin when differentiated into mature osteocytes was accessed previously. When OCY454 cells on DBP were cultured under mechanical vibration, there was increased mineral deposition that decreased the optical transparency of DBP (FIG. 21A). Fluorescent microscopy imaging showed notably more green-fluorescent cells under mechanical vibration than static culture (FIG. 21B). ELISA analysis of conditioned medium further confirmed significantly increased sclerostin secretion, secreted by mature osteocytes in the body (FIG. 21C). These results indicate that DBP under mechanical vibration restores intrinsic phenotypes of osteocytes.

DBP demonstrates bone tissue regeneration in a mouse model. The initial impact of DBP to regenerate bone tissue was examined by using a standard calvaria bone defect model. We made a skin incision and a 3 mm diameter of the hole in an immunodeficient NSG mouse. This hole in the skull was filled with a 3 mm diameter and 100 μm thickness of a DBP. The skin incision was closed using sutures. After three weeks, mice we sacrificed and bone tissue development characterized. The initial characterization confirmed vascularized bone tissue development. Primary human osteoblasts are used to evaluate the clinical usage of DBP in bone tissue regeneration. Vibration on implanted DBP is evaluated to test if the vibration of DBP in vivo accelerates bone tissue development.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:
1. A method for assaying the effect of an agent on bone development or health, comprising
   (a) providing an assay system comprising
      (i) a multi-well culture plate,
      (ii) one or more layers of semi-transparent, demineralized, compact bone slices 10-1,000 μm thick in one or more wells of the multi-well culture plate, further comprising bone-promoting cells on the one or more layers, wherein the compact bone slices have been remineralized by the bone-promoting cells, and
      (iii) a culture medium configured to promote or maintain bone development;
   (b) adding a candidate agent to the culture medium of the assay system; and
   (c) measuring at least one parameter of bone development in the assay system to determine if the candidate agent affected bone development, bone resorption, or health.
2. The method of claim 1, wherein the at least one parameter of bone development comprises mineralization or resorption of pre-existing mineral.
3. The method of claim 1, wherein the at least one parameter of bone development is assayed by measuring one or more biomarkers related to bone metabolism selected from the group consisting of bone-specific alkaline phosphatase (BALP); osteocalcin (OC); propeptides of type I procollagen (P1NP and P1CP); pyridinoline (PYD); deoxypyridoline (DPD); carboxy-terminal crosslinked telopeptide of type 1 collagen (CTX-1); amino-terminal crosslinked telopeptide of type 1 collagen (NTX-1); hydroxyproline (HYP); hydroxylysine (HYL); bone sialoprotein (BSP); osteopontin (OP); tartrate-resistant acid phosphatase 5b (TRAP 5b); cathepsin K (CTSK); receptor activator of NF-KB ligand (RANKL), osteoprotegerin (OPG), dickkopf-1 (DDK-1); and sclerostin.

4. The method of claim 1, wherein the culture medium is configured to promote bone development, bone resorption, or both.

5. The method of claim 1, wherein the compact bone slices have a surface area of at least 1 cm$^2$.

6. The method of claim 1, wherein the multi-well culture plate further comprises a means for vibrating collagen fibers in the compact bone slices.

* * * * *